United States Patent
Sabry et al.

(10) Patent No.: US 12,061,116 B2
(45) Date of Patent: Aug. 13, 2024

(54) COMPACT SPECTRAL ANALYZER

(71) Applicant: Si-Ware Systems, Cairo (EG)

(72) Inventors: Yasser M. Sabry, Cairo (EG); Mohamed H. Al Haron, Cairo (EG); Bassem Mortada, Cairo (EG); Ahmed Othman, Cairo (EG); Diaa Khalil, Cairo (EG); Bassam Saadany, Cairo (EG); Ahmed Shebl, Cairo (EG); Botros George Iskander Shenouda, Cairo (EG)

(73) Assignee: SI-WARE SYSTEMS, Cairo (EG)

( * ) Notice: Subject to any disclaimer, the term of this patent is extended or adjusted under 35 U.S.C. 154(b) by 161 days.

(21) Appl. No.: 17/876,250

(22) Filed: Jul. 28, 2022

(65) Prior Publication Data

US 2023/0036551 A1    Feb. 2, 2023

Related U.S. Application Data

(60) Provisional application No. 63/227,284, filed on Jul. 29, 2021.

(51) Int. Cl.
*G01J 3/02* (2006.01)
*G01J 3/10* (2006.01)
(Continued)

(52) U.S. Cl.
CPC .......... *G01J 3/0256* (2013.01); *G01J 3/0208* (2013.01); *G01J 3/0216* (2013.01); *G01J 3/0286* (2013.01);
(Continued)

(58) Field of Classification Search
CPC ......... G01J 2003/283; G01J 2003/2873; G01J 2003/4534; G01J 3/0208; G01J 3/0216;
(Continued)

(56) References Cited

U.S. PATENT DOCUMENTS

| 5,246,004 A | 9/1993 | Clarke et al. |
|---|---|---|
| 6,675,030 B2 | 1/2004 | Ciurczak et al. |

(Continued)

FOREIGN PATENT DOCUMENTS

| DE | 102019126050 A1 | 4/2021 |
|---|---|---|
| WO | 2017218778 A1 | 12/2017 |

(Continued)

OTHER PUBLICATIONS

Kollias, Nikiforos, and Georgios N Stamatas. "Optical non-invasive approaches to diagnosis of skin diseases." The journal of investigative dermatology. Symposium proceedings vol. 7,1 (2002): 64-75.

(Continued)

*Primary Examiner* — Gordon J Stock, Jr.
(74) *Attorney, Agent, or Firm* — Loza & Loza, LLP; Holly L. Rudnick

(57) ABSTRACT

Aspects relate to a spectral analyzer that can be used for biological sample detection. The spectral analyzer includes an optical window configured to receive a sample and a spectral sensor including a chassis having various component assembled thereon. Examples of components may include a light source, a light modulator, illumination and collection optical elements, a detector, and a processor. The spectral analyzer is configured to obtain spectral data representative of a spectrum of the sample using, for example, an artificial intelligence (AI) engine. The spectral analyzer further includes a thermal separator positioned between the light modulator and the light source.

47 Claims, 38 Drawing Sheets

(51) Int. Cl.
*G01J 3/28* (2006.01)
*G01J 3/45* (2006.01)
*G01J 3/453* (2006.01)
*G01N 33/483* (2006.01)

(52) U.S. Cl.
CPC .............. *G01J 3/108* (2013.01); *G01J 3/45* (2013.01); *G01J 3/4532* (2013.01); *G01N 33/4833* (2013.01); *G01J 2003/283* (2013.01); *G01J 2003/2873* (2013.01); *G01J 2003/4534* (2013.01)

(58) Field of Classification Search
CPC ...... G01J 3/0256; G01J 3/0259; G01J 3/0262; G01J 3/027; G01J 3/0272; G01J 3/0286; G01J 3/0291; G01J 3/108; G01J 3/44; G01J 3/45; G01J 3/4532; G01J 3/4535; G01N 33/4833; G01N 2021/0112; G01N 21/25; G01N 21/255
See application file for complete search history.

(56) References Cited

U.S. PATENT DOCUMENTS

| | | | |
|---|---|---|---|
| 7,061,618 B2* | 6/2006 | Atia .......................... | G01J 3/10 356/519 |
| 7,403,804 B2 | 7/2008 | Ridder et al. | |
| 8,379,199 B2* | 2/2013 | Freese ..................... | G01J 3/021 356/303 |
| 8,660,637 B2* | 2/2014 | Crowley ............... | G01J 3/0208 600/478 |
| 11,320,310 B2* | 5/2022 | Siess ..................... | G01J 3/0208 |
| 11,841,268 B2* | 12/2023 | Sabry ................. | G02B 19/0019 |
| 2011/0222067 A1 | 9/2011 | Saadany et al. | |
| 2023/0076993 A1* | 3/2023 | Shenouda ............. | G01J 3/4531 |
| 2023/0175890 A1* | 6/2023 | Morecroft ............... | G01J 3/433 356/303 |
| 2023/0266234 A1* | 8/2023 | Oeguen ................. | G01J 3/0256 356/326 |

FOREIGN PATENT DOCUMENTS

| | | |
|---|---|---|
| WO | 2019177941 A1 | 9/2019 |
| WO | 2021058261 A1 | 4/2021 |

OTHER PUBLICATIONS

Vigneswaran Narayanamurthy, P. Padmapriya, A. Noorasafrin, B. Pooja, K. Hema, Al'aina Yuhainis Firus Khan, K. Nithyakalyanic and Fahmi Samsurib, "Skin cancer detection using non-invasive techniques", RSC Adv., 2018, 8, 28095.

Ziyi Yu, Nan Jiang, Sergei G Kazarian, Savas Tasoglu and Ali K Yetisen , "Optical sensors for continuous glucose monitoring", © 2021 IOP Publishing Ltd, Progress in Biomedical Engineering, vol. 3, No. 2.

Ridder TD, Hendee SP, Brown CD. Noninvasive Alcohol Testing Using Diffuse Reflectance Near-Infrared Spectroscopy. Applied Spectroscopy. 2005;59(2):181-189.

Cech, L.S., Nagolu, M., Rumps, D., Steeg, B.J., Treese, D., Laaksonen, B.D., Tehseldar, S., & Ridder, T, "Introduction of a solid state, non-invasive human touch based alcohol sensor", 24th International Technical Conference on the Enhanced Safety of Vehicles (ESV) 2015.

PCT/US2022/038912. International Search Report & Written Opinion (Nov. 23, 2022), 14 pages.

* cited by examiner

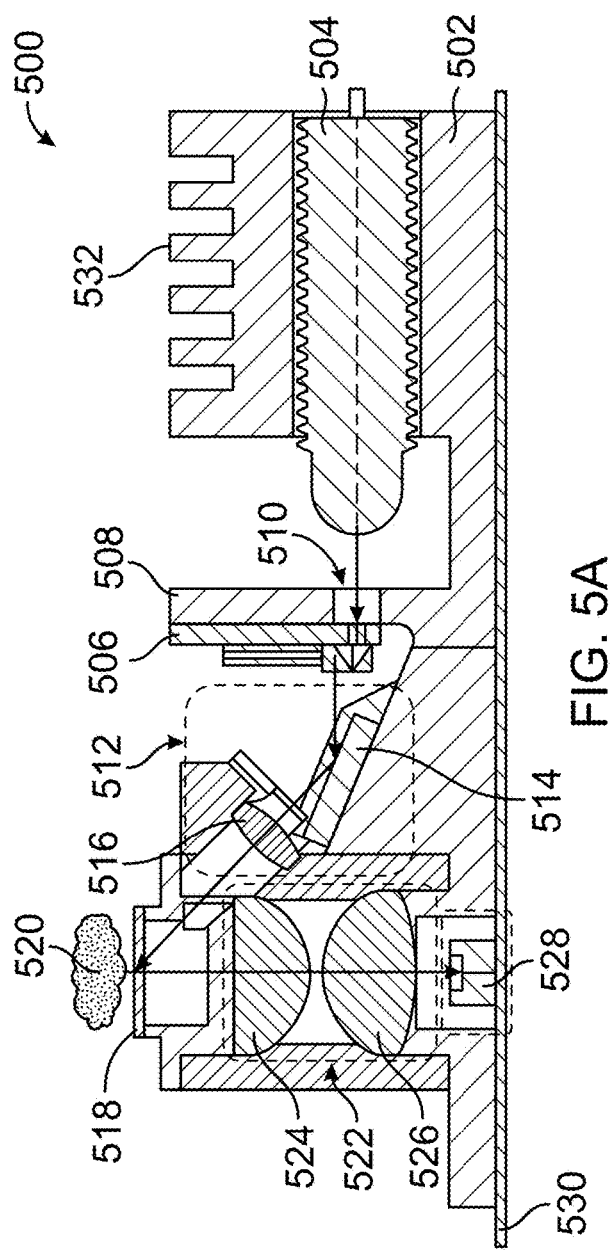
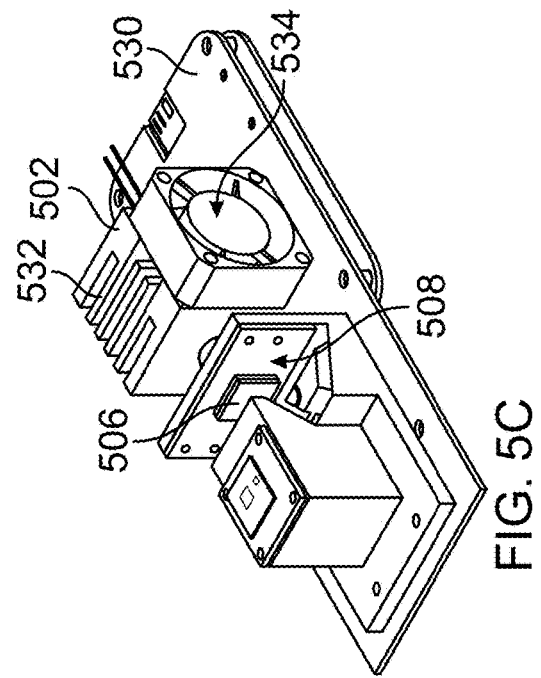
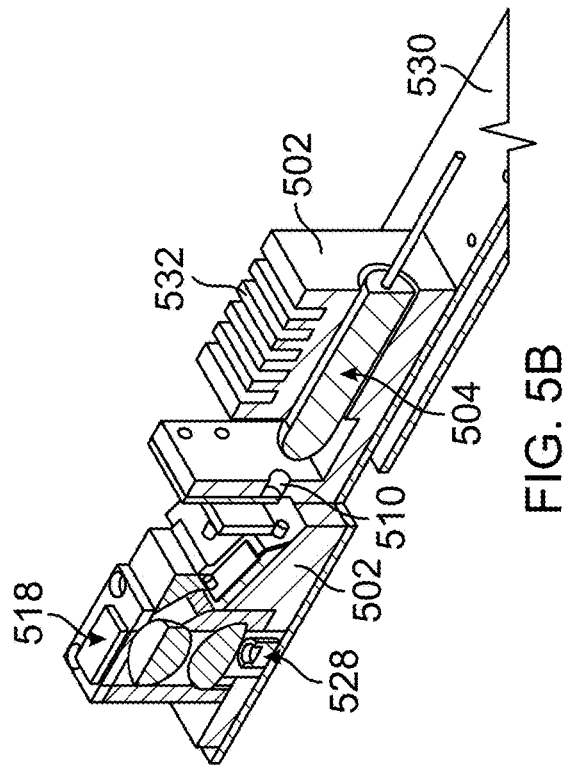

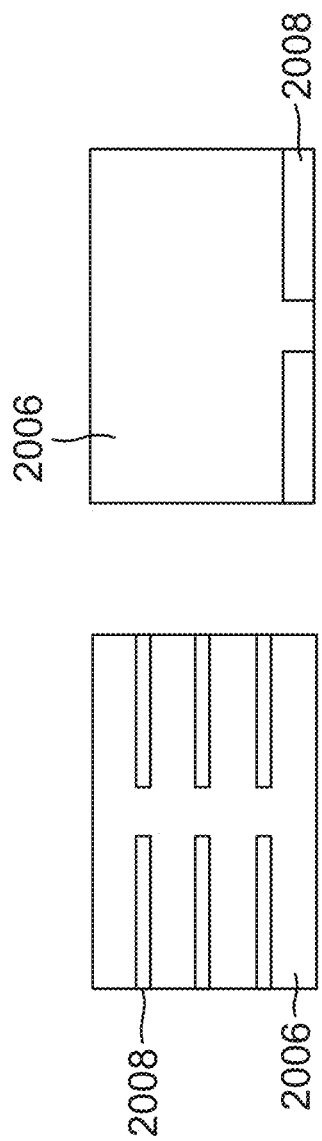
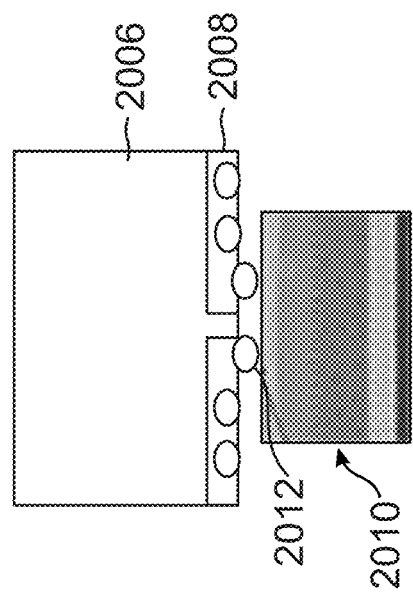
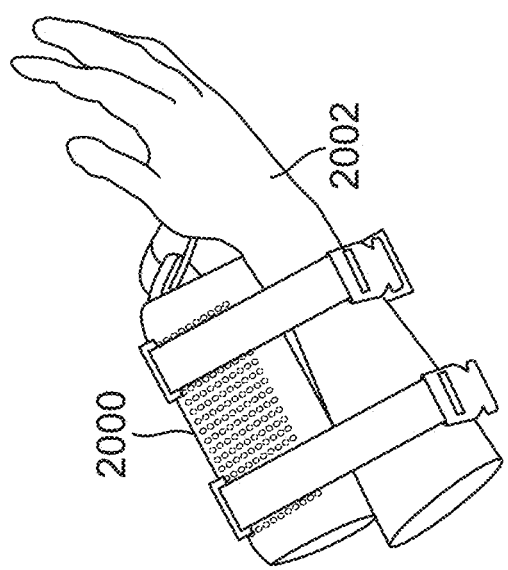

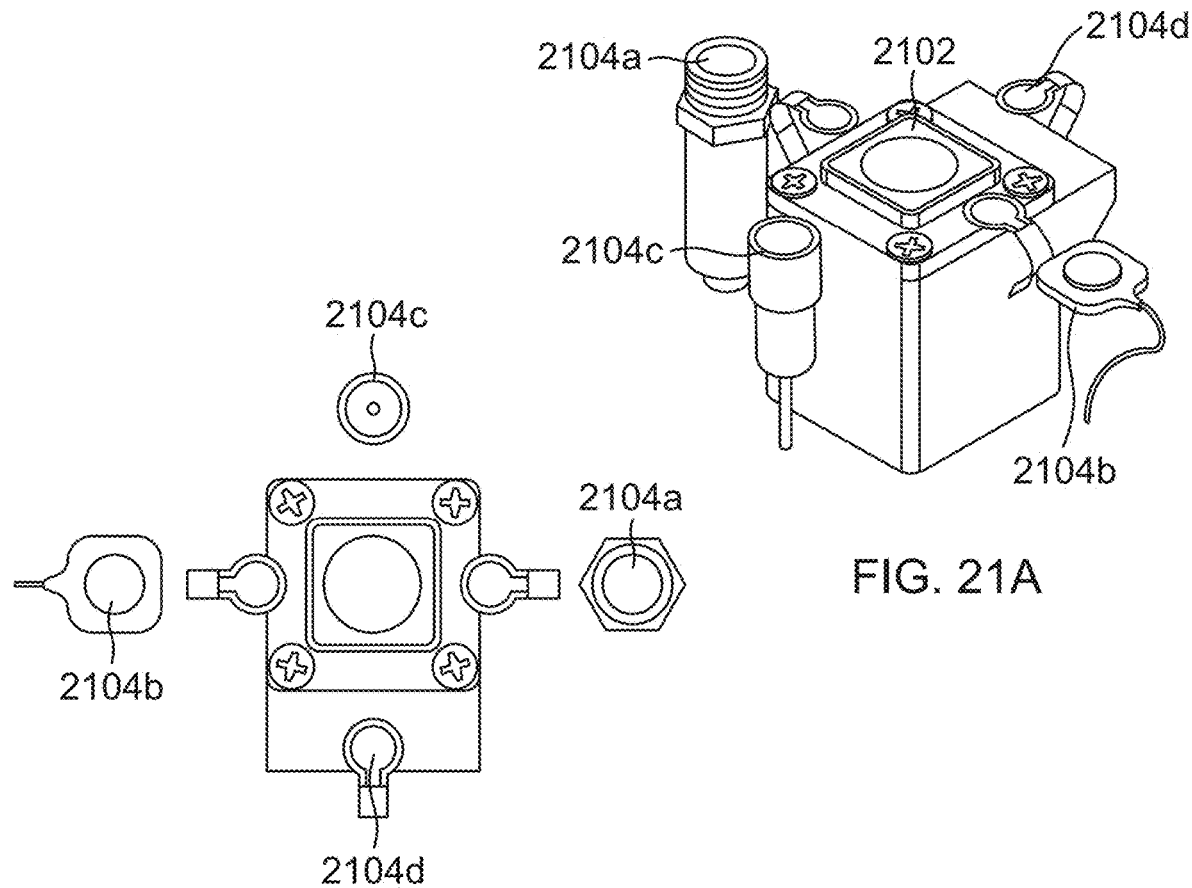
FIG. 21A
FIG. 21B
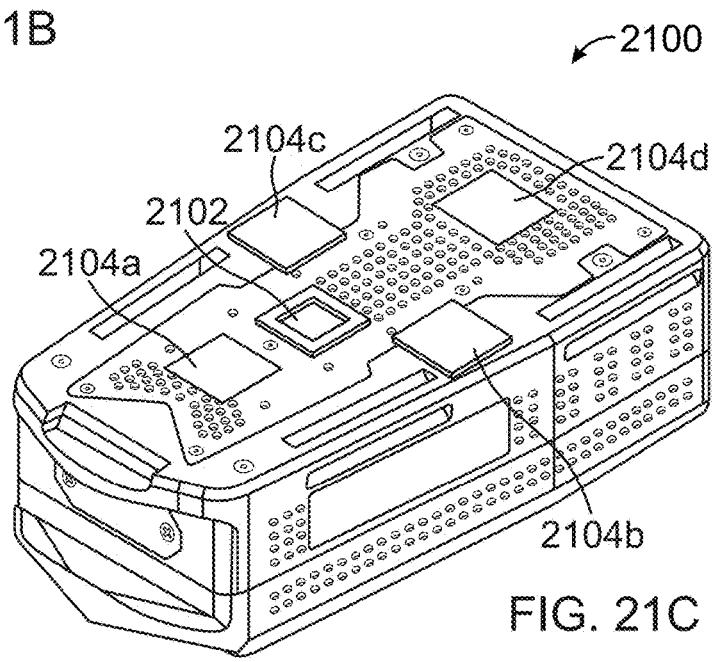
FIG. 21C

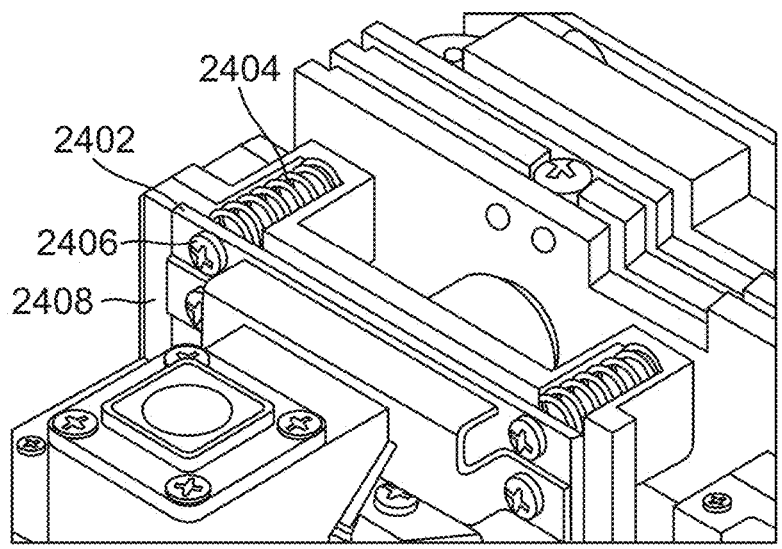
FIG. 24A
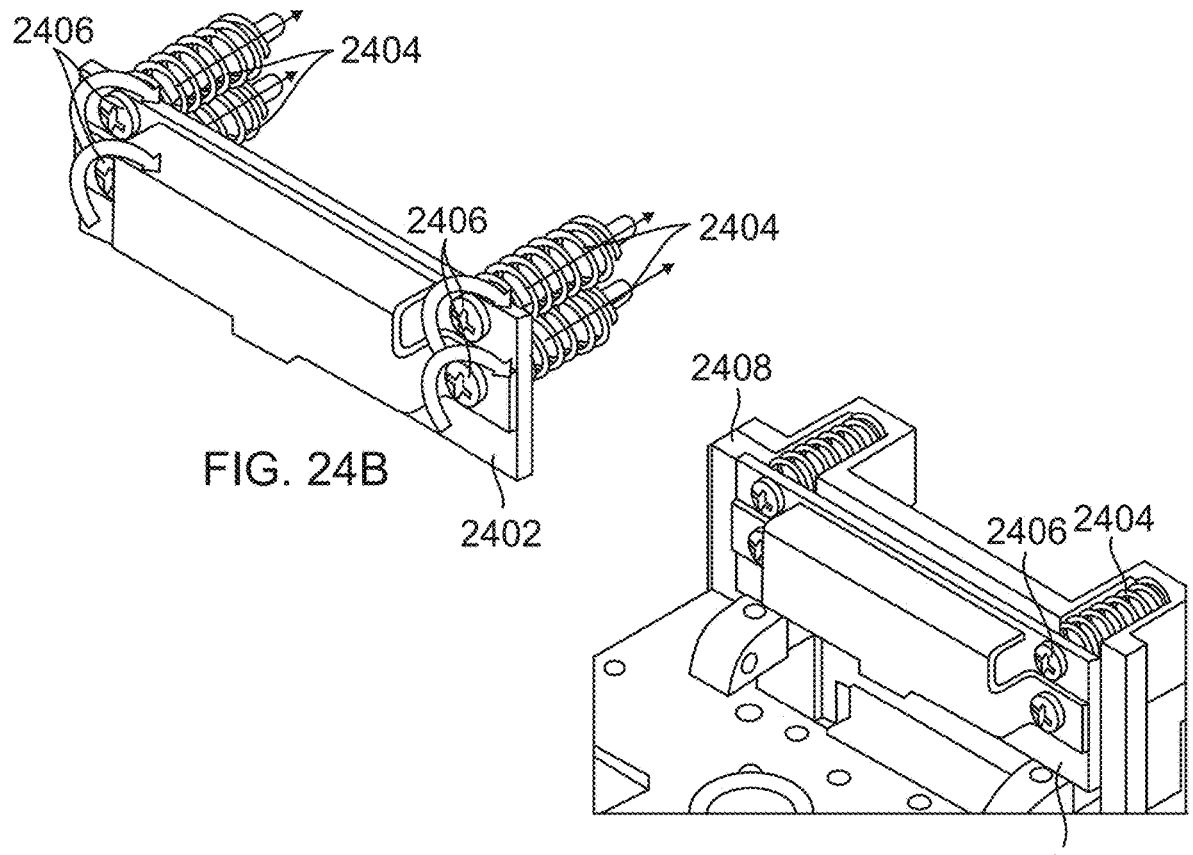
FIG. 24B
FIG. 24C

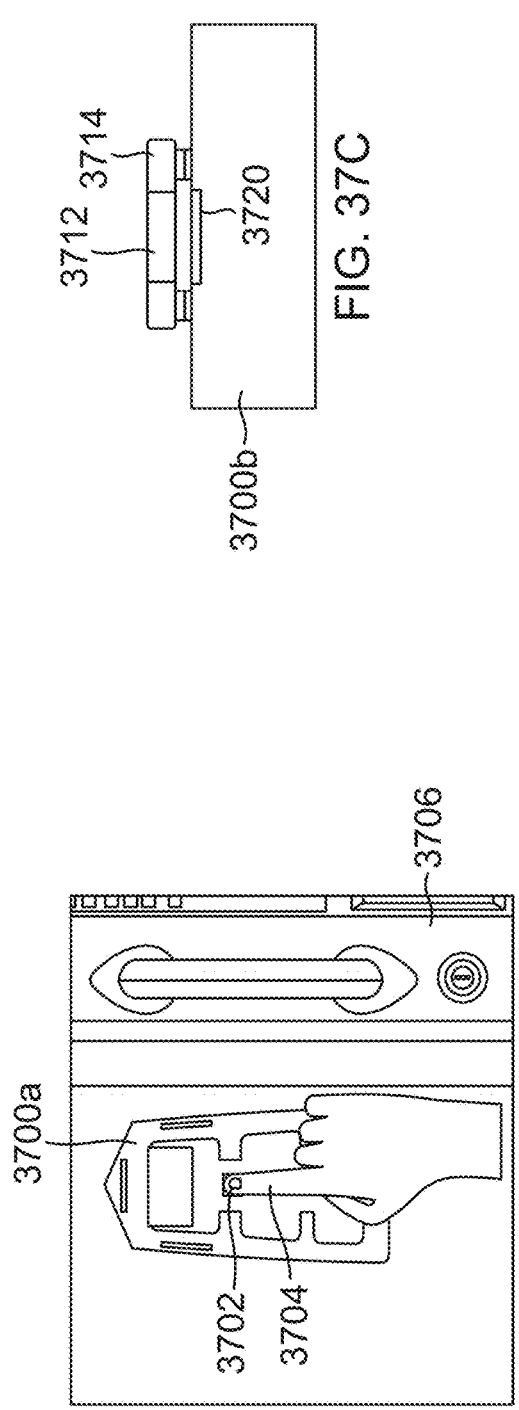

COMPACT SPECTRAL ANALYZER

PRIORITY CLAIM

This application claims priority to and the benefit of Provisional Application No. 63/227,284, filed in the U.S. Patent and Trademark Office on Jul. 29, 2021, the entire content of which is incorporated herein by reference as if fully set forth below in its entirety and for all applicable purposes.

TECHNICAL FIELD

The technology discussed below relates generally to a compact spectral analyzer, and in particular to a non-invasive biochemistry spectral analyzer that avoids heating the sample.

BACKGROUND

Non-invasive detection of biochemical materials and analytes has gained attention in the recent decades, including the in-vivo detection of glucose, alcohol, and cholesterol through skin measurements. Attention has been extended as well to the detection of skin cancer/tumor cells and skin diseases. Continuous monitoring of the critical human body analytes is crucial for saving lives, especially glucose, replacing the common non-continuous methods including time-consuming invasive lab chemistry blood analysis, and finger-prick glucometers.

Various solutions have been recently investigated and implemented. For example, minimally invasive Continuous Glucose Monitoring (CGM) is a solution currently available in the market. However, CGM suffers from a short lifetime of a few tens of days and requires frequent calibration with a finger-prick method. Implanted monitors have also been developed. However, these monitors face the complexity of foreign-body response. Non-invasive epidermal electrochemical solutions have targeted measuring biofluids including skin interstitial fluid and sweat, where the glucose concentration in blood correlates with that in these biofluids. However, relying on glucose concentration in biofluids suffers a lag behind the actual glucose level in blood, and the accuracy may be affected by the interaction between different fluids. Electrochemical methods may cause skin-irritation and suffer as well from reagent consumption limiting the lifetime of the device. Other methods include microwave/RF-based detection and bio-impedance-based detection. Non-invasive measurement of alcohol concentration in blood has also gained a lot of interest to reduce alcohol-related accidents and crimes.

Spectroscopy has also been proposed as a solution for non-invasive biochemistry analysis due to the robust material detection and quantification method employed. For example, spectroscopy-based solutions have been developed for measuring different analytes concentration in the skin biofluids and in the blood vessels inside the dermis. Different spectral sensors have been developed based on a fiber bundle to illuminate the sample and collect the reflected light, with an array of different-band laser sources and detectors, or all the illumination fibers coupled to the same light source, and the collection fibers are coupled to the spectrometer. However, special fiber-based solutions suffer from high cost and scalability issues.

Other free-space non-invasive solutions have been developed based on a monochromatic filter wheel architecture. In these architectures, light is transmitted through the filter wheel to the sample, with the sample being perpendicular to the light, and the diffuse-reflected light is collected from the sample by photodetectors arranged at the sides of the illumination beam. However, a more compact solution that may avoid the use of moving motors is needed.

SUMMARY

The following presents a summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a form as a prelude to the more detailed description that is presented later.

In an example, a spectral analyzer device is disclosed. The spectral analyzer includes an optical window configured to receive a sample and a spectral sensor. The spectral sensor includes a chassis having assembled thereto a light source configured to produce input light, an article having an aperture therein configured to receive the input light and further configured to pass a first portion of the input light and block a second portion of the input light, a light modulator configured to receive the first portion of the input light from the article and further configured to produce modulated light based on the first portion of the input light, an illumination optical element configured to direct the modulated light to the optical window for interaction with the sample to produce output light, a detector configured to produce an output signal based on the output light, a collection optical element configured to direct the output light to the detector, and a processor configured to process the output signal to produce spectral data representative of a spectrum of the sample. The spectral analyzer further includes a thermal separator positioned between the light modulator and the light source.

These and other aspects of the invention will become more fully understood upon a review of the detailed description, which follows. Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

BRIEF DESCRIPTION OF THE DRAWINGS

FIGS. 5A-5C are diagrams illustrating another example of a spectral sensor of a spectral analyzer according to some aspects.

FIG. 20A is a diagram illustrating an example wearable spectral analyzer according to some aspects.

FIGS. 20B-20D are diagrams illustrating an optical window of the spectral analyzer including microfluidic channels according to some aspects.

FIGS. 21A-21C are diagrams illustrating the integration of sensors within a spectral analyzer according to some aspects.

FIGS. 24A-24C are diagrams illustrating an example of optical alignment of a substrate of a light modulation chip of a spectral sensor according to some aspects.

FIGS. 37A-37C are diagrams illustrating example implementations of the spectral analyzer according to some aspects.

DETAILED DESCRIPTION

Figure 1:
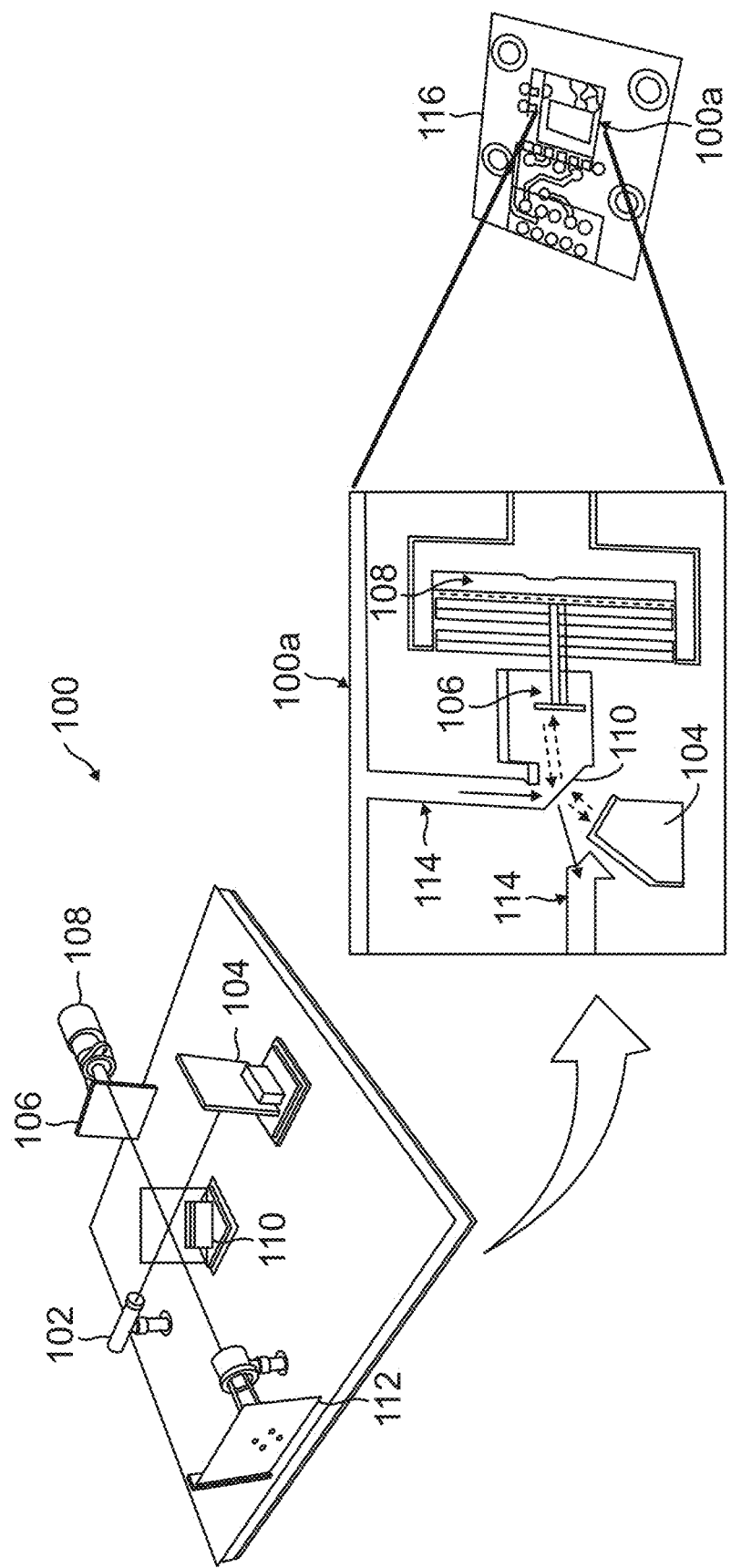
FIG. 1 is a diagram illustrating a spectrometer according to some aspects.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Various aspects of the disclosure relate to a non-invasive spectral analyzer for material analysis that includes a compact spectrometer (e.g., interferometer and detector). For example, the spectral analyzer can combine a micro-electromechanical systems (MEMS) based IR spectrometer and artificial intelligence (AI) engine used to interpret data measured by the spectrometer (e.g., a spectrum) and to map the data to, for example, a biochemical content concentration or analyte concentration, or virus positivity/negativity inside human skin or other biological tissue.

The spectral analyzer can include an optical window configured to receive a sample and a spectral sensor including the spectrometer. The AI engine may be implemented on the spectral analyzer or may be a cloud-based AI engine. The spectral sensor may include a light source, a light modulator (e.g., an interferometer), an illumination optical element, a collection optical element, a detector (e.g., a photodetector), and a processor arranged or assembled on a chassis. At least one aperture may be present in front of the light source to block non-useful rays, thus minimizing heat transfer to the remainder of the spectral sensor. For example, the light modulator may be implemented as a light modulation chip attached to a substrate (e.g., a daughter board). The substrate may have an aperture therethrough configured to pass a first portion of input light from the light source and to block a second portion (e.g., non-useful rays) of the input light. In some examples, the light source may include a light source cover having an aperture therein designed to block the non-useful rays. In addition, the cover aperture may further be optimized to match the input beam solid angle to a numerical aperture of the light modulation chip. In addition, a thermal separator may be included between the light source and the chassis for isolating the electronic aggressors from temperature-sensitive elements, such as the photodetector.

Thermal management may further be achieved by including a heatsink for the light source. In some examples, the photodetector can be thermally stabilized or cooled using a Peltier element and/or a fan.

A light coupling molded optics part can be attached to the light modulation chip (e.g., MEMS chip) to couple out-of-plane light to and from the light modulator, where the light propagates through the light modulator in-plane parallel to the MEMS chip substrate and the daughter board. The illumination optical element may include a light folding mirror to minimize the size of the spectral sensor. In addition, the collection optical element may include high numerical aperture lenses, such as aspherical lenses. In other examples, the collection optical element may include a non-imaging light concentrator to improve the coupling efficiency and reduce the absorption losses inside the lens materials. The concentrator element may further include an aperture that passes the light from the illumination optical element to the sample, blocking the non-useful stray light. Other features and implementations of the spectral analyzer are described below.

Non-invasive analysis can include skin detection, in addition to biological detection in human skin blood. This may include, for example, virus infection, bacterial infection, parasites infection, or their antibodies, in addition to others. In some examples, the spectral analyzer can detect the body biomarkers associated with a certain disease or type of infection. For example, the subject may place a fingertip on the optical window of the spectral analyzer or a cover slip on top of the optical window, and the reflectance spectra can be collected. The measurement location can be any spot on the body that maximizes the sensitivity and the specificity of the test. A solution can further support mass screening of subjects. Such a solution may be an efficient tool to contain the spread of an infection in a pandemic situation, for example COVID-19 by facilitating the mobility of human test subjects and assisting decision-makers to provide or prevent access to the test subjects.

FIG. 1 is a diagram illustrating a spectrometer 100 according to some aspects. The spectrometer 100 may be, for example, a Fourier Transform infrared (FTIR) spectrometer. In the example shown in FIG. 1, the spectrometer 100 includes a Michelson FTIR interferometer. In other examples, the spectrometer may include an FTIR Fabry-Perot interferometer.

FTIR spectrometers measure a single-beam spectrum (power spectral density (PSD)), where the intensity of the single-beam spectrum is proportional to the power of the radiation reaching the detector. In order to measure the absorbance of a sample, the background spectrum (i.e., the single-beam spectrum in absence of a sample) may first be measured to compensate for the instrument transfer function. The single-beam spectrum of light transmitted or reflected from the sample may then be measured. The absorbance of the sample may be calculated from the transmittance, reflectance, or trans-reflectance of the sample. For example, the absorbance of the sample may be calculated as the ratio of the spectrum of transmitted light, reflected light, or trans-reflected light from the sample to the background spectrum.

The spectrometer 100 includes a fixed mirror 104, a moveable mirror 106, a beam splitter 110, and a detector 112 (e.g., a photodetector). A light source 102 associated with the spectrometer 100 is configured to emit an input beam and to direct the input beam towards the beam splitter 110. The light source 102 may include, for example, a laser source, one or more wideband thermal radiation sources, or a quantum source with an array of light emitting devices that cover the wavelength range of interest.

The beam splitter 110 is configured to split the input beam into two beams. One beam is reflected off of the fixed mirror 104 back towards the beam splitter 110, while the other beam is reflected off of the moveable mirror 106 back towards the beam splitter 110. The moveable mirror 106 may be coupled to an actuator 108 to displace the movable mirror 106 to the desired position for reflection of the beam. An optical path length difference (OPD) is then created between the reflected beams that is substantially equal to twice the mirror 106 displacement. In some examples, the actuator 108 may include a micro-electro-mechanical systems (MEMS) actuator, a thermal actuator, or other type of actuator.

The reflected beams interfere at the beam splitter 110 to produce an output light beam, allowing the temporal coherence of the light to be measured at each different Optical Path Difference (OPD) offered by the moveable mirror 106. The signal corresponding to the output light beam may be detected and measured by the detector 112 at many discrete positions of the moveable mirror 106 to produce an interferogram. In some examples, the detector 112 may include a detector array or a single pixel detector. The interferogram data verses the OPD (e.g., an output signal) may then be input to a processor (not shown, for simplicity). The spectrum may then be retrieved, for example, using a Fourier transform carried out by the processor.

In some examples, the spectrometer 100 may include a MEMS interferometer 100a (e.g., a MEMS chip). The MEMS chip 100a may then be attached to a printed circuit board (PCB) 116 that may include, for example, one or more processors, memory devices, buses, and/or other components. In some examples, the PCB 116 may include a spectrum analyzer, such as an AI engine, configured to receive and process the spectrum. As used herein, the term MEMS refers to the integration of mechanical elements, sensors, actuators and electronics on a common silicon substrate through microfabrication technology. For example, the microelectronics are typically fabricated using an integrated circuit (IC) process, while the micromechanical components are fabricated using compatible micromachining processes that selectively etch away parts of the silicon wafer or add new structural layers to form the mechanical and electromechanical components. One example of a MEMS element is a micro-optical component having a dielectric or metallized surface working in a reflection or refraction mode. Other examples of MEMS elements include actuators, detector grooves and fiber grooves.

In the example shown in FIG. 1, the MEMS interferometer 100a may include the fixed mirror 104, moveable mirror 106, beam splitter 110, and MEMS actuator 108 for controlling the moveable mirror 106. In addition, the MEMS interferometer 100a may include fibers 114 for directing the input beam towards the beam splitter 110 and the output beam from the beam splitter 110 towards the detector (e.g., detector 112). In some examples, the MEMS interferometer 100a may be fabricated using a Deep Reactive Ion Etching (DRIE) process on a Silicon On Insulator (SOI) wafer in order to produce the micro-optical components and other MEMS elements that are able to process free-space optical beams propagating parallel to the SOI substrate. For example, the electro-mechanical designs may be printed on masks and the masks may be used to pattern the design over the silicon or SOI wafer by photolithography. The patterns may then be etched (e.g., by DRIE) using batch processes, and the resulting chips (e.g., MEMS chip 100a) may be diced and packaged (e.g., attached to the PCB 116).

For example, the beam splitter 110 may be a silicon/air interface beam splitter (e.g., a half-plane beam splitter) positioned at an angle (e.g., 45 degrees) from the input beam. The input beam may then be split into two beams L1 and L2, where L1 propagates in air towards the moveable mirror 106 and L2 propagates in silicon towards the fixed mirror 104. Here, L1 originates from the partial reflection of the input beam from the half-plane beam splitter 110, and thus has a reflection angle equal to the beam incidence angle. L2 originates from the partial transmission of the input beam through the half-plane beam splitter 110 and propagates in silicon at an angle determined by Snell's Law. In some examples, the fixed and moveable mirrors 104 and 106 are metallic mirrors, where selective metallization (e.g., using a shadow mask during a metallization step) is used to protect the beam splitter 110. In other examples, the mirrors 104 and 106 are vertical Bragg mirrors that can be realized using, for example, DRIE.

In some examples, the MEMS actuator 108 may be an electrostatic actuator formed of a comb drive and spring. For example, by applying a voltage to the comb drive, a potential difference results across the actuator 108, which induces a capacitance therein, causing a driving force to be generated as well as a restoring force from the spring, thereby causing a displacement of moveable mirror 106 to the desired position for reflection of the beam back towards the beam splitter 110.

The unique information from the vibrational absorption bands of a molecule are reflected in an infrared spectrum that may be produced, for example, by the spectrometer 100 shown in FIG. 1. By applying spectral numerical processing and statistical analysis to a spectrum, the information in the spectrum may be identified or otherwise classified. The application of statistical methods to the analysis of experimental data is traditionally known as chemometrics, and more recently as artificial intelligence.

Figure 2:
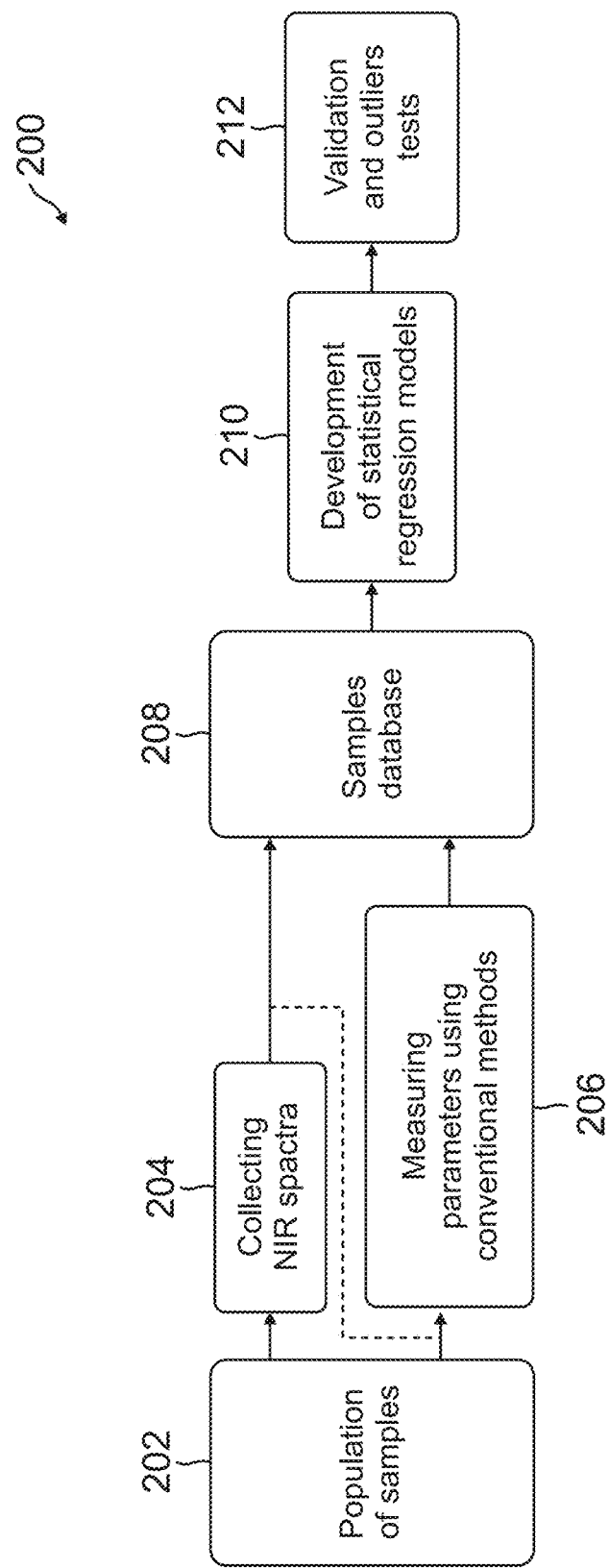
FIG. 2 illustrates an example of a workflow for building an AI engine according to some aspects.

FIG. 2 illustrates an example of a workflow 200 for building an AI engine according to some aspects. To begin building the AI engine, a group or population of samples 202 is obtained for measurements by a spectrometer, such as the spectrometer 100 shown in FIG. 1, to produce spectra 204. At the same time, these samples 202 can also be measured by conventional methods and the values recorded as reference values 206. These reference values 206 together with the spectra 204 form a samples database 208 that is used to teach the AI engine (e.g., machine learning) how to interpret the spectra and transform the spectra to certain values (e.g., results). For example, the samples database 208 may be used in the development of statistical regression models (e.g., calibration models) 210 that may then be applied to a spectrum of a sample to produce a result (e.g., a positive or negative test result or antibody level) associated with the sample. Validation and outliers detection 212 of the test results may then be performed to refine the calibration model(s).

Since the spectrum produced by infrared (IR) spectroscopy are instantaneous, unlike conventional analysis methods, there is no need to wait for certain transformations (e.g., chemical transformations) to occur within the sample. Different physical and chemical parameters of the sample can be analyzed with a single scan.

Figure 3:
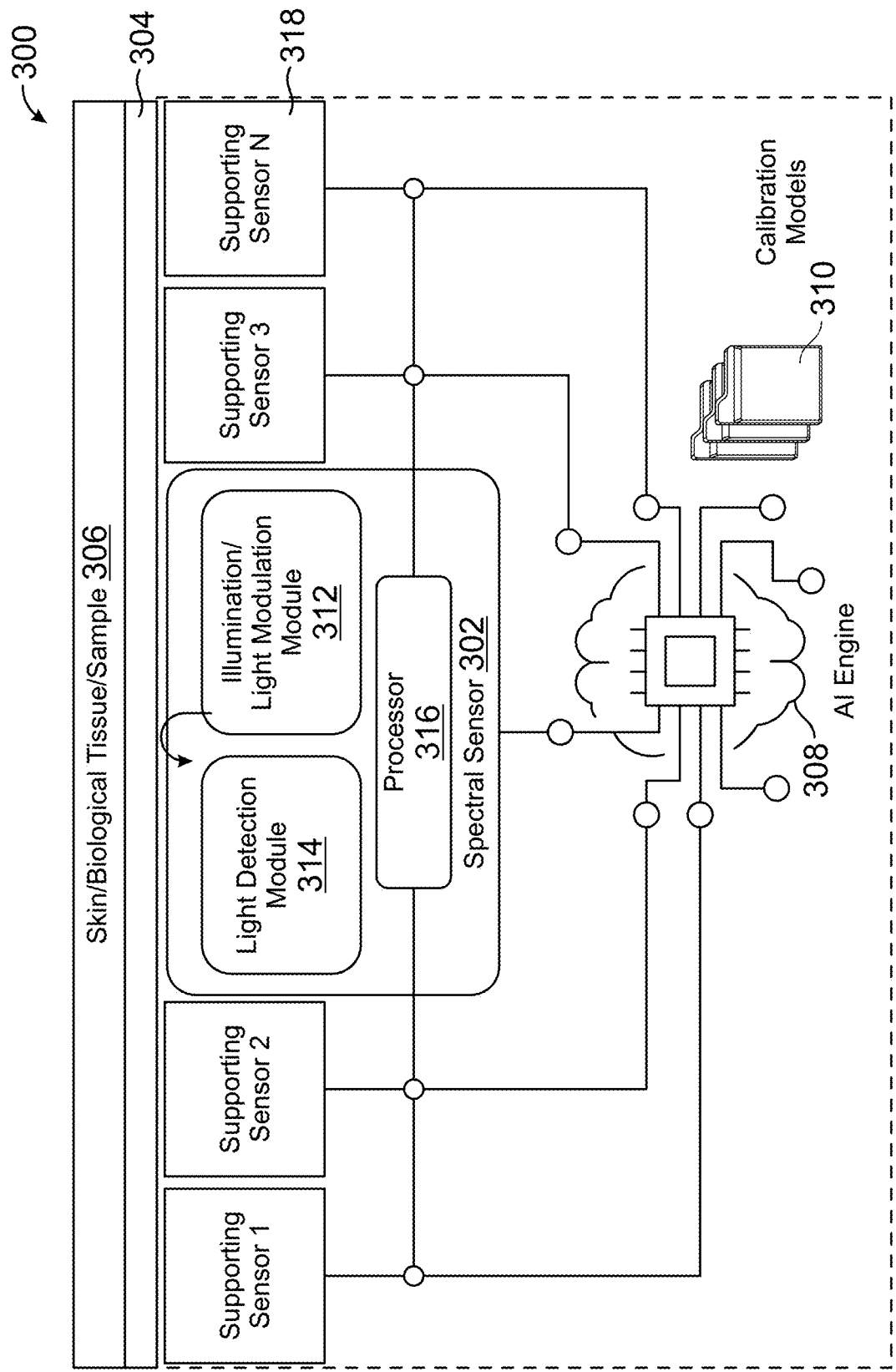
FIG. 3 is a diagram illustrating an example of a spectral analyzer according to some aspects.

FIG. 3 is a diagram illustrating an example of a spectral analyzer 300 according to some aspects. The spectral analyzer 300 shown in FIG. 3 is a compact spectral analyzer that may be used, for example, for biochemistry and biological analyte detection. The spectral analyzer 300 includes a spectral sensor 302, an optical window 304 configured to receive a sample 306 (e.g., skin or other biological tissue sample), and an artificial intelligence (AI) engine 308. The analysis of the biological sample (e.g., sample 306) may be performed in-vitro or in-vivo.

The AI engine 308 can include or may access, for example, one or more calibration models 310, each built for a respective type of analyte under test. In some examples, the calibration models 310 can include generic global models for all users or one or more calibration models 310 can be customized and specific per person. For example, a fingerprint or identity sensor or Iris recognition system can be used to identify a user to enable the AI engine 308 to retrieve the correct calibration model 310. In other examples, the spectral analyzer 300 may be in wireless communication with a user's cell phone (or other personal device), and an application on the user's device can validate the identity of the user (e.g., using a password, pattern lock, camera, etc.) for the AI engine 308 to retrieve the calibration model 310 associated with the user. In other examples, the spectral analyzer may be connected to (e.g., wired connection or wireless connection) a camera used to capture the user's face and prove the identity of the user.

The spectral sensor 302 includes an illumination/light modulation module 312, a light detection module 314, and a processor 316. The processor 316 may include a single processing device or a plurality of processing devices. Such a processing device may be a microprocessor, micro-controller, digital signal processor, microcomputer, central processing unit, field programmable gate array, programmable logic device, logic circuitry, analog circuitry, digital circuitry, and/or any device that manipulates signals (analog and/or digital) based on hard coding of the circuitry and/or operational instructions. The processor 316 may be coupled to a memory (not shown). The memory may be a single memory device, a plurality of memory devices, and/or embedded circuitry of the processor 316. Such a memory device may be a read-only memory, random access memory, volatile memory, non-volatile memory, static memory, dynamic memory, flash memory, cache memory, and/or any device that stores digital information, including instructions (e.g., code) that may be executed by the processor 316.

The illumination/light modulation module 312 may include, for example, at least one light source, a light modulator (e.g., an interferometer that may be implemented within a light modulation chip), and one or more illumination optical elements. The light detection module 314 may include, for example, one or more collection optical elements and a detector. The light modulator may use a spectroscopic technique, including, but not limited to, direct absorption spectroscopy, indirect absorption spectroscopy, such as photo-acoustic spectroscopy, photo-thermal spectroscopy, or Raman spectroscopy. In some examples, the light modulator may include a diffraction element, a Michelson interferometer, a Fabry-Perot cavity, a spatial light modulator, or a birefringent device. For example, the light modulator may include includes a MEMS interference device, such as the MEMS FTIR based spectrometer, as shown in FIG. 1. The MEMS interferometer enables generating a spectrum in millisecond time scale since the moving micromirror is driven by a MEMS actuator.

The light source(s) may include, for example, a laser source or wideband source. In some examples, the light source(s) may be infrared or near-infrared light source(s). The light source may produce radiation with high power that cannot be shined directly on the sample. As such, the input light produced by the light source may be first passed through the light modulator such that the power of the modulated light output from the light modulator is safe to be shined on the sample (e.g., the power of the modulated light is less than a threshold). The reduction (e.g., attenuation) in power introduced by the light modulator may be in the form of absorption of an amount of the electromagnetic radiation, converting the absorbed amount into heat energy that can be dissipated without harming the sample. The reduction can also be in the form of selection of certain wavelengths to be transmitted and shined on the sample. The reduction can further be in the form of diffraction losses or optical throughput (etendue) losses in the light modulation chip.

The light detection module 314 in combination with the processor 316 may be configured to obtain a spectrum of the sample 306 and to provide the spectrum (e.g., spectral data) to the AI engine 308 for analysis and processing. The AI engine 308 is configured to process the spectrum to generate a result indicative of at least one parameter associated with the sample 306 from the spectrum. In some examples, the result may be utilized as a decision-making mechanism or to trigger an action allowing or preventing mobility of a subject (e.g., authorize or prevent access of the tested subject to a facility or through a gate or enable operation by the subject of a motorized vehicle). For example, the AI engine 308 may include one or more processors for processing the spectrum and a memory configured to store the calibration models 310 utilized by the processor in processing the spectrum. The AI engine 308 can be embedded within the spectral analyzer 300 (as shown in FIG. 3) or can be implemented as a cloud-based AI engine, connecting to the spectral analyzer 300 through a host device, such as a cell phone, tablet, laptop, PC, or other type of communication device.

The spectral analyzer 300 may further include optional supporting sensors 318 (e.g., Supporting Sensor 1, Supporting Sensor 2, . . . , Supporting Sensor N) assisting the AI engine 308. The sensors 318 may be, for example, physical or chemical sensors. Examples of sensors 318 may include, but are not limited to, a temperature sensor, a pressure sensor, a bio-impedance sensor, a hydration sensor, a heart rate sensor, an ECG sensor, a blood pressure sensor, a fingerprint sensor, and an imaging sensor. In some examples, the sensor data produced by the sensor(s) 318 may be used by the AI engine 308 to compensate for background variations that do not correlate with the chemical content or analyte of interest. In some examples, the sensor(s) 318 may be integrated on a surface of the spectral analyzer 300 in contact with the sample or skin.

Figure 4:
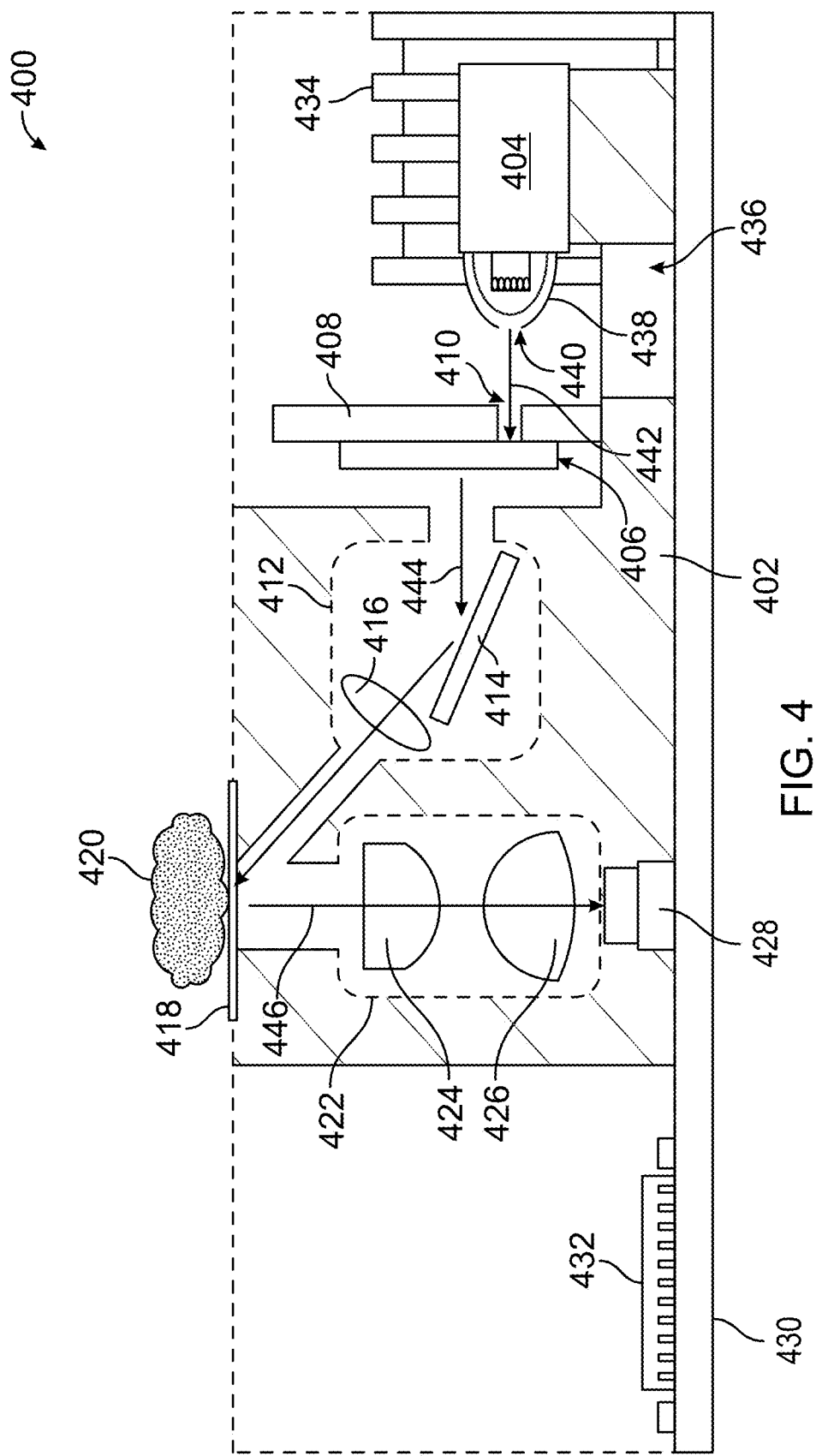
FIG. 4 is a diagram illustrating an example of a spectral sensor of a spectral analyzer according to some aspects.

FIG. 4 is a diagram illustrating an example of a spectral sensor 400 of a spectral analyzer according to some aspects. The spectral sensor 400 includes a chassis 402 that is configured to both align and connect together various components. For example, the components may be assembled on or attached to the chassis 402. The components can include, for example, a light source 404, a light modulator 406, illumination optical element(s) 412, collection optical element(s) 422, and a detector 428. An optical window 418 is positioned on a top surface of the spectral sensor 400 and is configured to receive a sample 420 (e.g., a biological sample) on an external surface thereof. In some examples, the light modulator 406 may include a MEMS interference device, such as the MEMS FTIR based light modulator, as shown in FIG. 1.

In the example shown in FIG. 4, the light modulator 406 is implemented on a light modulation chip (e.g., a MEMS chip). The light modulation chip is shown attached to a first side of a substrate 408 (e.g., a daughter board or chip carrier) opposite a second side of the substrate 408 adjacent the light source 404. The daughter board 408 is assembled on the chassis 402 and provides a connection between the light modulation chip 406 and an optional main substrate (e.g., an electronic board substrate or mother board) 430. In some examples, the mother board 430 includes a processor 432 (e.g., one or more processors and/or control circuitry) configured to control the light modulator 406 (e.g., via the daughter board 408) and the detector 428. In addition, the detector 428 may further be attached to the mother board 430. It should be understood that the configuration of the light source 404, light modulator 406, and detector shown in FIG. 4 are merely exemplary and other configurations may be possible.

In an example operation of the spectral sensor 400, the light source 404 may be configured to produce input light 442. An aperture (e.g., aperture 410 or 440) may be configured in front of the light source 404 to minimize stray light (e.g., block non-useful rays) of the input light 442, thereby reducing the amount of heat transferred to the remainder of the spectral sensor 400 (e.g., the light modulator 406, optical window 418 containing the sample 420, and detector 428). For example, the aperture (e.g., a hole) may be formed in an article, where the article may correspond to the daughter board 408 and/or a source cover 438 positioned on the light source 404. In some examples, the source cover 438 may not be present, and the aperture 410 (e.g., hole) in the daughter board 408 is configured to block the non-useful rays of input light 442. In other examples, the source cover 438 may be present and the aperture 440 (e.g., hole) in the source cover 438 is configured to block the non-useful rays of input light 442. In still other examples, both the source cover 438 and the daughter board 408 are present and each has a respective aperture 440 and 410 configured to collectively block the non-useful rays of input light 442. In this example, the light source 404 may be configured to generate incident light and the aperture 440 in the source cover 438 may be configured to block a portion of the incident light to produce the input light 442. The aperture 410 in the daughter board 408 may then be configured to block a portion of the input light 442 from reaching the light modulator (e.g., light modulation chip) 406.

Thus, one or more of the apertures 410 and 440 may have a size and shape configured to pass a first portion of the input light 442 and block a second portion of the input light 442 corresponding to the non-useful rays. One or more of the apertures 410 and 440 may further be designed to match the beam solid angle of the input light 442 to the effective numerical aperture of the light modulation chip.

The light modulator 406 is configured to receive the first portion of the input light 442 passed by the aperture(s) 410 and/or 440 and to produce modulated light 444 based on the input light 442. The modulated light 444 may then be directed by the illumination optical element(s) 412 to the optical window 518 for interaction with the sample 420 to produce output light 446 (e.g., reflected scattered light) in a reflection mode. The sample 420 is arranged to be on the upper (top) side of the spectral sensor 400 and translated away from the light source 404, which is attached to the backside of the spectral sensor 400, to prevent heating of the sample 420 from the light source 404. This separation and translation of the sample 420 with respect to the light source 404 is beneficial when the light source 404 is based on the black body radiation and the source temperature is high so as to produce high radiation power.

In the example shown in FIG. 4, the illumination optical element(s) 412 includes a redirecting mirror (e.g., a folding mirror) 414 and a focusing lens 416. The redirecting mirror 414 is configured to direct the modulated light 444 towards the optical window 418 through the focusing lens 416. In some examples, the focusing lens 416 may be configured to focus the modulated light 444 inside the sample 420 at a certain depth or directly at the top surface of the optical window 418, depending on the type of sample 420. It should be understood that the illumination optical element(s) 412 shown in FIG. 4 are merely exemplary and other illumination optical elements may be used instead of or in addition to those shown in FIG. 4.

The reflected light (e.g., output light 446) from the sample 420 is coupled back to the spectral sensor 400 through the optical window 418 and then coupled back to the detector 428 using the collection optical element(s) 422. The detector 428 may be configured to produce an output signal based on the output light 446. The processor 432 may be configured to process the output signal to produce spectral data representative of a spectrum of the sample 420. In the example shown in FIG. 4, the collection optical element(s) 422 include a set of at least two lenses 424 and 426. The lenses 424 and 426 may form, for example, a two-lens system for 1:1 coupling or imaging of the reflected light 446 from the sample 420 onto the detector 428 (e.g., a photodetector). The two-lens system may be used, for example, to collimate the reflected light 446. In some examples, the lenses 424 and 426 may be aspheric lenses, ball lenses, or Fresnel lenses.

In some examples, at least the collection optical element(s) 422 may be incorporated into an optics block that may be attached to the chassis 402. For example, at least the collection optical elements 422 may be fabricated within the optics block. In an example, the collection optical elements 422 and the focusing lens 416 may be incorporated in the optics block. In another example, the collection optical elements 422 and the illumination optical elements 412 may be incorporated into the optics block. In some examples, the optical window 418 may be positioned on a top surface of the optics block and aligned with the collection optical elements 422 and detector 428. In some examples, an optical fiber may instead be used to deliver the modulated light 444 to the sample 420. For example, a multi-mode optical fiber (MMF) for illumination and free-space optics may be used for illumination of the sample. In an example, an optical fiber tilted with an angle, for example 45°, may be used for illumination of the sample 420. A MMF may further be used for collection of the reflected light 446.

In examples in which the AI engine is incorporated into the spectral analyzer, the processor 432 may include the AI engine logic, and thus be configured to receive spectral data (e.g., the spectrum or other spectral data obtained from the spectrum) to generate a result indicative of at least one parameter associated with the sample 420 based on the spectral data. In other examples, the AI engine may be implemented on a different device within the spectral analyzer or may be a cloud-based AI engine in communication with the spectral analyzer to receive the spectral data and generate the result therefrom.

The spectral sensor 400 may optionally further include a heat sink 434 coupled to the light source 404 and attached to the chassis 402. The heat sink 434 is configured to remove heat from the light source 404 to further protect the other spectral sensor components and the sample 420 from heating. In addition, a thermal separator 436 may optionally be attached between the light modulator 406 (e.g., the daughter board 408 carrying the light modulator 406) and the light source 404. The thermal separator 436 is configured to thermally insulate the mother board 430 and daughter board 408 from the light source 404, thus further isolating the light source 404 from temperature-sensitive components, such as the detector 428.

FIGS. 5A-5C are diagrams illustrating another example of a spectral sensor 500 of a spectral analyzer according to some aspects. FIG. 5A is a side view of the spectral sensor 500, while FIGS. 5B and 5C are perspective views of the spectral sensor 500. In the example shown in FIGS. 5A-5C, the spectral sensor 500 includes a chassis 502 that is configured to both align and connect together various components, such as a light source 504, a light modulator 506 (e.g., a light modulation chip including the light modulator), illumination optical element(s) 512, collection optical element(s) 522, and a detector 528. An optical window 518 is shown positioned on a top surface of the spectral sensor 500 and is configured to receive a sample 520 (e.g., a biological sample) on an external surface thereof.

A substrate (e.g., an electronic board substrate or mother board) 530 may be attached to the chassis 502. The light modulation chip including the light modulator 506 is shown attached to a first side of an additional substrate 508 (e.g., a daughter board or chip carrier) opposite a second side of the substrate 508 adjacent the light source 504. The daughter board 508 is assembled on the chassis 502 and includes an aperture 510 configured to pass a first portion of light emitted from the light source 504 and to block a second portion of the light (e.g., light corresponding to non-useful rays). The daughter board 508 may provide a connection between the light modulation chip 506 and the mother board 530. The detector 528 may further be attached to the mother board 530. The illumination optical element(s) 512 may include a redirecting mirror (e.g., a folding mirror) 514 and a focusing lens 516, similar to that shown in FIG. 4. In addition, the collection optical element(s) 522 may include a pair of lenses 524 and 526, similar to that shown in FIG. 4.

In the example shown in FIGS. 5A-5C, a heat sink 532 is formed as part of the chassis 502. Thus, the chassis 502 further operates as a heat sink 532 for the light source 504 to protect the other spectral sensor components and the sample 520 from heating. In some examples, the heat sink 532 forms a light source housing (e.g., a light source module) within which the light source 504 may be inserted. In addition, as shown in FIG. 5C, a fan 534 may be attached to the light source housing to remove heat from the light source housing/heat sink 532.

Figure 6:
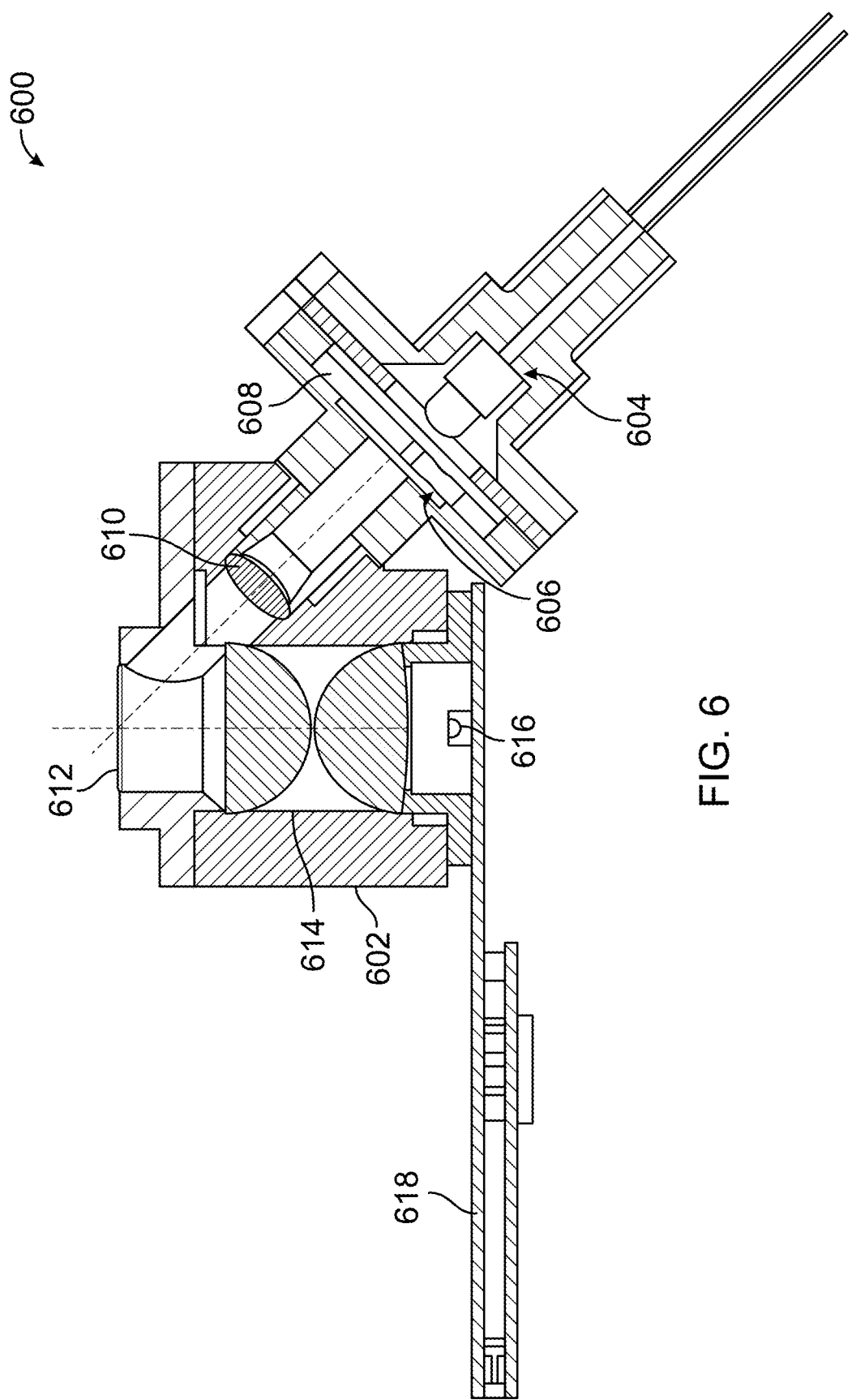
FIG. 6 is a diagram illustrating another example of a spectral sensor of a spectral analyzer according to some aspects.

FIG. 6 is a diagram illustrating another example of a spectral sensor 600 of a spectral analyzer according to some aspects. The spectral sensor 600 includes a chassis 602 that is configured to both align and connect together various components, such as a light source 604, a light modulator 606 (e.g., a light modulation chip including the light modulator), illumination optical element(s) 610, collection optical element(s) 614, and a detector 616. An optical window 612 is shown positioned on a top surface of the spectral sensor 600 and is configured to receive a sample (not shown) on an external surface thereof.

A substrate (e.g., an electronic board substrate or motherboard) 618 may be attached to the chassis 602. The light modulation chip including the light modulator 606 is shown attached to an additional substrate 608 (e.g., a daughter board or chip carrier). In the example shown in FIG. 6, the illumination optical element(s) 610 include a focusing lens without the use of a folding or redirecting mirror to redirect the light towards the optical window 612. Therefore, in this example, the light source 604, daughter board 608, and light modulation chip 606 are rotated such that their optical axes are aligned with the optical axis of the illumination focusing lens 610, which is further aligned with the direction of incidence on the sample. In some examples, the light source 604, light modulation chip 606 and daughter board 608 may be assembled together with the illumination focusing lens 610 in a single block or package, which may be attached to the chassis 620.

Figure 7A:
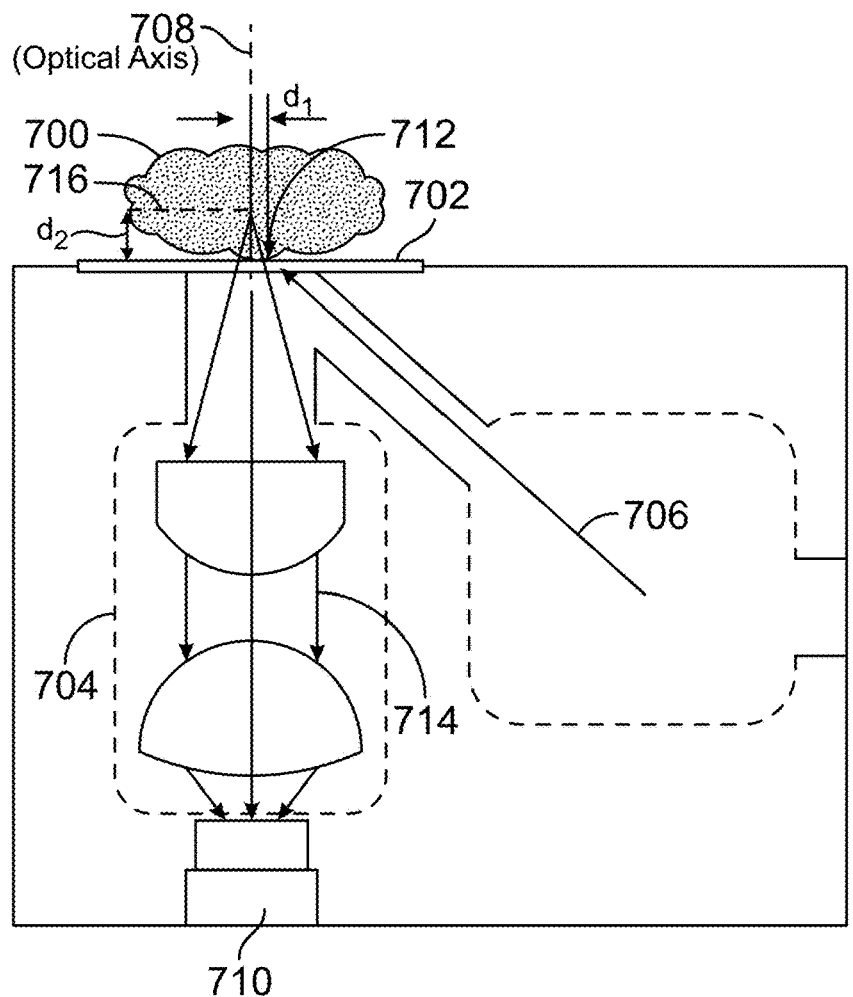
FIG. 7A is a diagram illustrating illumination of a sample in a spectral analyzer according to some aspects.

FIG. 7A is a diagram illustrating illumination of a sample in a spectral analyzer according to some aspects. In the example shown in FIG. 7A, a sample 700 is positioned on an external surface of an optical window 702 of the spectral analyzer. Modulated light 706 (e.g., produced by a light modulator) is directed towards the sample 700 through the optical window 702 via one or more illumination optical elements (not shown, for simplicity). The modulated light interacts with the sample 700 and the resulting output light 714 is directed to a detector 710 via collection optical element(s) 704 (e.g., a two-lens system).

As shown in FIG. 7A, at least one of the illumination/light modulation module (e.g., illumination optical element(s) and light modulator) and the light detection module (e.g., collection optical element(s) 704 and detector 710) may each be positioned to achieve a horizontal shift d1 between an intersection of the modulated light 706 with a sample interface (e.g., an interface between the sample 700 and the optical window 702) and an optical axis 708 of the light detection module. For example, the light detection module may be configured such that the optical axis 708 of the light detection module is displaced by a first distance d1 from the intersection of the modulated light 706 and the optical window 702 (e.g., sample interface at the optical window).

In addition, the direction and angle of incidence produced by the illumination optical system may be configured to further achieve a vertical shift d2 between an imaging plane 716 of the light detection module (e.g., the collection optical element(s) 704 and the detector 710) and the sample interface. For example, an imaging plane 716 of the light detection module may be displaced from the optical window 702 (e.g., the sample interface at the optical window) by a second distance d2.

Figure 7B:
FIG. 7B is a diagram illustrating the effect on the collected light histogram versus depth according to some aspects.

The two distances d1 and d2 may be designed to maximize the illumination of a layer deep in the sample 700, instead of at the sample shallow surface, thus maximizing the collection of output (e.g., reflected) light 714 from deep layers within the sample 700. Thus, the first and second distances d1 and d2 may be configured to enable illumination of a layer within the sample 700 (e.g., at the imaging plane 716) that is separated from a surface layer of the sample adjacent the optical window 702 (e.g., the sample interface layer). FIG. 7B is a diagram illustrating the effect on the collected light histogram versus depth. For each set of d1 and d2, the histogram centroid is shifted and its width or skewness is modified.

Figure 8A:
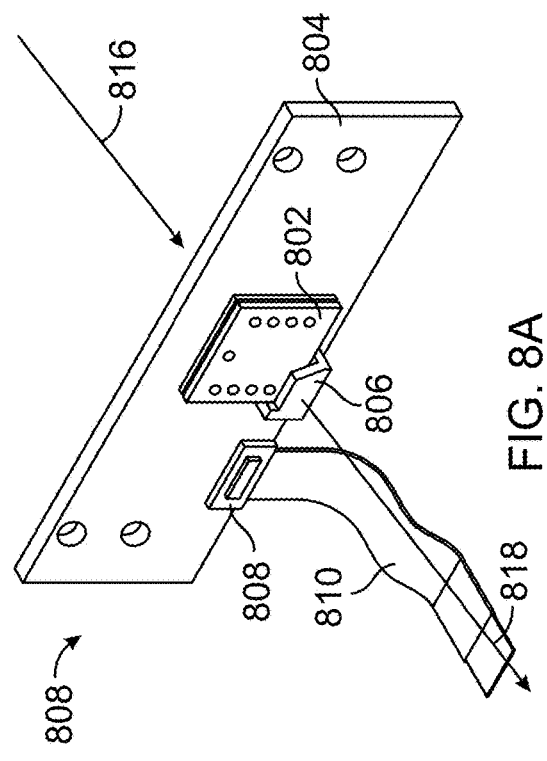
FIGS. 8A-8C are diagrams illustrating an example of a light modulation chip according to some aspects.
Figure 8C:
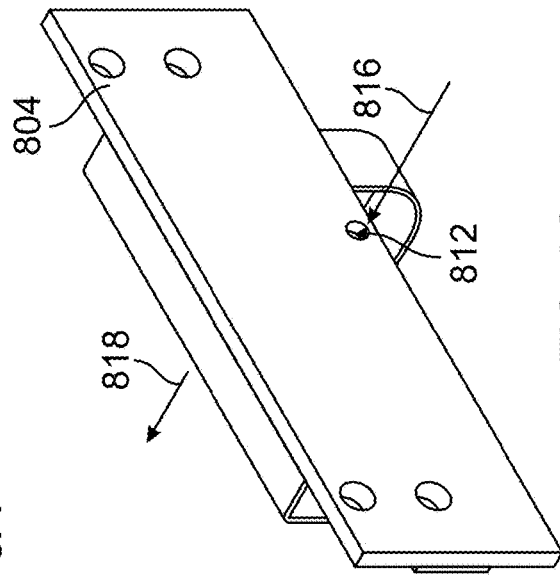
Figure 8B:
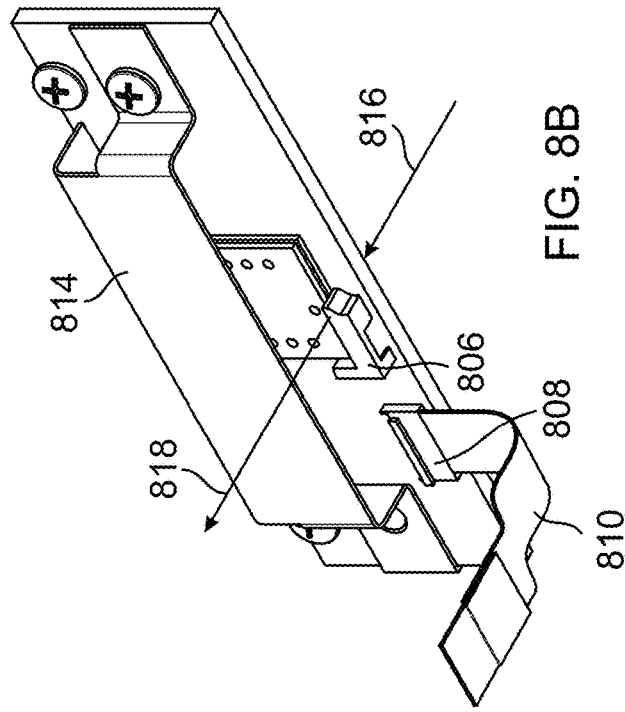

FIGS. 8A-8C are diagrams illustrating an example of a light modulation chip 802 according to some aspects. The light modulation chip 802 includes a light modulator (e.g., an FT-IR interferometer). In some examples, the light modulation chip 802 may be a MEMS chip. The light modulation chip 802 is attached to a daughter board 804 on a first side thereof. For example, the light modulation chip 802 may be attached to the daughter board 804 using a die attach epoxy at the backside of the chip 802, while the electrical connectivity of the actuator terminals may be implemented via wire bonds between light modulation chip pads and the daughter board pads surrounding the chip. A light coupling molded optics part 806 can be attached to the light modulation chip 802 to couple out-of-plane light 816 and 818 to and from the light modulator, where the light propagates through the light modulator interferometer in-plane parallel to the light modulation chip substrate 802 and the daughter board 804. An aperture 812 (e.g., hole) is formed in the daughter board 804 beneath the molded optics part 806 to couple the light 816 from the light source (not shown) to the light modulator. The daughter board 804 further includes an electrical connector 808 that can support a flex cable 810 for flexible connectivity between the daughter board 804 and the main/mother electronic board (not shown). A protection cover 814 can further be added above the light modulation chip 802 to block the stray light and to protect the wire bonds during assembly.

Figure 9:
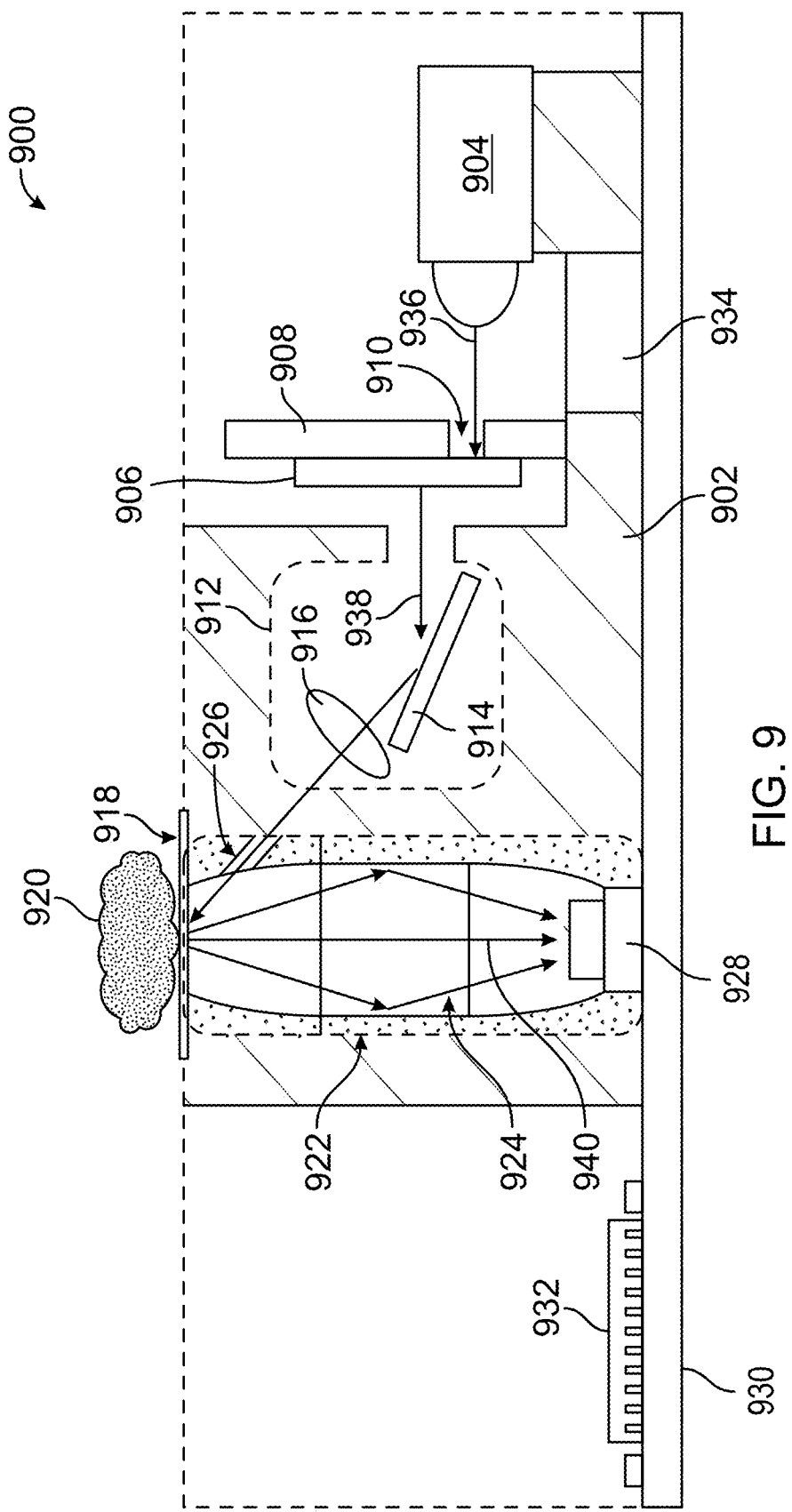
FIG. 9 is a diagram illustrating an example of a spectral sensor of a spectral analyzer operating in reflection mode according to some aspects.

FIG. 9 is a diagram illustrating an example of a spectral sensor 900 of a spectral analyzer operating in a reflection mode according to some aspects. The spectral sensor 900 includes a chassis 902 that is configured to both align and connect together various components, such as a light source 904, a light modulator 906 (e.g., a light modulation chip including the light modulator), illumination optical element(s) 912, collection optical element(s) 922, and a detector 928. An optical window 918 is shown positioned on a top surface of the spectral sensor 900 and is configured to receive a sample 920 (e.g., a biological sample) on an external surface thereof.

A substrate (e.g., an electronic board substrate or mother board) 930 may be attached to the chassis 902. The mother board 930 may include the detector 928 and processor 932 thereon. The processor 932 may be configured to control the light modulator 906 and the detector 928. The light modulation chip including the light modulator 906 is shown attached to a first side of an additional substrate 908 (e.g., a daughter board or chip carrier) opposite a second side of the substrate 908 adjacent the light source 904. The daughter board 908 is assembled on the chassis 902 and includes an aperture 910 configured to pass a first portion of input light 936 emitted from the light source 904 and to block a second portion of the input light (e.g., light corresponding to non-useful rays). The daughter board 908 may provide a connection between the light modulation chip 906 and the mother board 930. The illumination optical element(s) 912 may include a redirecting mirror (e.g., a folding mirror) 914 and a focusing lens 916, similar to that shown in FIGS. 4 and 5A-5C.

The light modulator 906 is configured to receive the first portion of the input light 936 passed by the aperture 910 of the daughter board 908 and to produce modulated light 938 based on the input light 936. The modulated light 938 may then be directed by the illumination optical element(s) 912 (e.g., redirecting mirror 914 and focusing lens 916) to the optical window 918 for interaction with the sample 920 to produce output light 940 in a reflection mode.

In the example shown in FIG. 9, the collection optical element(s) 922 includes a parabolic/elliptical concentrator element 924 to improve the coupling efficiency and reduce the absorption losses inside the lens materials. The concentrator element 924 includes an aperture 926 that is configured to pass the modulated light 938 from the illumination optical element(s) 912 to the sample 920. In some examples, the aperture 926 may further be configured to minimize the stray light that is not properly modulated.

In addition, a thermal separator 934 may optionally be attached between the chassis 902 and the light source 904. The thermal separator 934 is configured to thermally insulate the mother board 930 and daughter board 908 from the light source 904, thus isolating the light source 904 from temperature-sensitive components, such as the detector 928.

Figure 10:
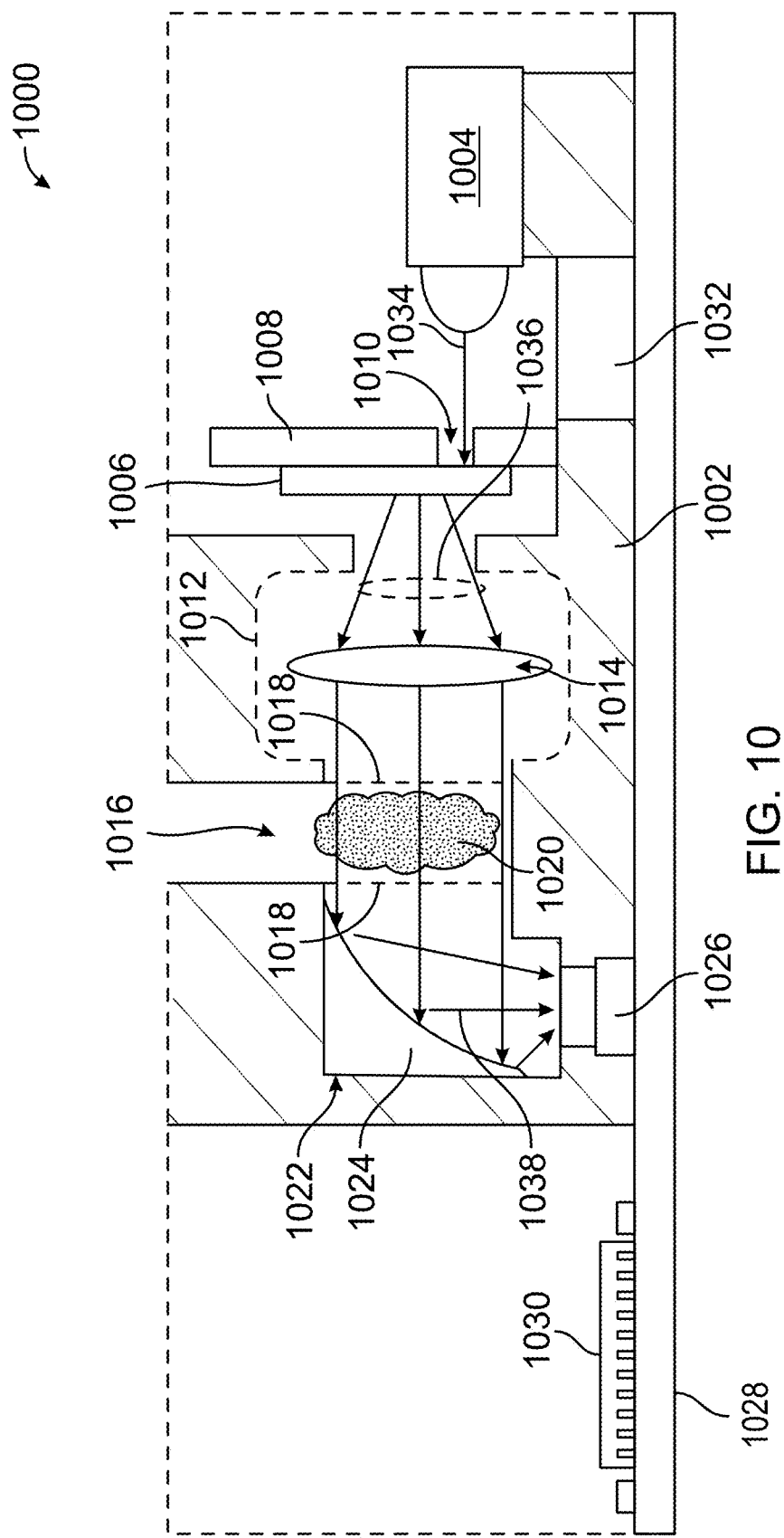
FIG. 10 is a diagram illustrating an example of a spectral sensor of a spectral analyzer operating in a transmission mode according to some aspects.

FIG. 10 is a diagram illustrating an example of a spectral sensor 1000 of a spectral analyzer operating in a transmission mode according to some aspects. The spectral sensor 1000 includes a chassis 1002 that is configured to both align and connect together various components, such as a light source 1004, a light modulator 1006 (e.g., a light modulation chip including the light modulator), illumination optical element(s) 1012, collection optical element(s) 1022, and a detector 1026.

In the example shown in FIG. 10, a sample compartment 1016 is formed in the chassis 1002 between a pair of opposing optical windows 1018 and is configured to receive a sample 1020 (e.g., a biological sample). For example, the sample compartment 1016 may be configured to receive the sample 1020 in a cuvette, bag, etc. Thus, the sample 1020 is positioned between the illumination optical element(s) 1012 and the collection optical element(s) 1022 to operate in a transmission mode. The optical windows 1018 are configured to protect the illumination optical element(s) 1012 and the collection optical element(s) 1022 from contamination.

A substrate (e.g., an electronic board substrate or mother board) 1028 may be attached to the chassis 1002. The mother board 1028 may include the detector 1026 and processor 1030 thereon. The processor 1030 may be configured to control the light modulator 1006 and the detector 1026. The light modulation chip including the light modulator 1006 is shown attached to a first side of an additional substrate 1008 (e.g., a daughter board or chip carrier) opposite a second side of the substrate 1008 adjacent the light source 1004. The daughter board 1008 is assembled on the chassis 1002 and includes an aperture 1010 configured to pass a first portion of input light 1034 emitted from the light source 1004 and to block a second portion of the input light (e.g., light corresponding to non-useful rays). The daughter board 1008 may provide a connection between the light modulation chip 1006 and the mother board 1028.

The light modulator 1006 is configured to receive the first portion of the input light 1034 passed by the aperture 1010 of the daughter board 1008 and to produce modulated light 1036 based on the input light 1034. The illumination optical element(s) 1012 may include an illumination lens 1014 configured to collimate the modulated light 1036 parallel to the mother board 1028 and to direct the modulated light 1036 towards the sample 1020 to produce output light 1038 in the transmission mode. The output light 1038 may then be directed by the collection optical element(s) 1022 to the detector 1026. In the example shown in FIG. 10, the collection optical element(s) 1022 includes a curved reflector 1024.

In addition, a thermal separator 1032 may optionally be attached between the chassis 1002 and the light source 1004. The thermal separator 1032 is configured to thermally insulate the mother board 1028 and daughter board 1008 from the light source 1004, thus isolating the light source 1004 from temperature-sensitive components, such as the detector 1026.

Figure 11:
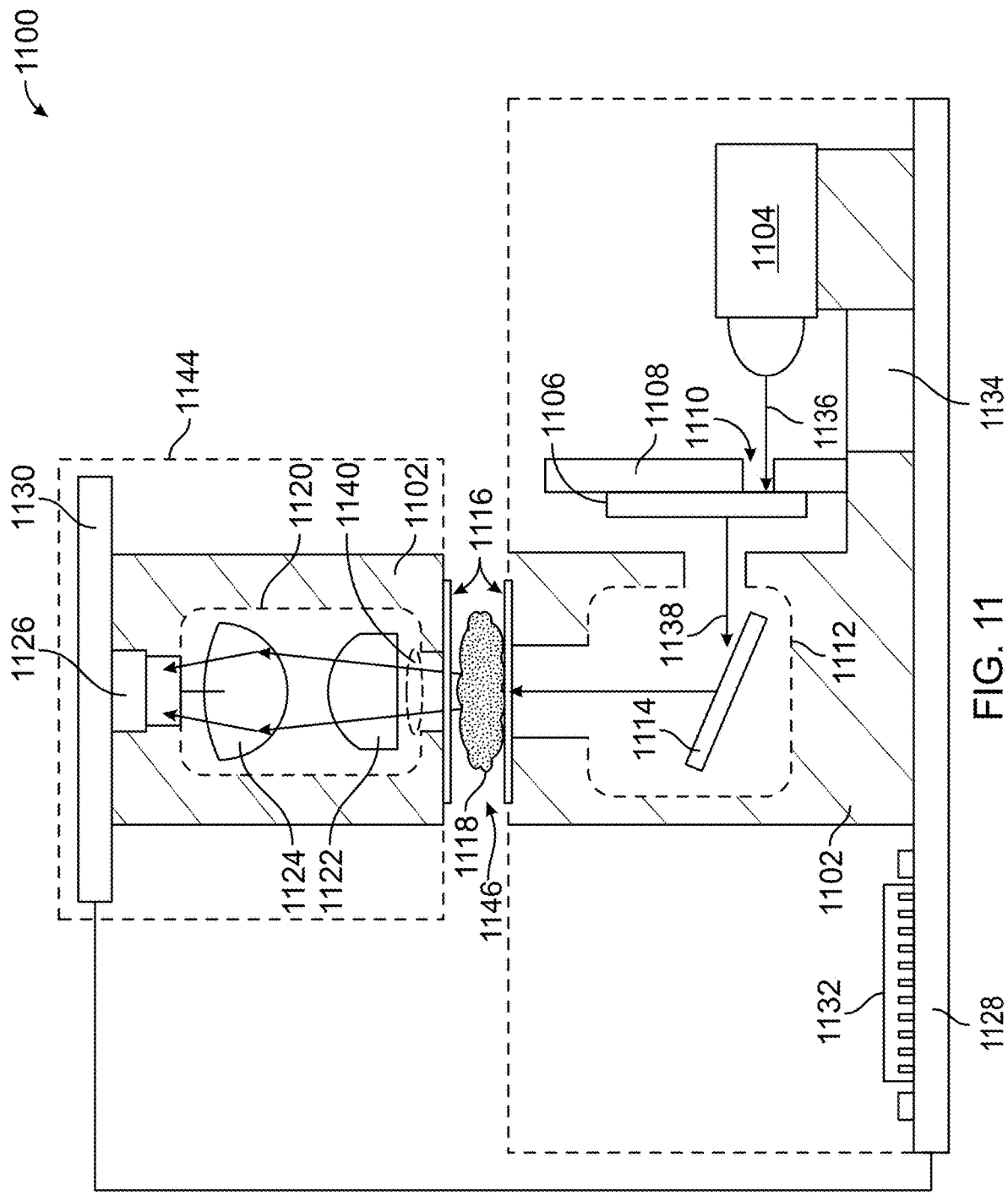
FIG. 11 is a diagram illustrating another example of a spectral sensor of a spectral analyzer operating in a transmission mode according to some aspects.

FIG. 11 is a diagram illustrating another example of a spectral sensor 1100 of a spectral analyzer operating in a transmission mode according to some aspects. The spectral sensor 1100 includes a chassis 1102 that is configured to both align and connect together various components, such as a light source 1104, a light modulator 1106 (e.g., a light modulation chip including the light modulator), illumination optical element(s) 1112, collection optical element(s) 1120, and a detector 1126.

In the example shown in FIG. 11, a sample compartment 1146 is formed in the chassis 1102 between a pair of opposing optical windows 1116 and is configured to receive a sample 1118 (e.g., a biological sample). For example, the sample compartment 1146 may be configured to receive the sample 1118 in a cuvette, bag, etc. Thus, the sample 1118 is positioned between the illumination optical element(s) 1112 and the collection optical element(s) 1120 to operate in a transmission mode. The optical windows 1116 are configured to protect the illumination optical element(s) 1112 and the collection optical element(s) 1120 from contamination.

In the example shown in FIG. 11, the detector 1126 is isolated in a separate module 1144 (e.g., a light detection module). The light detection module 1144 can include the detector 1126 and the collection optical element(s) 1120. This configuration of the light detection module 1144 enables more flexibility in integrating a cooling element with the detector 1126 and further isolates the detector 1126 from thermal aggressors in the light source 1104 and light modulation chip 1106.

A substrate (e.g., an electronic board substrate or mother board) 1128 may be attached to the chassis 1102. The mother board 1128 may include processor 1132 thereon. A separate substrate 1130 for the light detection module 1144 may further be attached to the chassis 1102. The detector 1126 may be attached to the separate substrate 1130, which may further be connected to the mother board 1128. Thus, the processor 1132 may be configured to control both the light modulator 1106 and the detector 1126 (e.g., via the separate substrate 1130).

The light modulation chip including the light modulator 1106 is shown attached to a first side of an additional substrate 1108 (e.g., a daughter board or chip carrier) opposite a second side of the substrate 1108 adjacent the light source 1104. The daughter board 1108 is assembled on the chassis 1102 and includes an aperture 1110 configured to pass a first portion of input light 1136 emitted from the light source 1104 and to block a second portion of the input light (e.g., light corresponding to non-useful rays). The daughter board 1108 may provide a connection between the light modulation chip 1106 and the mother board 1128.

The light modulator 1106 is configured to receive the first portion of the input light 1136 passed by the aperture 1110 of the daughter board 1108 and to produce modulated light 1138 based on the input light 1136. The illumination optical element(s) 1112 may include a redirecting (or folding) mirror 1114 configured to redirect the modulated light 1138 towards the sample 1118 to produce output light 1140 in the transmission mode. The output light 1140 may then be directed by the collection optical element(s) 1120 to the detector 1126. In the example shown in FIG. 11, the collection optical element(s) 1120 includes a two-lens system including a pair of lenses 1122 and 1124.

In addition, a thermal separator 1134 may optionally be attached between the chassis 1102 and the light source 1104. The thermal separator 1134 is configured to thermally insulate the mother board 1128 and daughter board 1108 from the light source 1104, thus isolating the light source 1104 from temperature-sensitive components.

Figure 12:
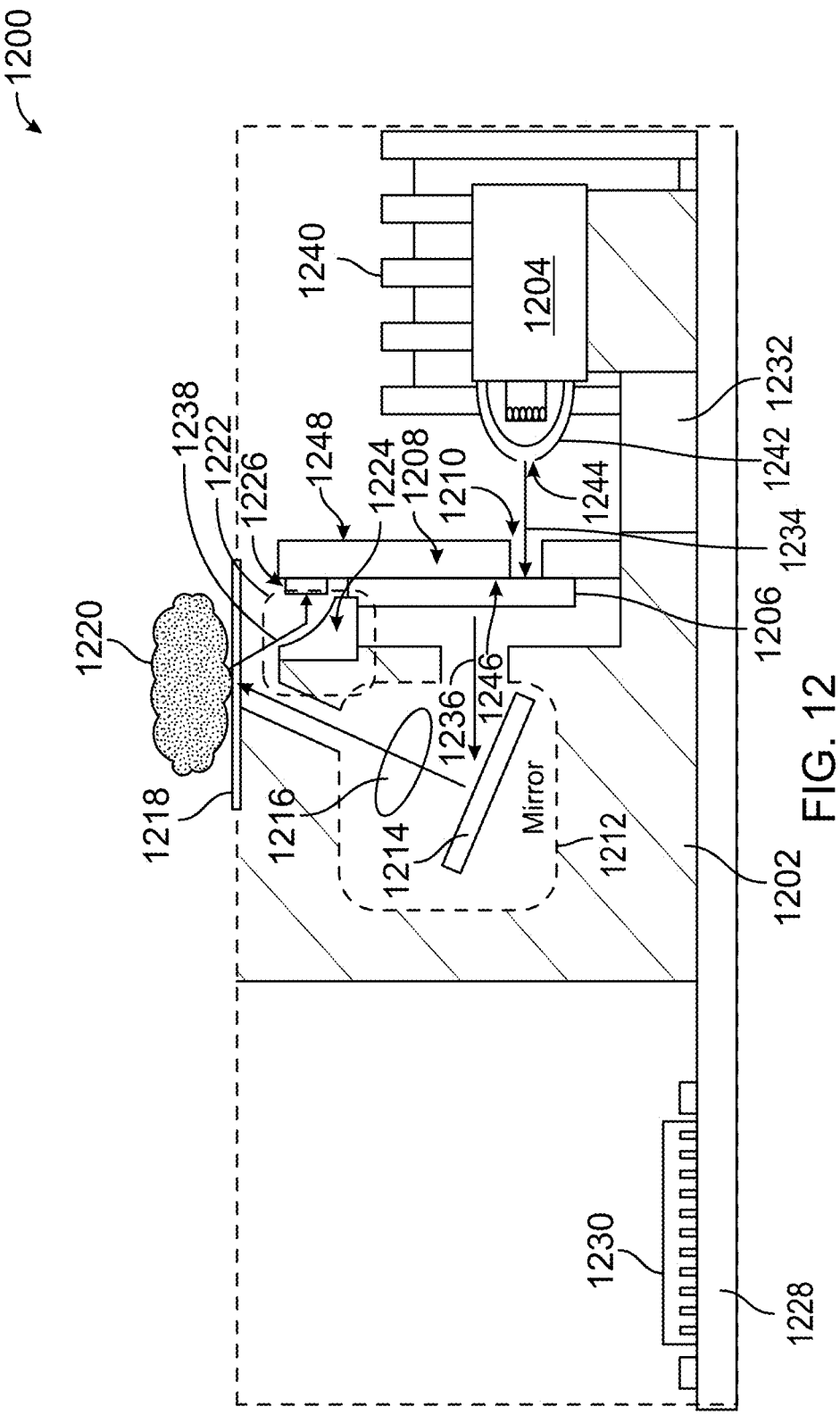
FIG. 12 is a diagram illustrating another example of a spectral sensor of a spectral analyzer operating in reflection mode according to some aspects.

FIG. 12 is a diagram illustrating another example of a spectral sensor 1200 of a spectral analyzer operating in reflection mode according to some aspects. The spectral sensor 1200 includes a chassis 1202 that is configured to both align and connect together various components, such as a light source 1204, a light modulator 1206 (e.g., a light modulation chip including the light modulator), illumination optical element(s) 1212, collection optical element(s) 1222, and a detector 1226. An optical window 1218 is shown positioned on a top surface of the spectral sensor 1200 and is configured to receive a sample 1220 (e.g., a biological sample) on an external surface thereof.

A substrate (e.g., an electronic board substrate or mother board) 1228 may be attached to the chassis 1202. The mother board 1228 may include processor 1230 thereon. The processor 1230 may be configured to control the light modulator 1206 and the detector 1226. The light modulation chip including the light modulator 1206 is shown attached to a first side 1246 of an additional substrate 1208 (e.g., a daughter board or chip carrier) opposite a second side 1248 of the substrate 1208 adjacent the light source 1204. In addition, in the example shown in FIG. 12, the detector 1226 is further attached to the first side 1246 of the daughter board 1208.

The daughter board 1208 is assembled on the chassis 1202 and includes an aperture 1210 configured to pass a first portion of input light 1234 emitted from the light source 1204 and to block a second portion of the input light (e.g., light corresponding to non-useful rays). The daughter board 1208 may provide a connection between the mother board 1228 and each of the light modulation chip 1206 and the detector 1226. In addition, the light source 1204 may further include a source cover 1242 having an additional aperture 1244 therein configured to block a portion of incident light generated by the light source 1204 to produce the input light 1234. In addition, one or more of the apertures 1210 and 1244 may further be designed to match the beam solid angle of the input light 1234 to the effective numerical aperture of the light modulation chip.

The light modulator 1206 is configured to receive the first portion of the input light 1234 passed by the apertures 1210 and 1244 of the daughter board 1208 and the source cover 1242, and is further configured to produce modulated light 1236 based on the input light 1234. The modulated light 1236 may then be directed by the illumination optical element(s) 1212 to the optical window 1218 for interaction with the sample 1220 to produce output light 1238 in a reflection mode. The illumination optical element(s) 1212 may include a redirecting mirror (e.g., a folding mirror) 1214 and a focusing lens 1216.

The output light 1238 from the sample 1220 passes back through the optical window 1218 and is directed to the detector 1226 via the collection optical element(s) 1222. In the example shown in FIG. 12, the collection optical element(s) 1222 includes a curved reflector 1224 configured to direct the output light 1238 to the detector 1226 on the daughter board 1208.

In addition, a thermal separator 1232 may optionally be attached between the chassis 1202 and the light source 1204. The thermal separator 1232 is configured to thermally insulate the mother board 1228 and daughter board 1208 from the light source 1204, thus isolating the light source 1204 from temperature-sensitive components, such as the detector 1226. In addition, the spectral sensor 1200 may further include a heat sink 1240 coupled to the light source 1204 and attached to the chassis 1202. The heat sink 1240 is configured to remove heat from the light source 1204 to further protect the other spectral sensor components and the sample 1220 from heating.

Figure 13A:
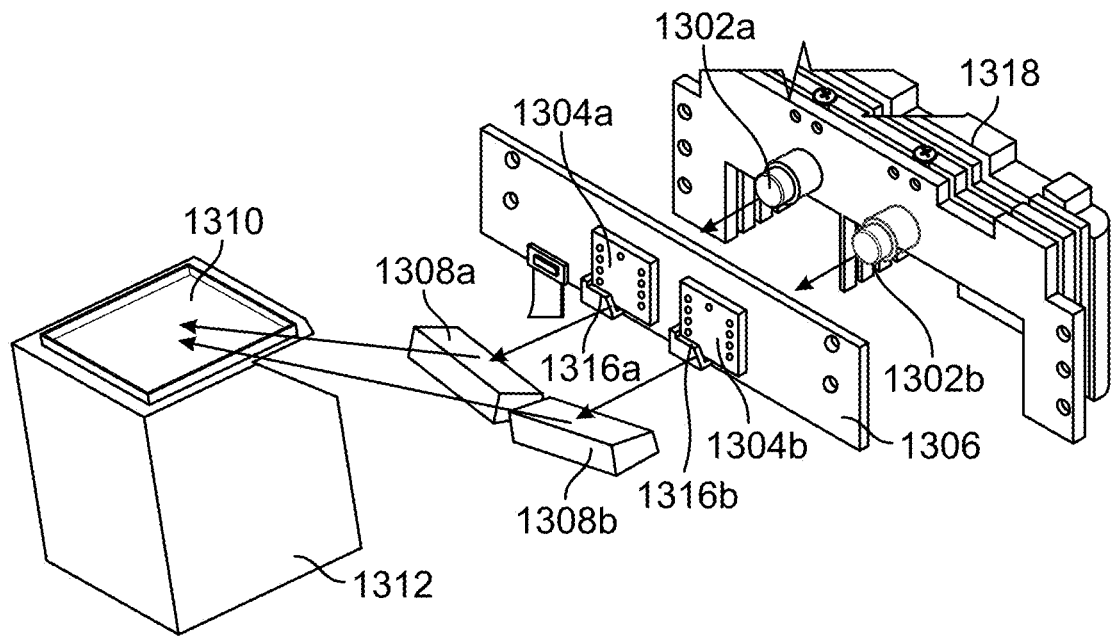
FIGS. 13A and 13B are diagrams illustrating an example of a spectral sensor including multiple light modulation paths according to some examples.
Figure 13B:
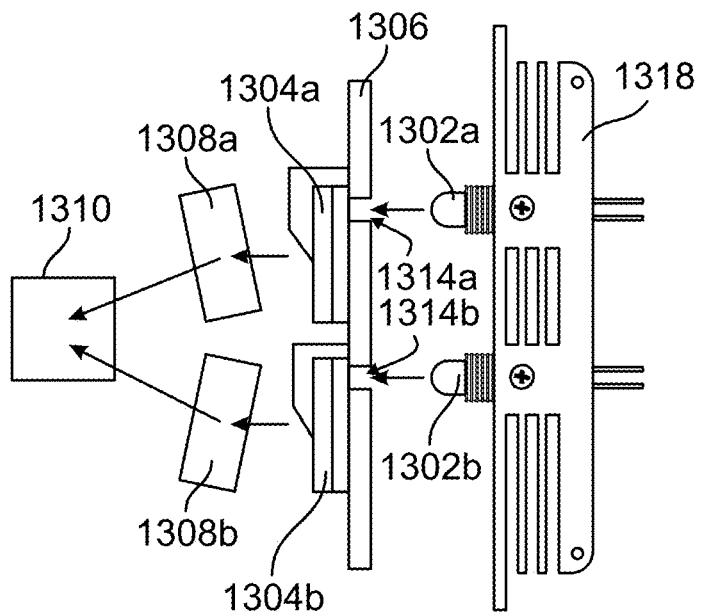

FIGS. 13A and 13B are diagrams illustrating an example of a spectral sensor including multiple light modulation paths according to some examples. To improve the signal-to-noise (SNR) ratio, multiple parallel light chips 1304a and 1304b may be used, as shown in FIGS. 13A and 13B. For example, multiple light modulation chips 1304a and 1304b, each including a respective light modulator (e.g., MEMS interferometer) may be attached on a same daughter board 1306 (as shown in FIGS. 13A and 13B) or on multiple daughter boards. The daughter board 1306 (or each separate daughter board) includes a respective aperture 1314a and 1314b for passing respective input light into the respective light modulation chip 1304a and 1304b. Each light modulation chip 1304a and 1304b may further include a respective light coupling molded optics component 1316a and 1316b for coupling out-of-plane light to and from the light modulation chip 1304a and 1304b, where the light propagates through light modulator in-plane parallel to the light modulation chip substrate and the daughter board 1306.

In some examples, as shown in FIGS. 13A and 13B, the spectral sensor may include multiple light sources 1302a and 1302b, each configured to produce a respective input light beam for input to a respective one of the light modulation chips 1306a and 1306b via a respective aperture 1314a and 1314b. For example, the multiple light sources 1302a and 1302b may be integrated together within a light source housing 1318, which in some examples, may further function as a heat sink. In other examples, a single light source (e.g., a single bulb) may be used and additional optical reflectors may be added to maximize the coupled power to the multiple light modulation chips 1304a and 1304b. The respective modulated light produced by each of the light modulation chips 1304a and 1304b may be directed by respective illumination optical elements 1308a and 1308b (e.g., mirrors, lenses, reflectors, etc.) towards an optical window 1310 to interact with a sample (not shown) thereon and produce output light collected by a light detection module 1312 (e.g., including collection optical element(s) and a detector). In some examples, the illumination optical elements 1308a and 1308b may be configured to direct the modulated light beams towards a same location (e.g., spot) on the sample, thus maximizing the amount of power hitting the sample. In other examples, the illumination optical elements 1308a and 1308b may be configured to direct their respective modulated light beams towards different spots, which may be adjacent to one another, on the sample to increase the illumination spot size. In this example, the light detection module 1312 may be configured to collect an averaged and/or more repeatable reflected scattered light from the sample.

Referring to the spectral sensor designs shown in FIGS. 4, 5A-5C, and/or 9-13B, each of these designs contains multiple thermal aggressors, including, for example, the light source and the processor (e.g., the electronic control and processing chips). In addition, each of these designs further includes multiple thermally-sensitive optical core components, including, for example, the light modulation chip (e.g., light modulator), the detector, the illumination optical element(s), and the collection optical element(s). Therefore, various aspects are directed to minimizing the heating of the thermally-sensitive components.

Figure 14A:
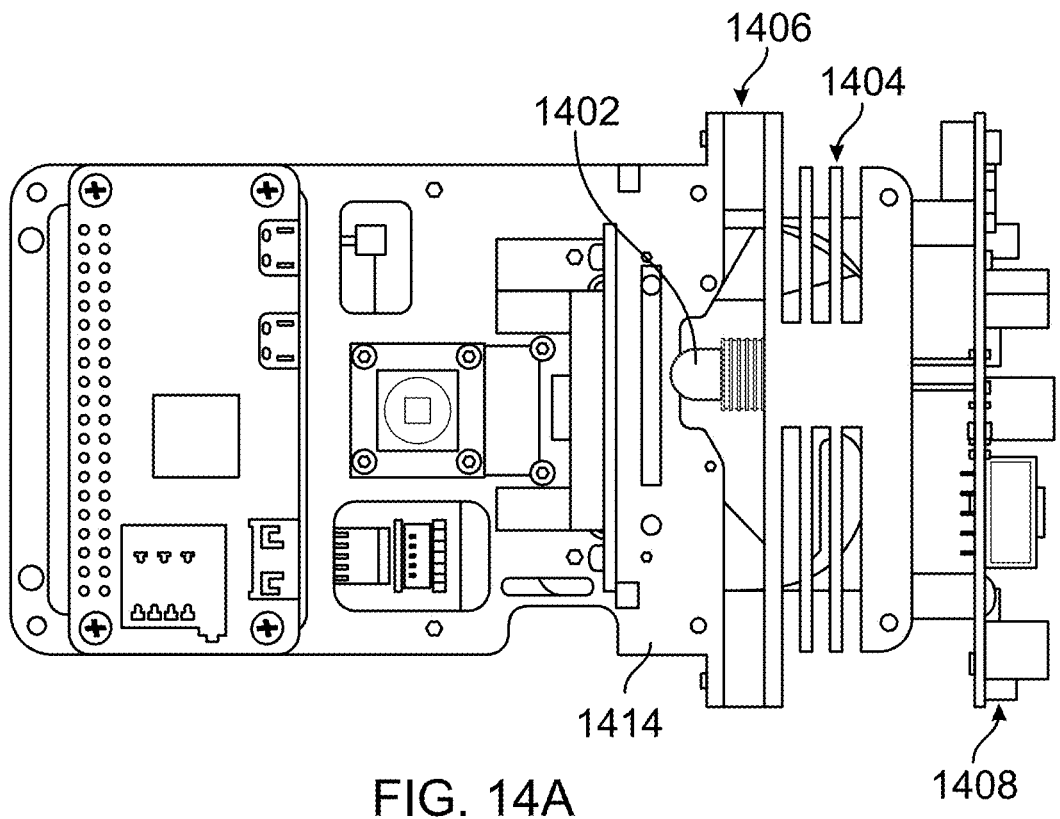
FIGS. 14A and 14B are diagrams illustrating an example of a spectral sensor including thermal management components according to some aspects.
Figure 14B:
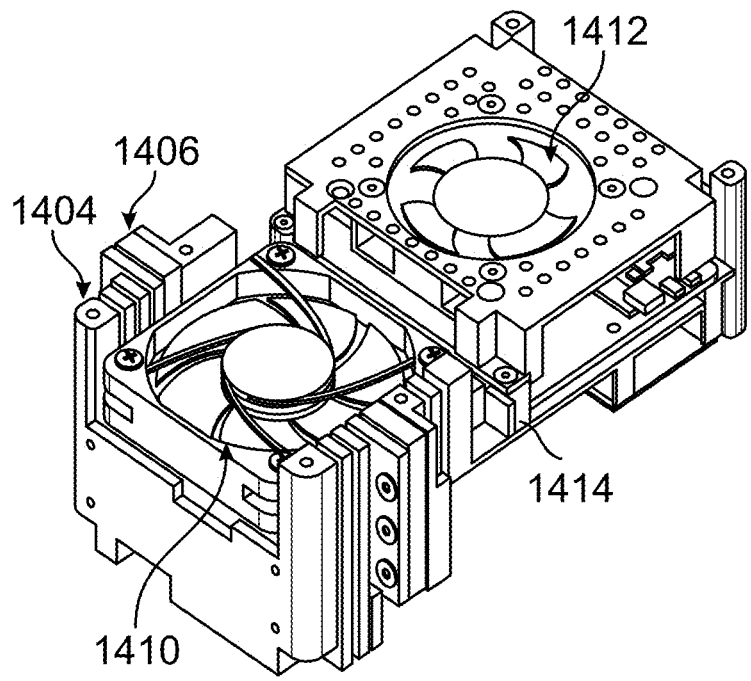

FIGS. 14A and 14B are diagrams illustrating an example of a spectral sensor including thermal management components according to some aspects. In the example shown in FIGS. 14A and 14B, a light source module 1402 (e.g., a light source housing including a light source) is shown connected to a heat sink 1404. In addition, the light source module 1402 is isolated from a main chassis 1414 using thermal separators 1406 of very low thermal conductivity. The main chassis 1414 that holds the electronic substrate and the optical components may further be metallic to act as a heat sink. In some examples, the spectral sensor enclosure (not shown) can be metallic as well to improve the heat sinking process. A power board 1408 including power circuitry (e.g., main power chips and light source driving chips) configured to provide power, for example, to the mother board, daughter board, and light source may further be isolated on a separate board attached to the light source module 1402 away from the thermally-sensitive components. Thus, the power board 1408 can be thermally insulated from the chassis 1414. Two fans 1410 and 1412 may further be added to the backside of the light source module 1402 and the backside of the mother board attached to the chassis 1414 to remove the heat from the light source module, power board, and the main electronic board substrate (e.g., mother board).

Figure 15A:
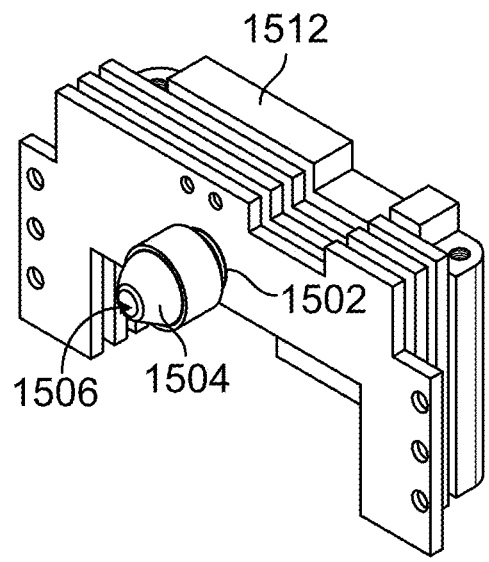
FIGS. 15A-15C are diagrams illustrating examples of a light source of the spectral sensor according to some aspects.
Figure 15B:
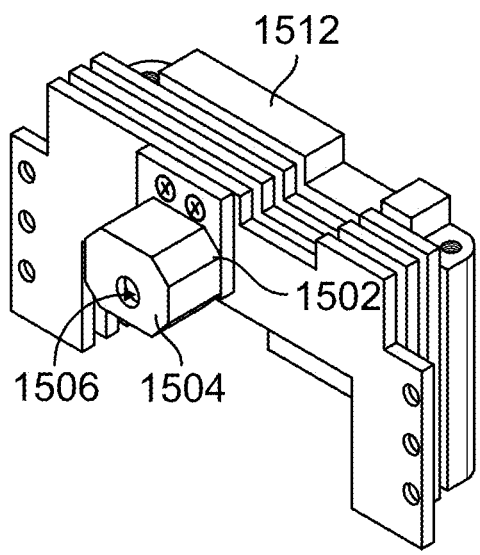
Figure 15C:
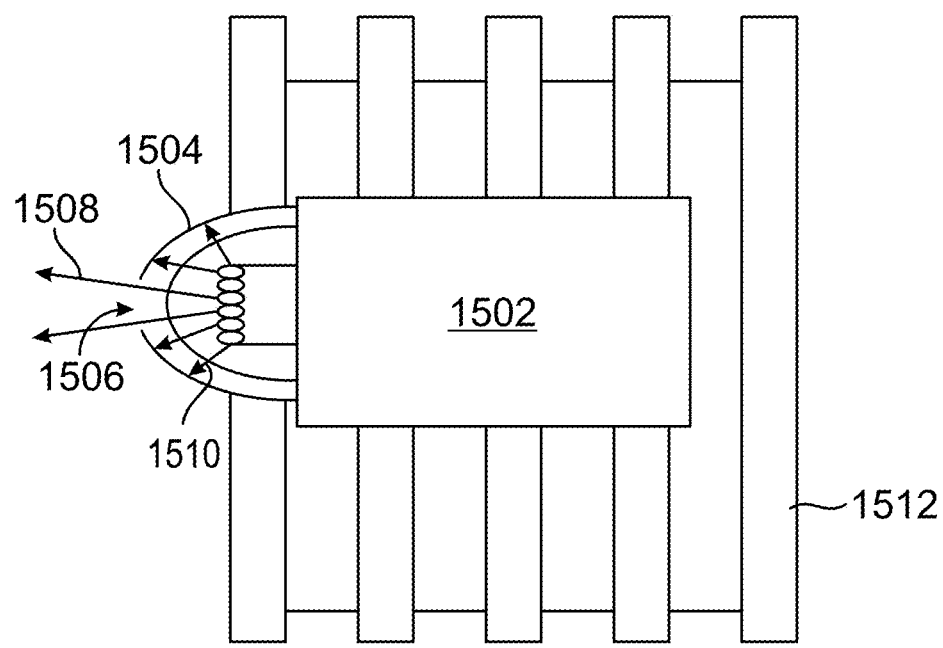

FIGS. 15A-15C are diagrams illustrating examples of a light source 1502 of the spectral sensor according to some aspects. The light source 1502 may be attached to or contained within a light source module 1512. In some examples, the light source module 1512 may correspond to a light source housing containing the light source 1502. In other examples, the light source module 1512 may be a heat sink that is attached to the light source 1502. In some examples, the heat sink may form the light source housing. In other examples, the light source module 1512 may correspond to a part of the main chassis of the spectral sensor that functions as a heat sink for the light source 1502.

The light source 1502 may further include a source cover 1504 having an aperture 1506 therein configured to block a portion of the incident light generated by the light source 1502. For example, as shown in FIG. 15C, the aperture 1506 of the source cover 1504 may be configured to pass a first portion 1508 of the incident light and block a second portion 1510 of the incident light. Thus, the aperture 1506 prevents the non-useful light (e.g., second portion 1510 of the incident light) from the light source 1502 from reaching the thermally-sensitive components of the main optical core. In some examples, the aperture 1506 may further be designed to match the beam solid angle of the input light (e.g., the useful light or first portion 1508 of the incident light) to the effective numerical aperture of the light modulation chip. In some examples, as shown in FIG. 15B, the source cover 1504 may be a metallic cover attached to the head of the light source 1502. In this example, the source cover 1504 may further function as a heat sink.

Figure 16A:
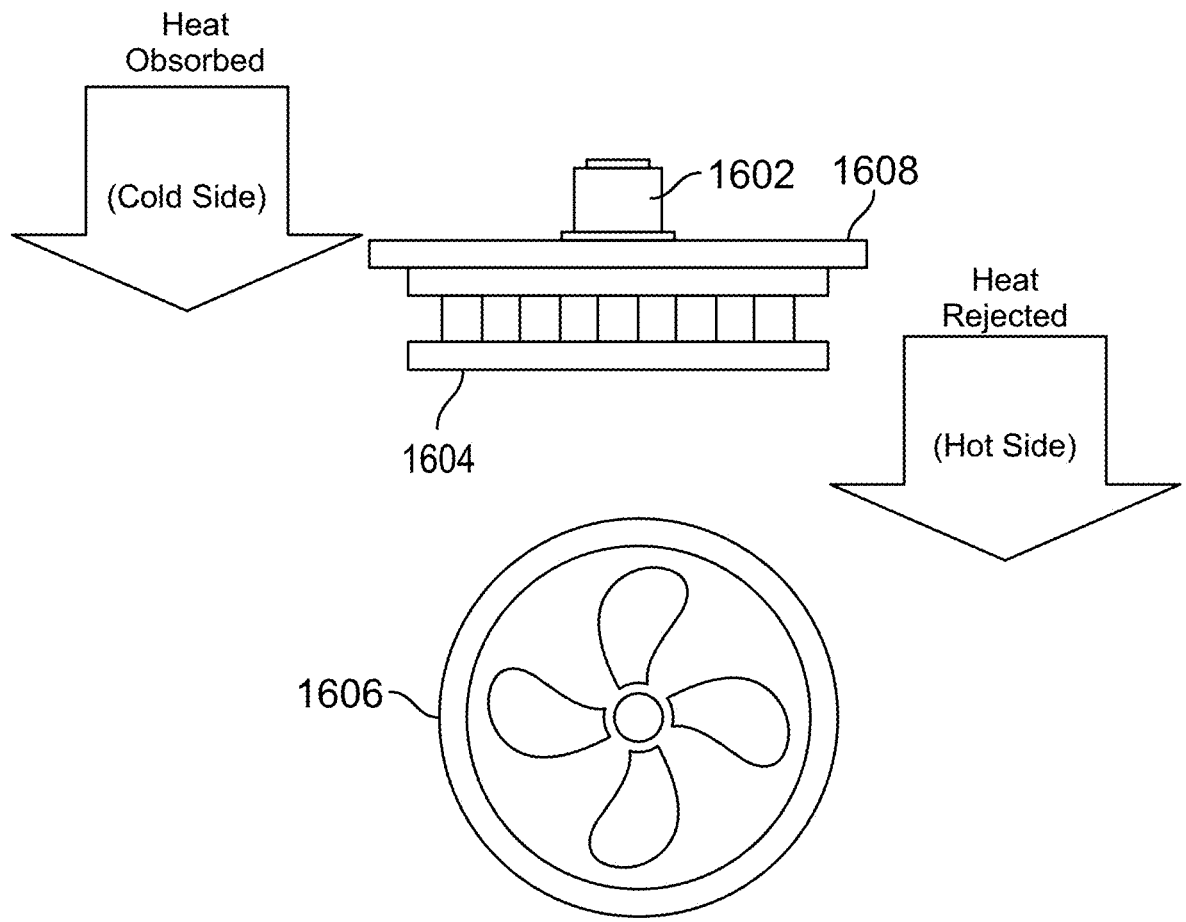
FIGS. 16A and 16B are diagrams illustrating an example of thermal cooling of a detector of the spectral sensor according to some aspects.
Figure 16B:
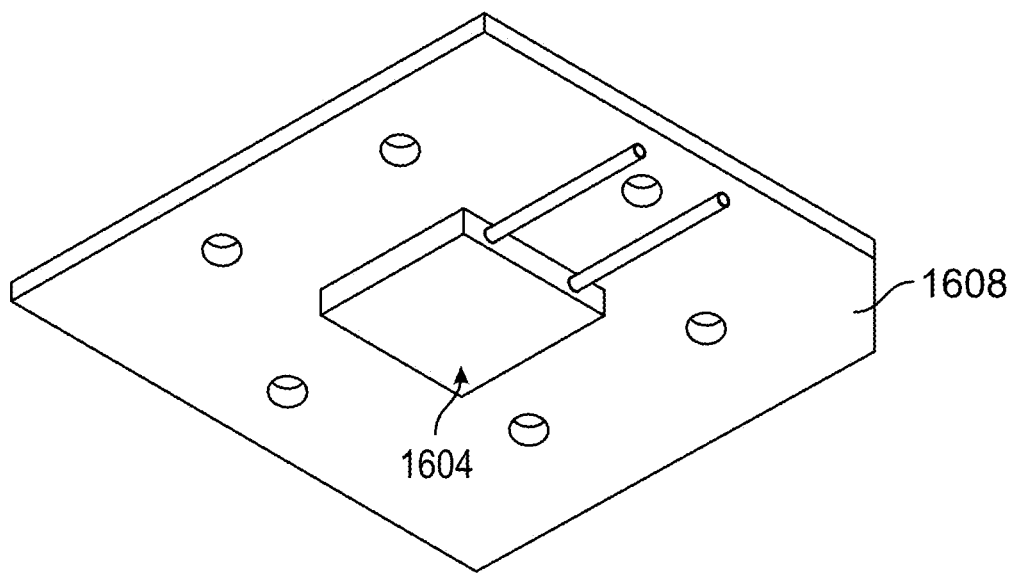

FIGS. 16A and 16B are diagrams illustrating an example of thermal cooling of a detector 1602 of the spectral sensor according to some aspects. In the example shown in FIG. 16A, the detector 1602 (e.g., a photodetector) is attached to a top side of the main electronic substrate (e.g., mother board) 1608. As shown in FIGS. 16A and 16B, the photodetector 1602 can be thermally stabilized or cooled by attaching a Peltier element 1604 on the backside of the electronic substrate 1608. In addition, a fan 1606 may be attached to the backside of the mother board 1608 below the Peltier element 1604 to remove heat from the Peltier element 1604. Thus, the heat from the photodetector 1602 may be absorbed by the Peltier element 1604 and rejected or removed by the fan 1606. In some examples, thermo-electric cooling (TEC) control chips (not shown) can further be integrated on the mother board 1608 to receive a control signal from a thermistor (not shown) adjacent to the photodetector 1602 and to control the Peltier element 1604 based on the control signal or based on detected signal drift or detector noise increase. It should be understood that TEC can be extended to other thermally-sensitive components in the spectral sensor.

Figure 17:
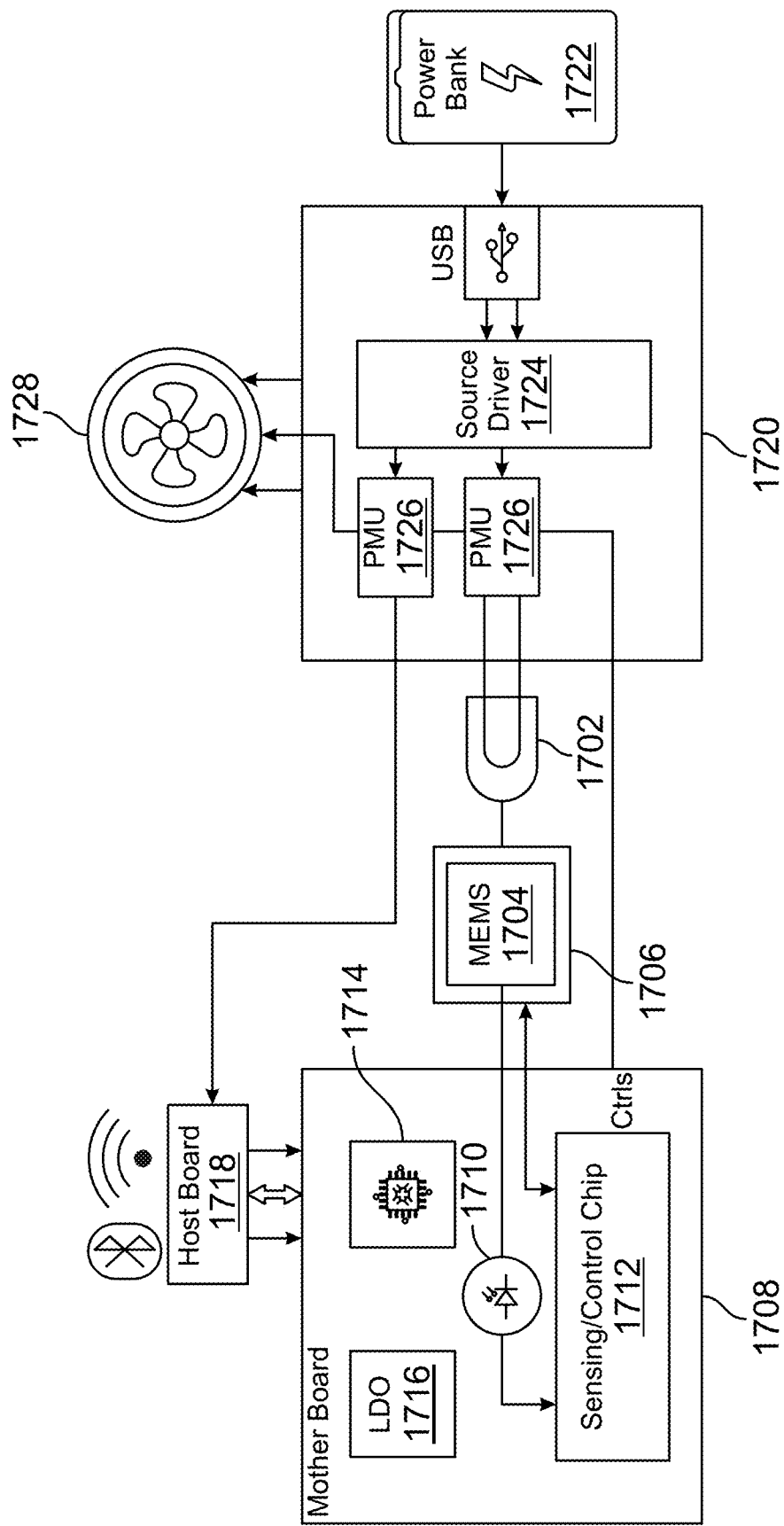
FIG. 17 is a diagram illustrating an electrical system architecture of a spectral analyzer according to some aspects.

FIG. 17 is a diagram illustrating an electrical system architecture of a spectral analyzer according to some aspects. The electrical system architecture shown in FIG. 17 is divided between four substrates (e.g., four boards), including a mother board 1708, a daughter board 1706, a power board 1720, and a host board 1718. The power board 1720 contains the main power management units (PMUs) 1726 and a source driver circuit 1724. Electrical power can be delivered from a power source 1722, such as a battery, power bank, power supply, or an adaptor through, for example, a USB connector, or other suitable connection. The power board 1720 may drive one or more fans (e.g., fan 1728), the mother board 1708, the daughter board 1706, the host board 1718, and a light source 1702 of the spectral sensor via the PMUs 1726.

The mother board 1708 is directly connected to the daughter board 1706 that holds a light modulation chip 1704. The mother board 1708 further holds a detector (e.g., photodetector) 1710, along with one or more sensing/control chips 1712 that interface with and control the light modulation chip 1704 and the photodetector 1710. In addition, the mother board 1708 contains a processor chip (e.g., processor) that post-processes the detected signal (e.g., interferogram) and converts it to spectral data (e.g., a spectrum) to be communicated to the host board 1718. Thus, the sensing/control chips 1712 and microprocessor may collectively form the processor 432 shown in FIG. 4 and similarly shown in other Figures. The processor 1714 may include a single processing device or a plurality of processing devices. Such a processing device may be a microprocessor, micro-controller, digital signal processor, microcomputer, central processing unit, field programmable gate array, programmable logic device, logic circuitry, analog circuitry, digital circuitry, and/or any device that manipulates signals (analog and/or digital) based on hard coding of the circuitry and/or operational instructions. The mother board 1708 may further include low drop-out (LDO) linear regulators to deliver stable supply voltages to the different chips on the mother board 1708.

The microprocessor 1714 controls the operation of the different components of the spectral sensor, synchronizing the operation of the light source 1702, the light modulation chip 1704, and the fan(s) 1728. For example, the microprocessor 1714 can switch on the light source 1702 and the fan(s) 1728 once the microprocessor 1714 receives a request for a sample measurement. The microprocessor 1714 may further drive the moveable mirror of the light modulation chip to obtain the spectrum of a sample. In the case of continuous monitoring, spectral sensor components may be continuously operating within specified active hours, or can be continuously switching on/off taking a measurement each few seconds/minutes.

The sensing/control chip(s) 1712 may include, for example, a capacitance-to-voltage converter (C/V) circuit that senses the time varying capacitance of the MEMS actuator inside the light modulation chip 1704. The capacitance signal is directly related to the position of the movable mirror of the light modulator (e.g., interferometer) in the light modulation chip 1704. The circuit converts the capacitance into a proportional voltage and a very low-noise amplifier is used to amplify the voltage output from the C/V. An actuation circuit within the sensing/control chips 1712 is used for generating an actuation signal to drive the MEMS actuator attached to the interferometer moveable mirror, leading to light modulation by the displacement of the mirror. An optical detection interfacing circuit within the light modulation chip 1704 including an optimized differential Trans-Impedance Amplifier TIA receives the detected current. It functions as a low-noise signal conditioning path that amplifies the signal, removes any DC offsets and provides necessary anti-aliasing filtering. The optical detection interface also includes an Analog to Digital Converter (ADC) to digitize the signal before passing it to a digital signal processor (DSP) (e.g., in the sensing/control chips 1712 or microprocessor 1714) for processing the interferogram and extracting the spectrum through fast Fourier transform FFT in case of FT-IR light modulator systems.

The host board 1718 is connected to the mother board 1708 through a serial peripheral interface SPI, acting as an interface with external devices, though different connectivity methods, including USB, BLUETOOTH, and WIFI interfaces. The host board 1718 thus enables communication with different platforms, including cell phones, PCs, laptops, tablets, and other embedded systems.

Figure 18C:
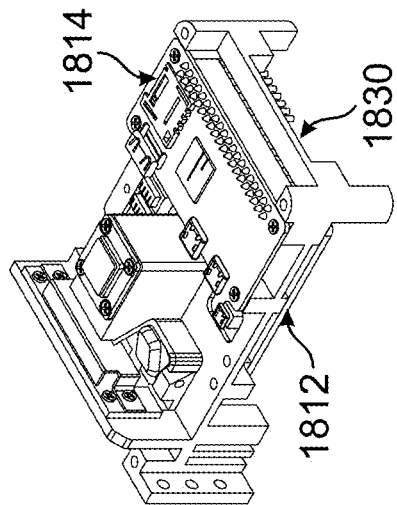
FIGS. 18A-18F are diagrams illustrating mechanical assembly of a spectral analyzer according to some aspects.
Figure 18F:
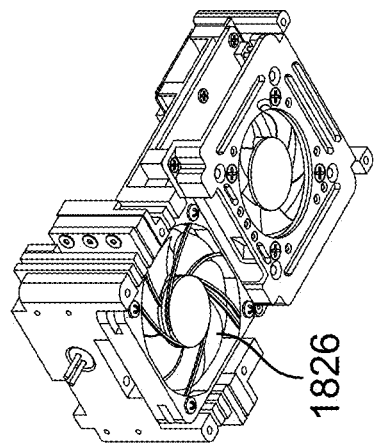
Figure 18B:
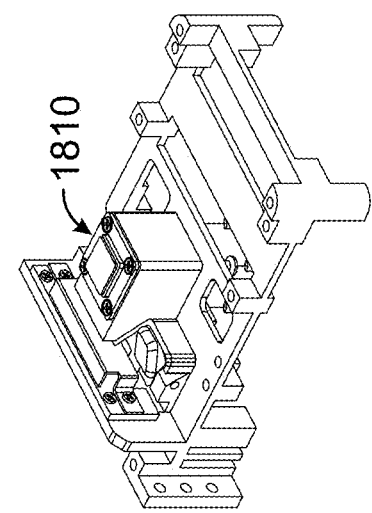
Figure 18E:
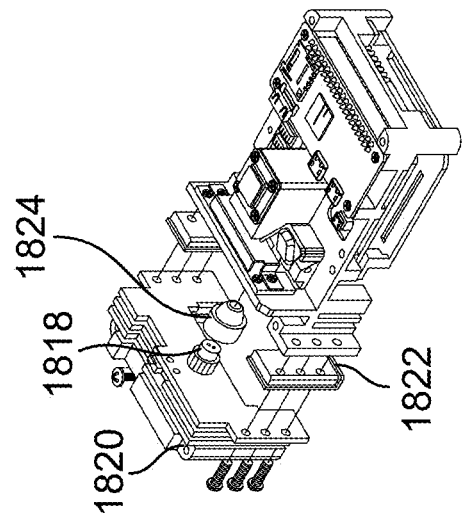
Figure 18A:
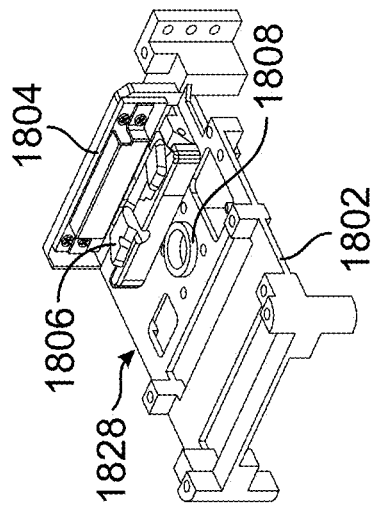
Figure 18D:
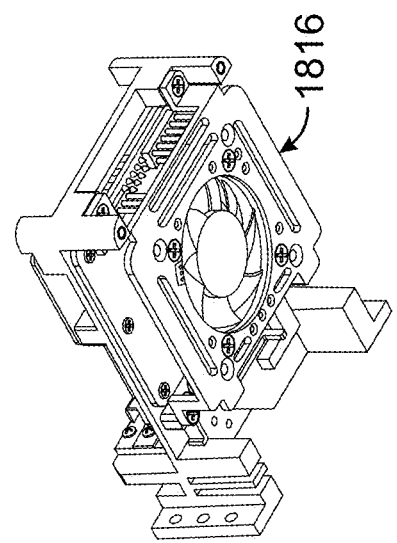

FIGS. 18A-18F and FIGS. 19A-19B are diagrams illustrating mechanical assembly of a spectral analyzer according to some aspects. As shown in FIG. 18A, a main chassis 1802 may be used to assemble the various components. For example, a daughter board 1804 including the light modulation chip and a folding mirror (e.g., redirecting mirror) of the illumination optical element(s) may be attached to a first side 1828 of the main chassis 1802. The main chassis 1802 may further include an aperture for a detector to be inserted (e.g., via attachment of a mother board having the detector thereon). In FIG. 18B, an optics block 1810 including at least the collection optical elements may be attached to the main chassis 1802. As shown in FIG. 18C, a mother board 1812 containing the detector and a host board 1814 may be attached to a second side (backside) 1830 of the chassis 1802. The mother board 1812 may be attached to a first side (e.g., backside) of the chassis 1802, whereas the host board 1814 may be attached to a second side (e.g., top side) of the chassis 1802. In addition, as shown in FIG. 18D, a mother board fan 1816 may then be attached to the backside of the chassis 1802.

As shown in FIG. 18E, a light source module 1820 including a light source 1818 inserted therein may then be connected and attached to the main chassis 1802. For example, the light source 1818 may be screwed inside a threaded hole in the light source module 1820. As another example, the light source 1818 may be fixed in the light source module 1820 using an epoxy. A topside screw can further be used for fixation of the light source 1818. In some examples, the light source module 1820 may function as a heat sink for the light source 1820. Thermal separator(s) 1822 may further be connected between the light source module 1820 and the main chassis 1802. A source cover 1824 may further be attached to the light source 1818. In FIG. 18F, a light source fan 1826 may be attached to the backside of the light source module 1820. Then, a power board (not shown) may be attached to the light source module 1820 and connected to the other analyzer components.

Figure 19B:
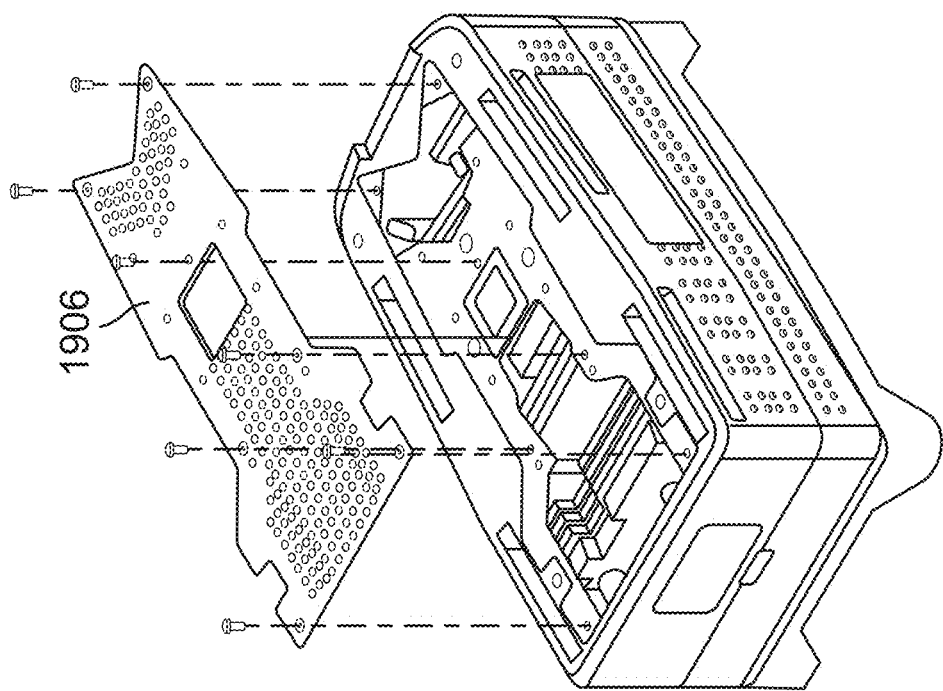
FIGS. 19A-19B are diagrams illustrating further mechanical assembly of the spectral analyzer according to some aspects.
Figure 19A:
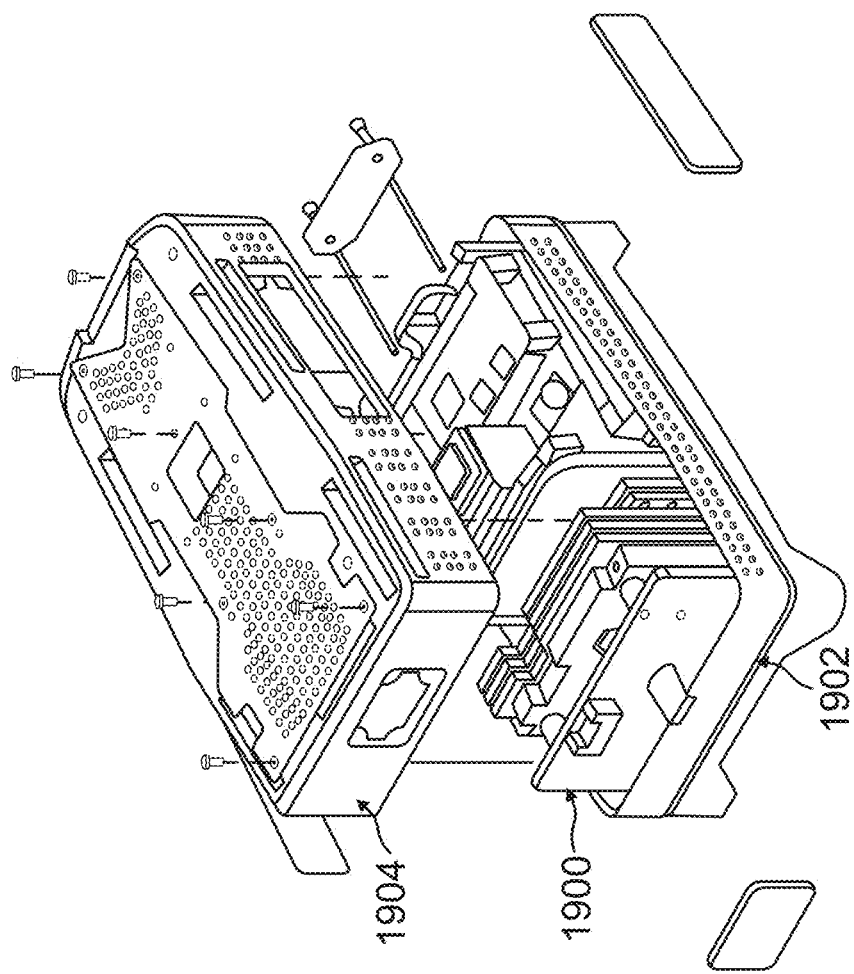

The optical system including, for example, the light source 1818, light modulation chip, illumination optical element(s) and collection optical element(s), may then be aligned for optimum maximized signal. As shown in FIGS. 19A and 19B, the spectral analyzer 1900 may then be calibrated and assembled inside a metallic enclosure 1902 and 1904. For example, the spectral analyzer 1900 may be attached to a lower half 1902 of the enclosure. Thereafter, an upper half 1904 of the enclosure may be attached and fixed. The upper half 1904 of the enclosure may further include an opening in the metallic part to allow BLUETOOTH and WIFI connectivity, which may then be covered by a plastic cover sheet 1906 above the host board. In some examples, another opening (not shown) may be made above the light source to allow air circulation above the light source. Multiple openings may further be made on the sides of the enclosure and the lower half 1902 of the enclosure to allow the fans to push hot air out of the spectral analyzer 1900.

FIG. 20A is a diagram illustrating an example wearable spectral analyzer 2000 according to some aspects. In the example shown in FIG. 20A, the spectral analyzer 2000 can have a compact form factor to enable the spectral analyzer 2000 to be used as a handheld device. In an example, the spectral analyzer 2000 may be fixed on or attached to skin (e.g., a forearm) of a subject 2002 using, for example, straps with clips. In other examples, the wearable spectral analyzer 2000 can be attached to an upper arm or abdomen of the subject 2002. The spectral analyzer can be also used as a fixed device at doors, in cars, on benches, or in point-of-case testing (POCT).

As a portable/wearable device attached to the skin for continuous monitoring, sweat can occur and accumulate on the optical window, leading to optical losses and measurement variations. Therefore, in some examples, a hydrophobic optically-transparent coating can be added to the optical window outer side to fight water accumulation and prevent wetting. In other examples, one or more micro channels (e.g., microfluidic channels) engraved in the optical window can be used to displace the water quickly.

FIGS. 20B-20D are diagrams illustrating an optical window 2006 of the spectral analyzer including microfluidic channels 2008 according to some aspects. FIG. 20B is a top view of the optical window 2006 including the microfluidic channels 2008, while FIG. 20C is a side view of the optical window 2006 including the microfluidic channels 2008. As shown in FIG. 20D, when skin 2010 comes into contact with the optical window 2006, sweat droplets 2012 may start to accumulate on the surface of the optical window 2006. The microfluidic channels 2008 within the optical window 2006 may be configured to remove the sweat droplets 2012, for example, using a capillary tube effect, from the skin 2010. In some examples, the water absorbed by the microfluidic channels 2008 can be displaced to the thermal heat sink. The heat generated at the heat sink may be used to dry the accumulated water continuously. In other examples, a super-absorbent polymer or water-absorbing material can be used to absorb and retain the water. In still other examples, an amount of sweat droplets 2012 can be measured with a sensor coupled to the microfluidic channels 2008 to predict one or more analytes. The reading of this sensor can then be fed to the AI engine to improve and assist the spectral sensor results.

Given the complexity of human body metabolism process and the variations occurring along the day, and variations from person to person, the spectral analyzer may include supporting sensors to improve prediction by AI engine. FIGS. 21A-21C are diagrams illustrating the integration of sensors 2104a-2104d within a spectral analyzer 2100 according to some aspects. In the example shown in FIGS. 21A-21C, the sensors 2104a-2104d are shown integrated around an optical window 2102 of the spectral analyzer 2100. The sensors 2104a-2104d may further be electrically connected to the main electronic substrate (e.g., mother board), not shown for simplicity.

Supporting sensors 2104a-2104d may include, for example, a pressure/force sensor, a temperature sensor, a bio-impedance sensor, a hydration sensor, a heart rate sensor, an ECG, a blood pressure sensor, and other suitable sensors that can improve the performance of the AI engine. For example, sensor data provided by the sensors 2104a-2104d to the AI engine may enable the AI engine to compensate for background variations that do not correlate with the chemical content or analyte of interest. For example, pressure on the skin may affect the scattering properties of the light. A pressure sensor may be used to calibrate for this effect. In addition, the hydration level of the subject may affect the absorption properties of the skin. A hydration sensor may be used to calibrate for this effect. Furthermore, the temperature of the environment in addition to the body temperature can be fed to the AI engine.

Figure 22:
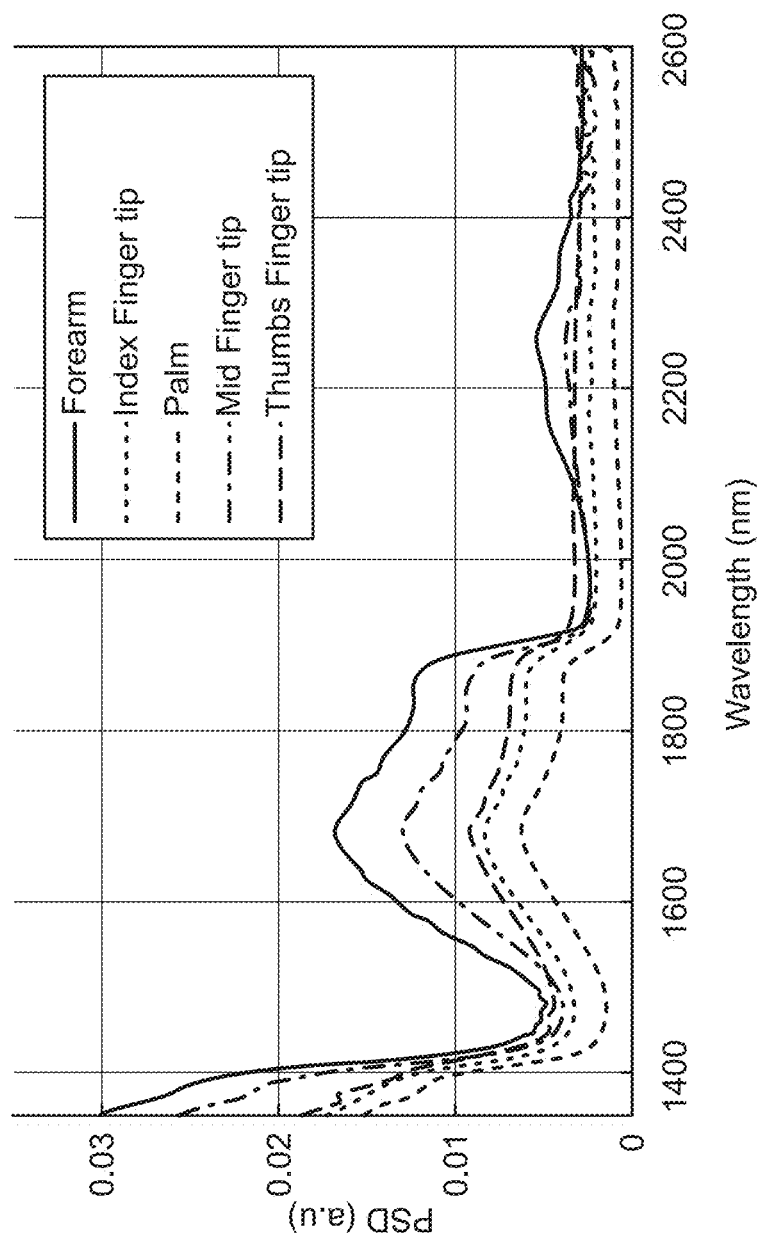
FIG. 22 is a graph illustrating examples of different spectra measured from different body locations according to some aspects.

Another supporting sensor can include a secondary spectral sensor (not shown) that can measure a spectrum of the sample in another spectral range. In addition, an imaging sensor (e.g., a camera) can be used to determine the location of the measurements on the body and the location may be used by the AI engine to select between different calibration models. FIG. 22 is a graph illustrating examples of different spectra measured from different body locations. Therefore, identifying the particular body location using, for example, an imaging sensor may improve the accuracy of any result produced by the AI engine.

In some examples, proper optical alignment of the different optical components may be dependent upon various degrees of freedom to actively align for maximum light coupling. Some movement allowances (tolerances) in the optical components during the assembly process may provide for better optical performance.

Figure 23A:
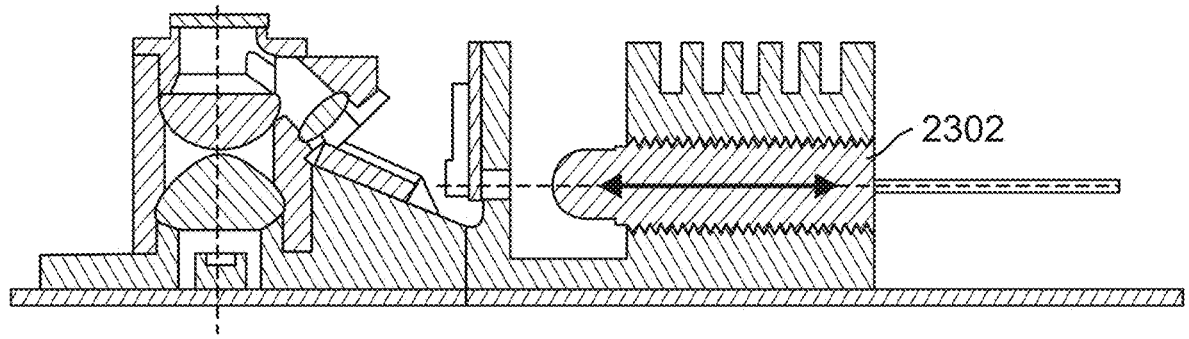
FIGS. 23A and 23B are diagrams illustrating an example of optical alignment of a light source of the spectral sensor according to some aspects.
Figure 23B:
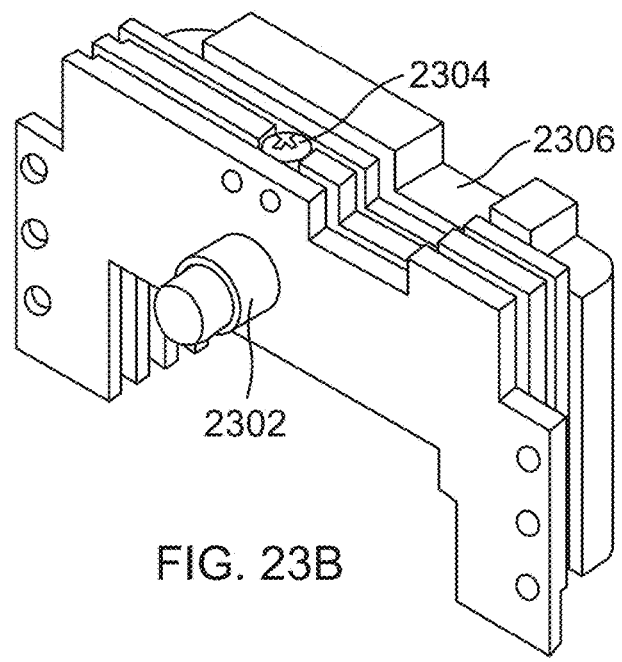

FIGS. 23A and 23B are diagrams illustrating an example of optical alignment of a light source 2302 of the spectral sensor according to some aspects. The light source 2302 may suffer from inaccuracy in the filament position. To overcome this issue, during the alignment, the light source 2302 may be able to be adjusted forward and backward until reaching the desired performance. For example, a threaded hole 2304 in a light source housing 2306 containing the light source 2302 may be used to provide optimization of the position of the light source 2302 with respect to other optical components in the spectral sensor.

FIGS. 24A-24C are diagrams illustrating an example of optical alignment of a substrate 2402 of a light modulation chip of a spectral sensor according to some aspects. In the example shown in FIGS. 24A-24C, the substrate 2402 (e.g., daughter board) may be adjustable for improved optical coupling of the light modulation chip attached thereto. For example, springs 2404 may be installed between the daughter board 2402 and the chassis 2408 to enable the daughter board 2402 to be tilted in a vertical direction for optical alignment of the light modulation chip. Screws 2406 (e.g., machine screws) for attaching the daughter board 2402 to the chassis 2408 may be threaded through the springs 2404 to facilitate adjustment of the daughter board 2402 using the springs 2404. For example, by loosening or tightening the machine screws 2406, the daughter board 2402 may be tilted from a corner side. The optimum tilting angle for optical coupling may be ascertained during assembly.

Figure 25:
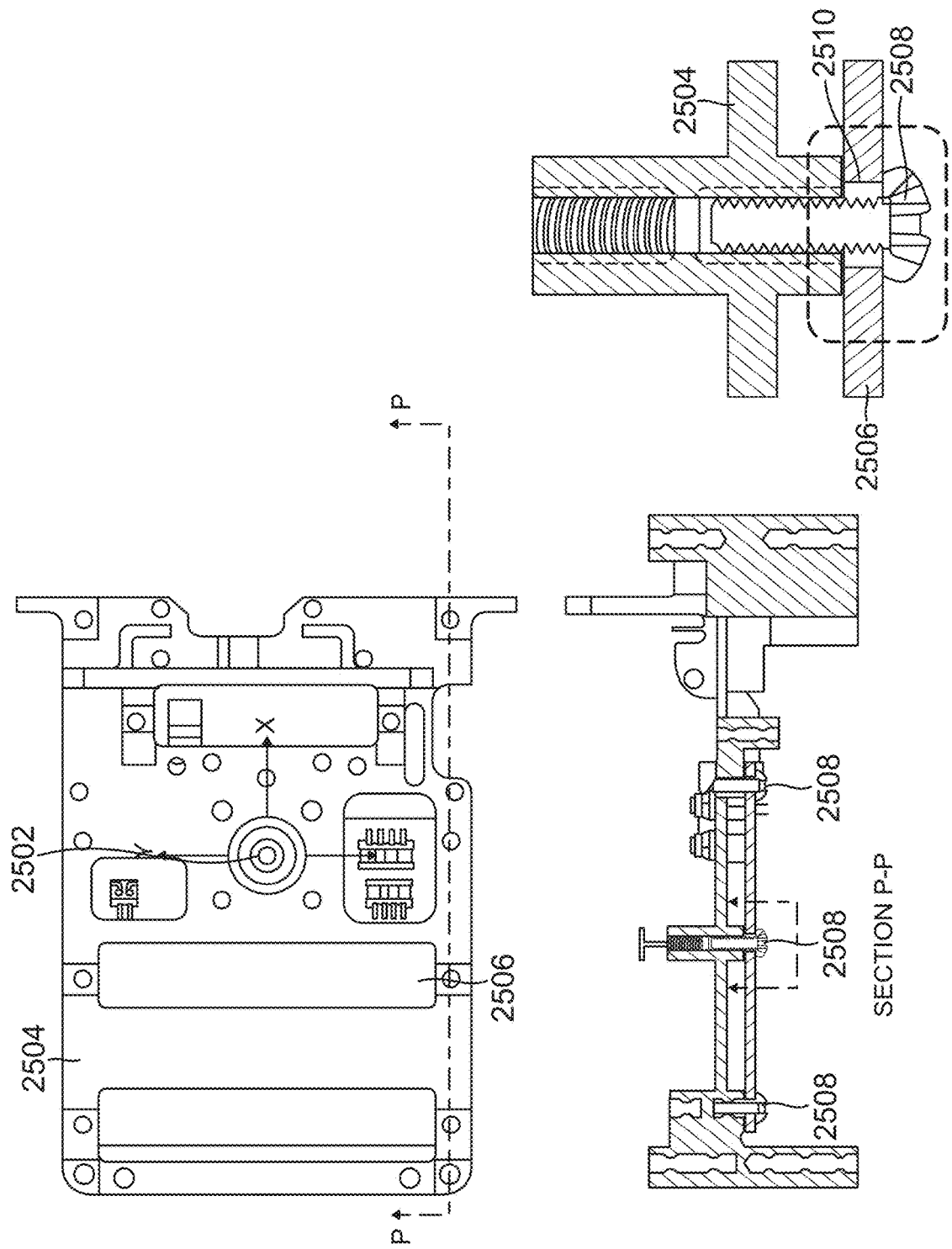
FIG. 25 is a diagram illustrating an example of optical alignment of a detector of a spectral sensor according to some aspects.

FIG. 25 is a diagram illustrating an example of optical alignment of a detector 2502 of a spectral sensor according to some aspects. The detector 2502 may be attached to a main electronic substrate 2506 (e.g., mother board). The mother board 2506 may be attached to the main chassis 2504 via machine screws 2508. The detector 2502 may be adjusted, for example, in X and Y directions for optical alignment of the detector using the screws 2508. For example, holes 2510 in the mother board 2506 configured to receive the machine screws 2508 may provide a clearance between the machine screw 2508 and the hole 2510 to allow for adjustment of the detector 2502 in the X and Y directions. Once the optimum alignment is achieved, the screws 2508 can be tightened and fixed according to that optimum position.

Figure 26A:
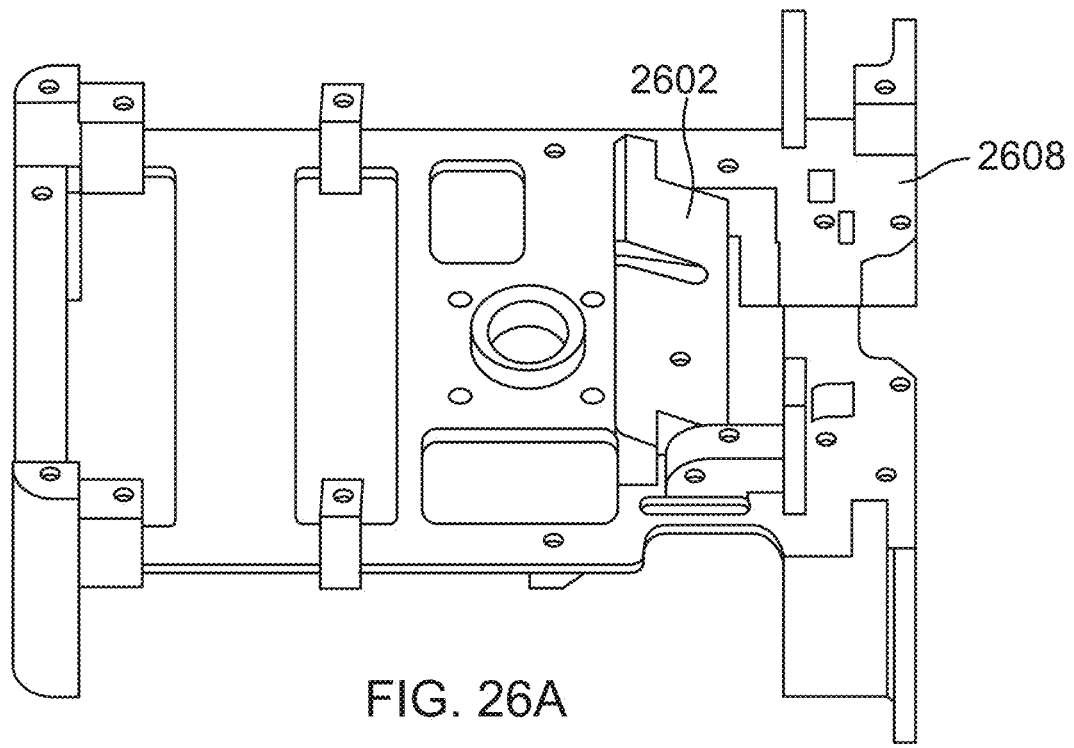
FIGS. 26A and 26B are diagrams illustrating an example of optical alignment of an illumination optical element of a spectral sensor according to some aspects.
Figure 26B:
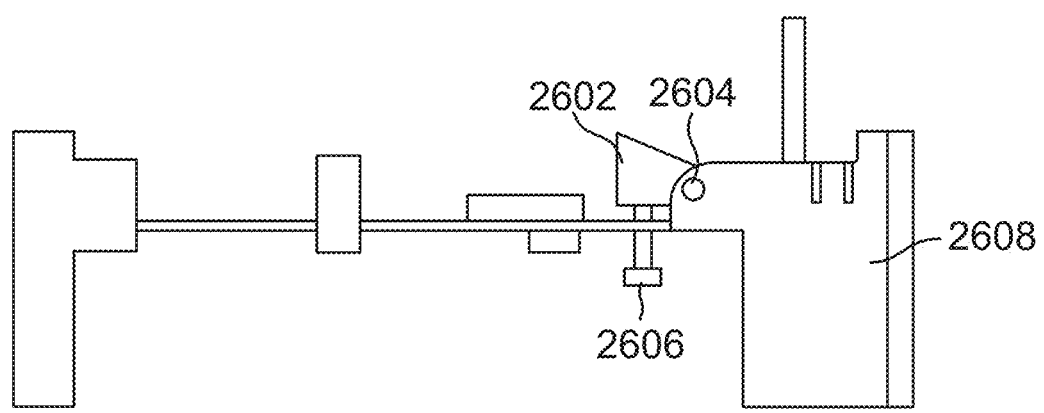

FIGS. 26A and 26B are diagrams illustrating an example of optical alignment of an illumination optical element (e.g., a redirecting mirror or folding mirror) 2602 of a spectral sensor according to some aspects. FIG. 26A is a top view of a chassis 2608 including the redirecting mirror 2602, while FIG. 26B is a side view of the chassis 2608 including the redirecting mirror 2602. In the example shown in FIGS. 26A and 26B, the redirecting mirror 2602 may be enabled to be rotated for optical alignment of the redirecting mirror 2602, thus improving optical performance. For example, the redirecting mirror 2602 may be attached to the chassis 2608 via a hinge 2604 and may further be resting on a screw 2606 that may be screwed/unscrewed from the bottom during the alignment process, thus causing an angle of the redirecting mirror 2602 to be modified in a controlled manner. The screw 2606 in combination with the hinge 2604 may therefore be considered as a rotating hinge for optical alignment of the redirecting mirror 2602.

Figure 27:
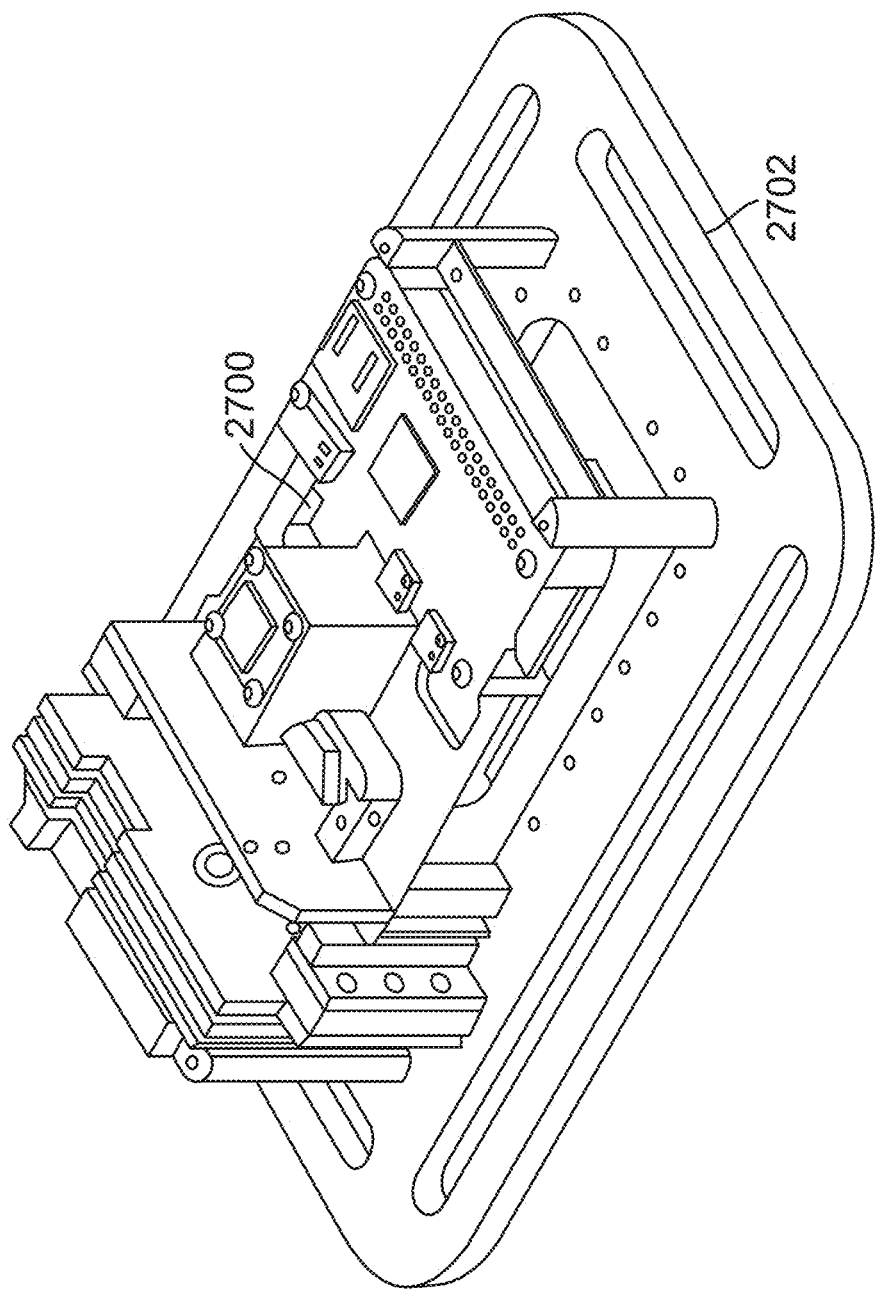
FIG. 27 is a diagram illustrating an example of an assembly mechanism for assembling a spectral analyzer according to some aspects.

FIG. 27 is a diagram illustrating an example of an assembly mechanism for assembling a spectral analyzer 2700 according to some aspects. In the example shown in FIG. 27, an accessory 2702 may be used to assemble the spectral analyzer 2700 on, for example, an assembly workspace or optical table. The accessory 2702 facilitates access to the spectral analyzer 2700 from the bottom side freely without barriers. The accessory 2702 may further be used for assembly of a prototype on an optical table, such that the alignment can be tuned actively while measuring a sample.

To calibrate the spectral sensor, a laser source may be included in the light modulator (e.g., an FTIR interferometer) to determine the mirror position by injecting the light into an auxiliary interferometer having the same movable mirror of the main interferometer and detecting the zero crossings of the resulting interference pattern, such that every two consecutive zero crossings correspond to an optical path difference OPD of known half wavelength 212.

In other examples, a technique based on capacitive sensing of the MEMS actuator motion may be used to determine optical path difference. In this example, laser or a narrow-band light may be used to calibrate the capacitive sensing technique just once, by detecting interferogram current and sensing capacitance variation simultaneously. Capacitance to OPD relation may then be extracted and saved as a look-up table on a storage chip in the spectral sensor.

Figure 28B:
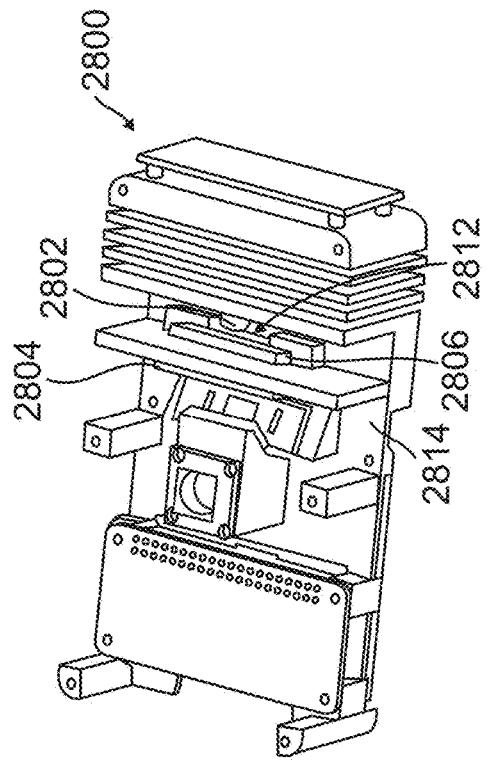
FIGS. 28A-28D are diagrams illustrating an example for calibration of a spectral analyzer based on capacitive sensing according to some aspects.
Figure 28D:
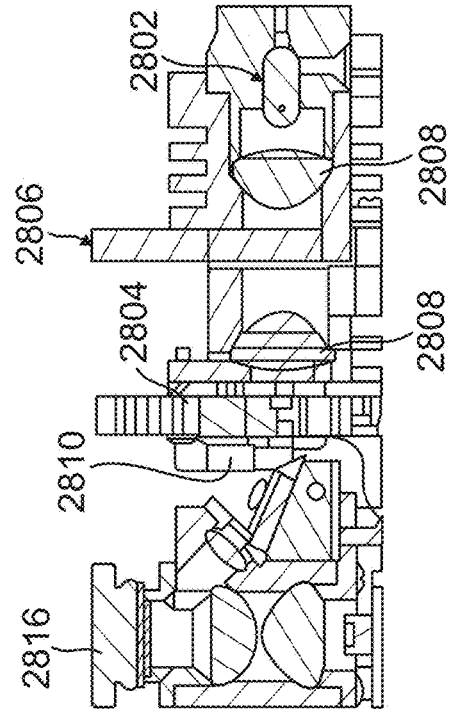
Figure 28A:
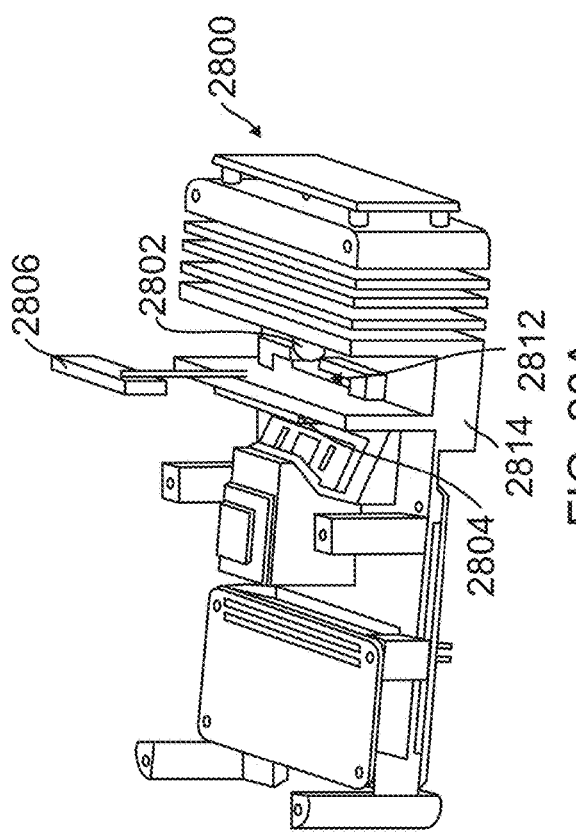
Figure 28C:
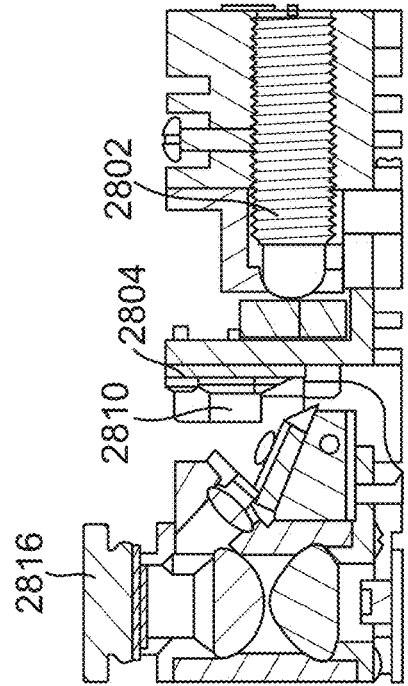

FIGS. 28A-28D are diagrams illustrating an example for calibration of a spectral analyzer 2800 based on capacitive sensing according to some aspects. In the example shown in FIGS. 28A-28D, a narrow-band optical band-pass filter (or reference material) 2806 can be used to calibrate the spectral analyzer 2800, by inserting the band-pass filter (or reference material) 2806 in front of a light source 2802 in the light path between the light source 2802 and a daughter board 2804 having a light modulator 2810 attached thereto. For example, the band-pass filter 2806 may be removably inserted into a cavity 2812 formed in a chassis 2814 of the spectral analyzer 2800. In some examples, the reference material 2806 may be used for wavelength error correction, based on the wavelength position of known absorption lines across the spectral range In some examples, as shown in FIG. 28D, a two-lens system 2808 can be used to maximize the coupling efficiency from the light source 2802 to the light modulator 2810, while collimating the light in the space between the two lenses 2808, where the filter is inserted. In addition, as shown in FIGS. 28C and 28D, a reference material 2816 can be placed over the optical window of the spectral analyzer 2800 (e.g., in addition to the band-pass filter/reference material 2806 inserted between the light source and the light modulator or in lieu of the band-pass filter/reference material 2806), thus enabling measurement of the reflectance of the reference material 2816 in reflection mode or transmittance in trans-reflection mode, depending on the material properties, whether liquid or solid.

Figure 29:
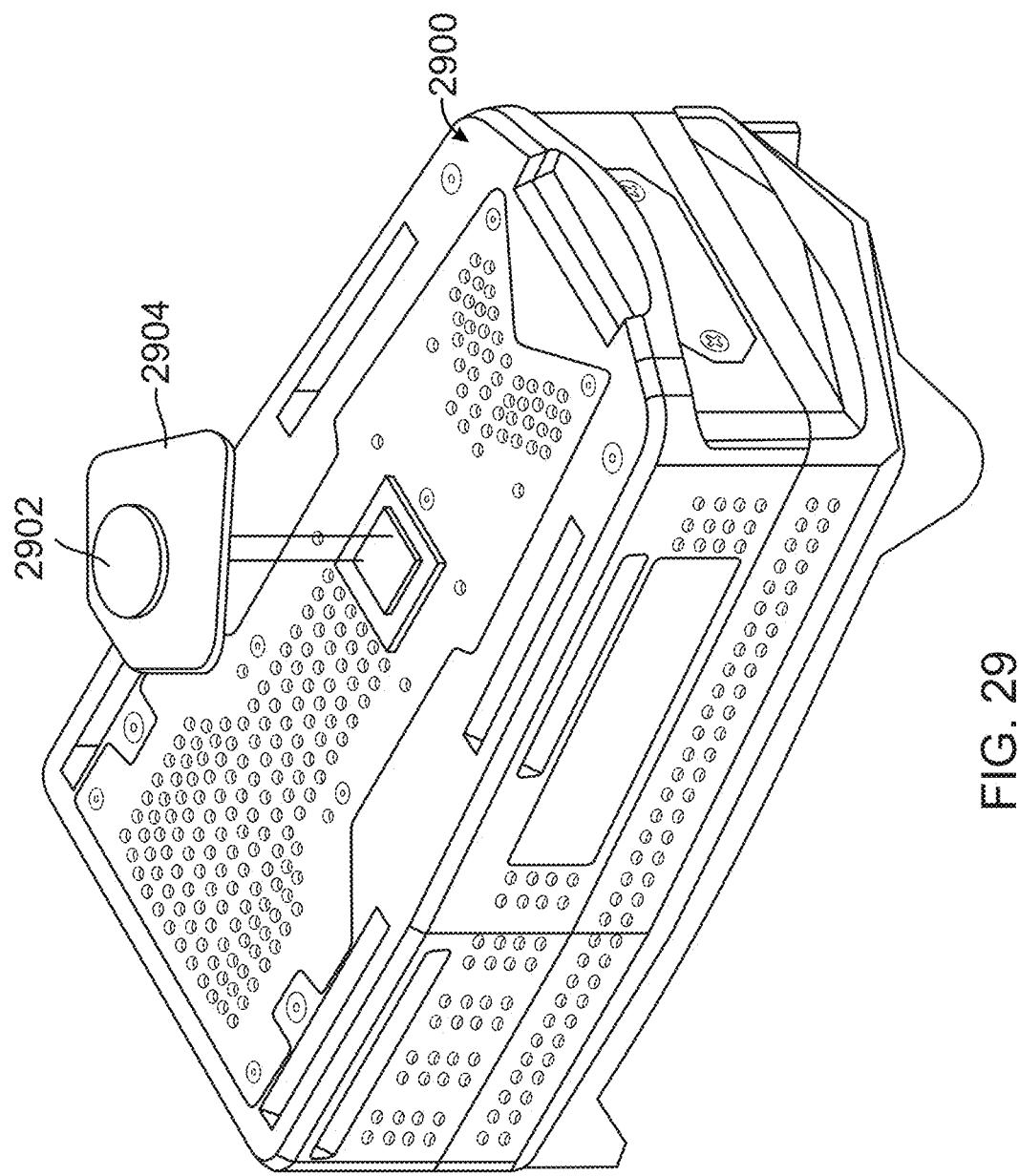
FIG. 29 is a diagram illustrating another example for calibration of a spectral analyzer according to some aspects.

FIG. 29 is a diagram illustrating another example for calibration of a spectral analyzer 2900 according to some aspects. In the example shown in FIG. 29, a reference material 2902 can be attached to a magnetic cover 2904 to be attached to the top side (e.g., above an optical window) of the spectral analyzer 2900. In some examples, the reference material 2902 can be a highly reflective PTFE tile, partially reflective carbon-doped grey/dark PTFE tile, a Teflon sheet, or a ceramic tile, to be used for measuring the instrument spectral response taking a single beam/background spectrum measurement before measuring the sample under test. This allows extraction of the sample reflectance/transmittance.

In the examples shown in FIGS. 28A-28D and 29, other calibration lamps can be used as well for spectral calibration, such as rare gases excitation lamps, e.g., Krypton lamp, Xenon lamp, Neon lamp, and Argon lamp. The calibration lamp(s) can replace the main light source during calibration.

To accurately measure sample absorbance spectra, background measurements may be performed frequently or even before each sample measurement to be able to compensate for instrument response drifts, which consumes overhead time. In some examples, the spectral analyzer may be designed to reduce the time of the measurement process, while maintaining an online reference/background measurement to compensate for any power spectral density/intensity (y-axis) drifts.

Figure 30:
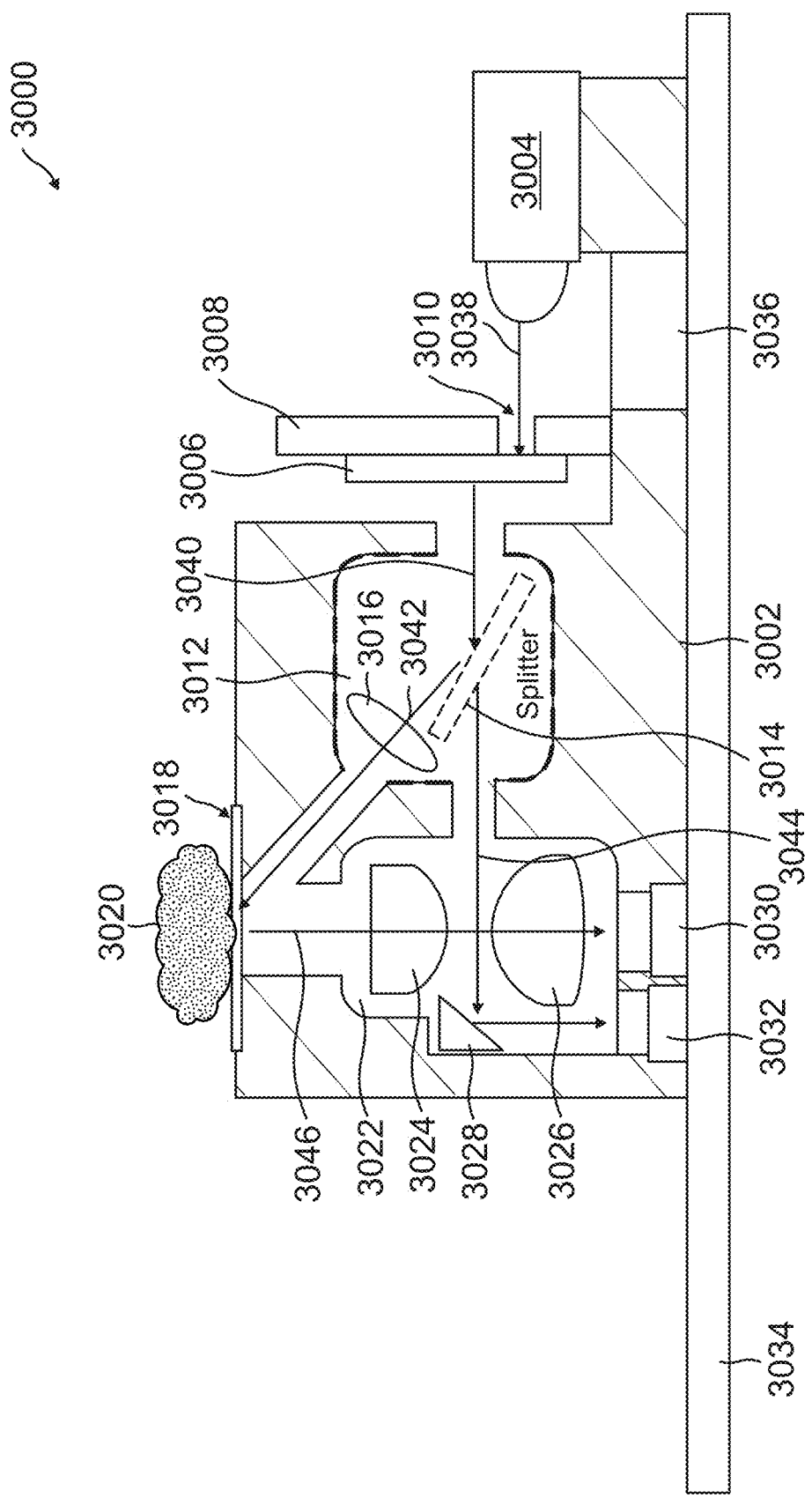
FIG. 30 is a diagram illustrating an example of a self-referencing configuration of a spectral sensor of a spectral analyzer for obtaining a reference measurement according to some aspects.

FIG. 30 is a diagram illustrating an example of a self-referencing configuration of a spectral sensor 3000 of a spectral analyzer for obtaining a reference measurement according to some aspects. The spectral sensor 3000 includes a chassis 3002 that is configured to both align and connect together various components, including, for example, a light source 3004, a light modulator 3006, illumination optical element(s) 3012, collection optical element(s) 3022, and a detector 3030. An optical window 3018 is positioned on a top surface of the spectral sensor 3000 and is configured to receive a sample 3020 (e.g., a biological sample) on an external surface thereof. In some examples, the light modulator 3006 may be implemented on a light modulation chip (e.g., a MEMS chip). The light modulation chip is shown attached to a substrate 3008 (e.g., a daughter board) The daughter board 3008 is assembled on the chassis 3002 and provides a connection between the light modulation chip 3006 and an electronic board substrate (e.g., mother board) 3034. In addition, the detector 3030 may further be attached to the mother board 3034. In addition, a thermal separator 3036 may be positioned between the light modulator/daughter board 3006/3008 and the light source 3004.

In an example operation, the light source 3004 may be configured to produce input light 3038. An aperture 3010 in the daughter board 3008 may be configured to pass a first portion of the input light 3038 and block a second portion of the input light 3038 corresponding to the non-useful rays. The light modulator 3006 is configured to receive the first portion of the input light 3038 and to produce modulated light 3040 based on the input light 3038 that is directed towards the illumination optical element(s) 3012.

In the example shown in FIG. 30, a beam splitter 3014 can be used in the illumination optical element(s) 3012 instead of a folding mirror to split the modulated light 3040 into first modulated light 3042 and second modulated light 3044. The first modulated light 3042 may then be directed by a focusing lens 3016 within the illumination optical element(s) 3012 to the optical window 3018 for interaction with the sample 3020 to produce output light 3046 (e.g., reflected scattered light) in a reflection mode. The output light 3046 is coupled to the detector 3030 using the collection optical element(s) 3022. The detector 3030 may be configured to produce an output signal based on the output light 3046 from which spectral data corresponding to a spectrum of the sample 3020 may be obtained. In the example shown in FIG. 30, the collection optical element(s) 3022 include a two-lens system 3024 and 3026.

The second modulated light 3044 is directed to a secondary detector 3032 on the mother board 3034 adjacent the main detector 3030, using, for example, an auxiliary reflector 3028 to obtain a reference spectrum. The second modulated light 3044 may be considered reference/background light, which may be detected simultaneously with the output light 3046 by the secondary detector 3032. This allows self-referencing of the spectral analyzer without the need for manual measurement of the background at different times. Ratioing the measured main beam spectrum (e.g., based on the output light 3046) to the secondary beam spectrum (e.g., based on the second modulated light 3044) may enable compensation of the light source response and the light modulation chip response. In some examples, the two detectors 3030 and 3032 can be selected to be of the same type in order to minimize the differences especially in the thermal drift response. The residual difference in the response of the two light paths (main and secondary) can further be calibrated on the production line, as described above, by placing a reference reflectance standard (Spectralon/PTFE/Ceramic tile) on the optical window 3018 and extracting the ratio between the two light paths.

Figure 31:
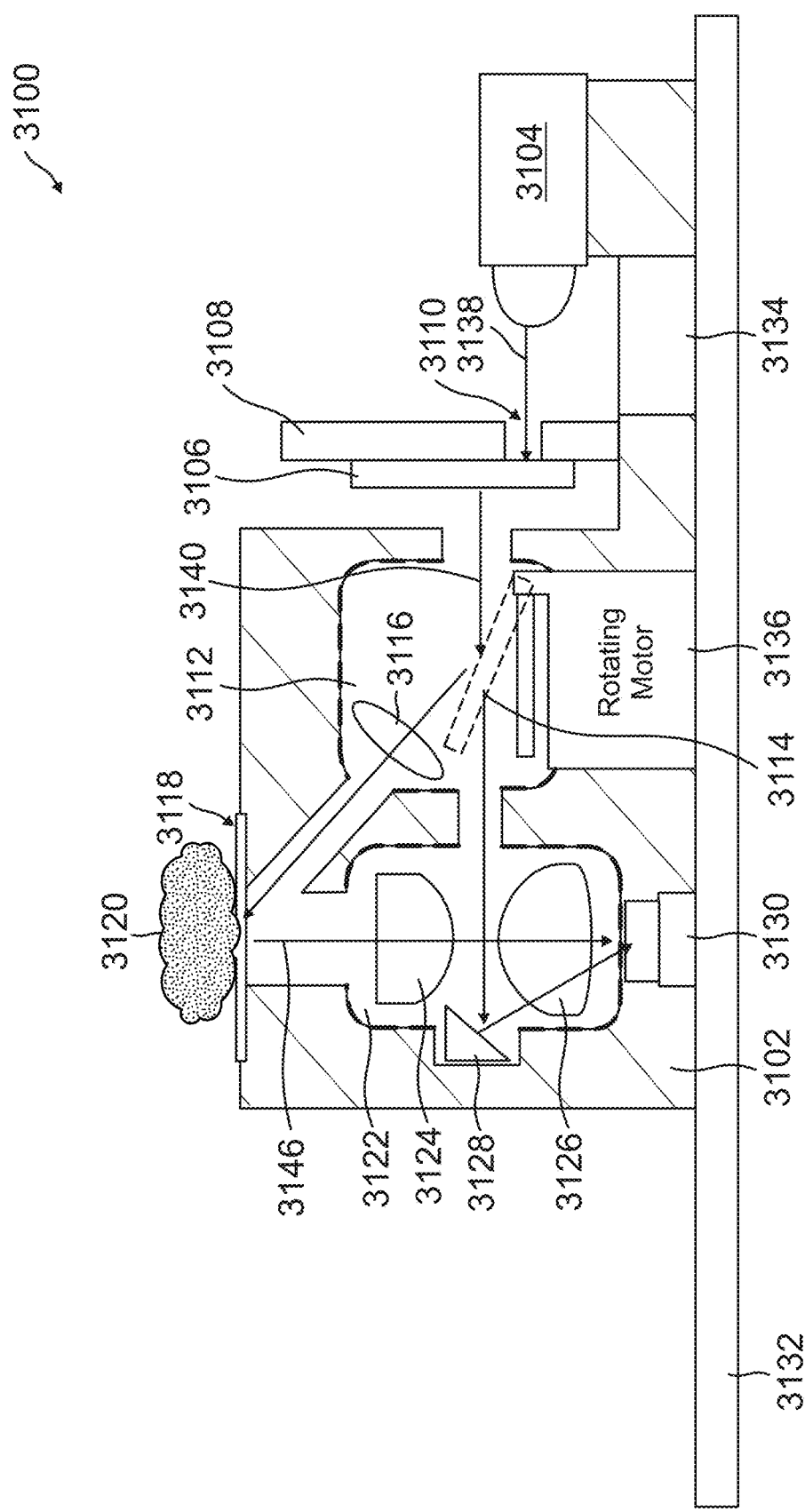
FIG. 31 is a diagram illustrating another example of a self-referencing configuration of a spectral sensor of a spectral analyzer for obtaining a reference measurement according to some aspects.

FIG. 31 is a diagram illustrating another example of a self-referencing configuration of a spectral sensor 3100 of a spectral analyzer for obtaining a reference measurement according to some aspects. The spectral sensor 3100 includes a chassis 3102 that is configured to both align and connect together various components, including, for example, a light source 3104, a light modulator 3106, illumination optical element(s) 3112, collection optical element(s) 3122, and a detector 3130. An optical window 3118 is positioned on a top surface of the spectral sensor 3100 and is configured to receive a sample 3120 (e.g., a biological sample) on an external surface thereof. In some examples, the light modulator 3106 may be implemented on a light modulation chip (e.g., a MEMS chip). The light modulation chip is shown attached to a substrate 3108 (e.g., a daughter board) The daughter board 3108 is assembled on the chassis 3102 and provides a connection between the light modulation chip 3106 and an electronic board substrate (e.g., mother board) 3132. In addition, the detector 3130 may further be attached to the mother board 3132. In addition, a thermal separator 3134 may be positioned between the light modulator/daughter board 3106/3108 and the light source 3104.

In an example operation, the light source 3104 may be configured to produce input light 3138. An aperture 3110 in the daughter board 3108 may be configured to pass a first portion of the input light 3138 and block a second portion of the input light 3138 corresponding to the non-useful rays. The light modulator 3106 is configured to receive the first portion of the input light 3138 and to produce modulated light 3140 based on the input light 3138 that is directed towards the illumination optical element(s) 3112.

In the example shown in FIG. 31, the illumination optical element(s) 3112 may include a folding mirror (e.g., redirecting mirror) 3114 and a focusing lens 3116. The folding mirror 3114 may be coupled to a rotating motor 3136 to rotate the folding mirror 3114, switching the redirecting mirror 3114 from a main light path in a measurement mode to a secondary light path in a reference mode. In the measurement mode, the rotating motor 3136 is configured to rotate the redirecting mirror 3114 to a first position at which the modulated light 3140 is directed towards the optical window 3118 via the focusing lens 3116 for interaction with the sample 3120 to produce output light 3146 (e.g., reflected scattered light) in a reflection mode. The output light 3146 is coupled to the detector 3130 using the collection optical element(s) 3122. The detector 3130 may be configured to produce an output signal based on the output light 3146 from which spectral data corresponding to a spectrum of the sample 3120 may be obtained. In the example shown in FIG. 31, the collection optical element(s) 3122 include a two-lens system 3124 and 3126.

In the reference mode, the rotating motor 3136 is configured to rotate the redirecting mirror 3114 to a second position at which the modulated light 3140 is directed towards the detector 3130 without interacting with the sample 3120 to obtain a reference spectrum. The modulated light 3144 is directed to detector 3130 using, for example, an auxiliary reflector 3128. Thus, in the example shown in FIG. 31, self-referencing can be performed with a single detector 3130 by using the rotating motor 3136 to rotate the redirecting mirror 3114 between the first position and the second position. For example, the redirecting mirror 3114 can rotate to a horizontal state in the second position to allow the output modulated light 3140 of the light modulation chip 3006 to pass to the auxiliary reflector 3128, which reflects the light directly to the detector 3130 without passing through the sample 3120. In this example, control electronics (e.g., processor 432 shown in FIG. 4) may drive the rotating motor 3136 to switch from the main light path of the sample measurement mode to the secondary light path of the reference mode. For example, the switching operation can be performed electro-optically, instead of rotating a light-folding slab, such that the reflectivity of the mirror is controlled electrically. For the main path measurement, the redirecting mirror 3114 may be excited for high reflectivity to direct the light towards the sample 3120, while for secondary reference path measurement, the transmittance may be maximized.

Figure 32:
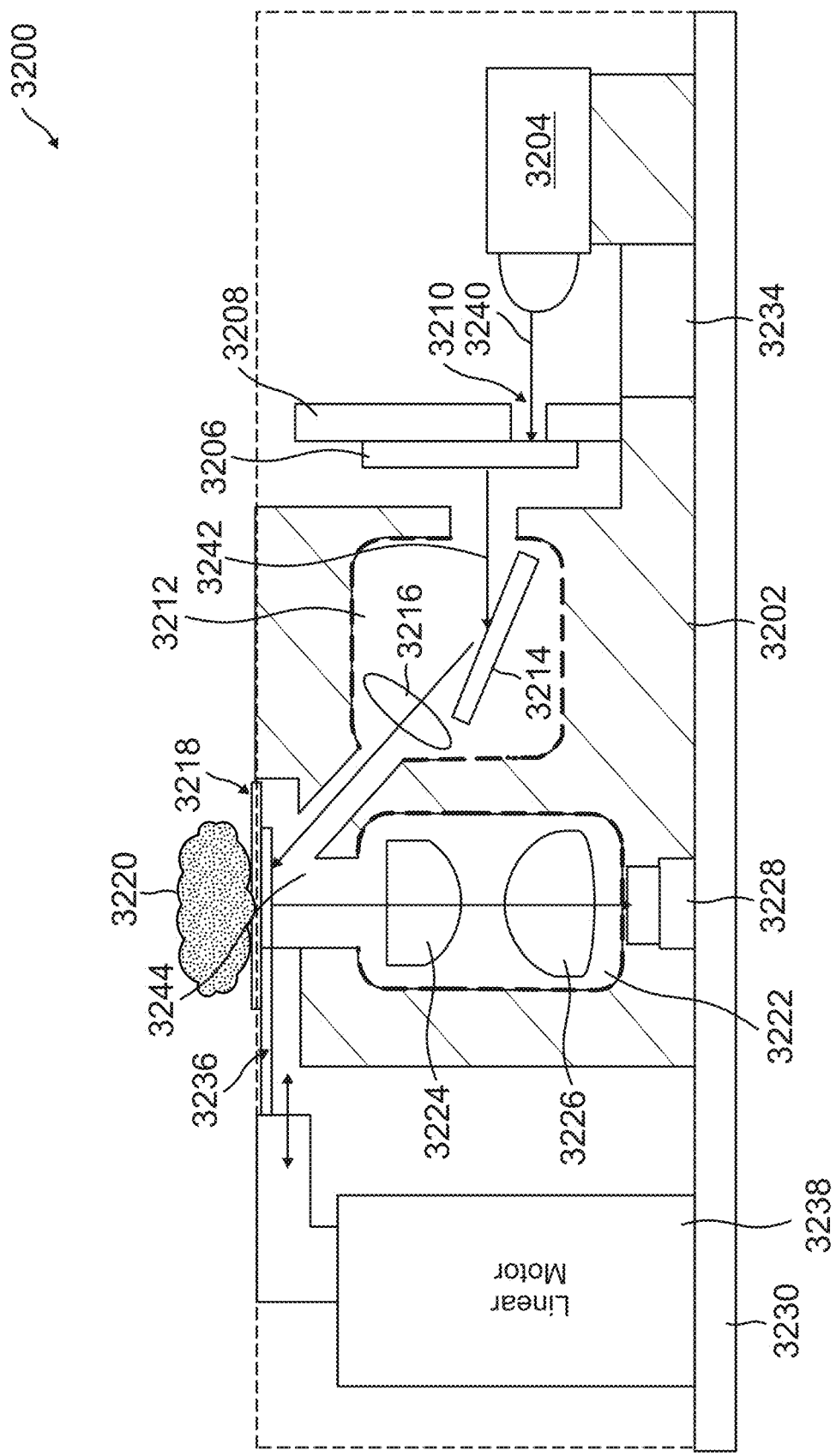
FIG. 32 is a diagram illustrating another example of a self-referencing configuration of a spectral sensor of a spectral analyzer for obtaining a reference measurement according to some aspects.

FIG. 32 is a diagram illustrating another example of a self-referencing configuration of a spectral sensor 3200 of a spectral analyzer for obtaining a reference measurement according to some aspects. The spectral sensor 3200 includes a chassis 3202 that is configured to both align and connect together various components, including, for example, a light source 3204, a light modulator 3206, illumination optical element(s) 3212, collection optical element(s) 3222, and a detector 3228. An optical window 3218 is positioned on a top surface of the spectral sensor 3200 and is configured to receive a sample 3220 (e.g., a biological sample) on an external surface thereof. In some examples, the light modulator 3206 may be implemented on a light modulation chip (e.g., a MEMS chip). The light modulation chip is shown attached to a substrate 3208 (e.g., a daughter board) The daughter board 3208 is assembled on the chassis 3202 and provides a connection between the light modulation chip 3206 and an electronic board substrate (e.g., mother board) 3230. In addition, the detector 3228 may further be attached to the mother board 3230. In addition, a thermal separator 3234 may be positioned between the light modulator/daughter board 3206/3208 and the light source 3204.

In an example operation, the light source 3204 may be configured to produce input light 3240. An aperture 3210 in the daughter board 3208 may be configured to pass a first portion of the input light 3240 and block a second portion of the input light 3240 corresponding to the non-useful rays. The light modulator 3206 is configured to receive the first portion of the input light 3240 and to produce modulated light 3242 based on the input light 3240 that is directed towards the illumination optical element(s) 3212, which may include, for example, a folding mirror (e.g., redirecting mirror) 3214 and a focusing lens 3216.

In the example shown in FIG. 32, self-referencing can be achieved using a tile 3236 having a reference material thereon. A linear motor 3238 is configured to switch between a measurement mode and a reference mode. In the reference mode, the linear motor 3238 is configured to move the tile 3236 to a first position under (beneath) the optical window 3218 to totally block the light path to the sample 3220. In this example, the redirecting mirror 3214 may be configured to direct the modulated light 3242 towards the tile 3236, where the modulated light 3242 is reflected by the tile 3236 (e.g., Spectralon/PTFE/Ceramic) and coupled to the detector 3228 via the collection optical element(s) 3222 to obtain a reference spectrum. For example, the collection optical element(s) 3222 can include a two-lens system 3224 and 3226.

In the measurement mode, the linear motor 3238 is configured to move the tile 3236 to a second position away from the optical window to allow the modulated light 3242 to be directed towards the optical window 3218 via the redirecting mirror 3214 and focusing lens 3216 for interaction with the sample 3220 to produce output light 3246 (e.g., reflected scattered light).

Building a robust calibration model for analyte detection or quantification in a biological tissue or skin may require including different concentrations covering the whole range at different controlled conditions. In some examples, it may be difficult to cover the whole range including extreme conditions by building the calibration model in-vivo. Therefore, in various aspects, the calibration model can be complemented by in-vitro measurements. In-vitro measurements further enables controlling multiple analytes independently.

Figure 33A:
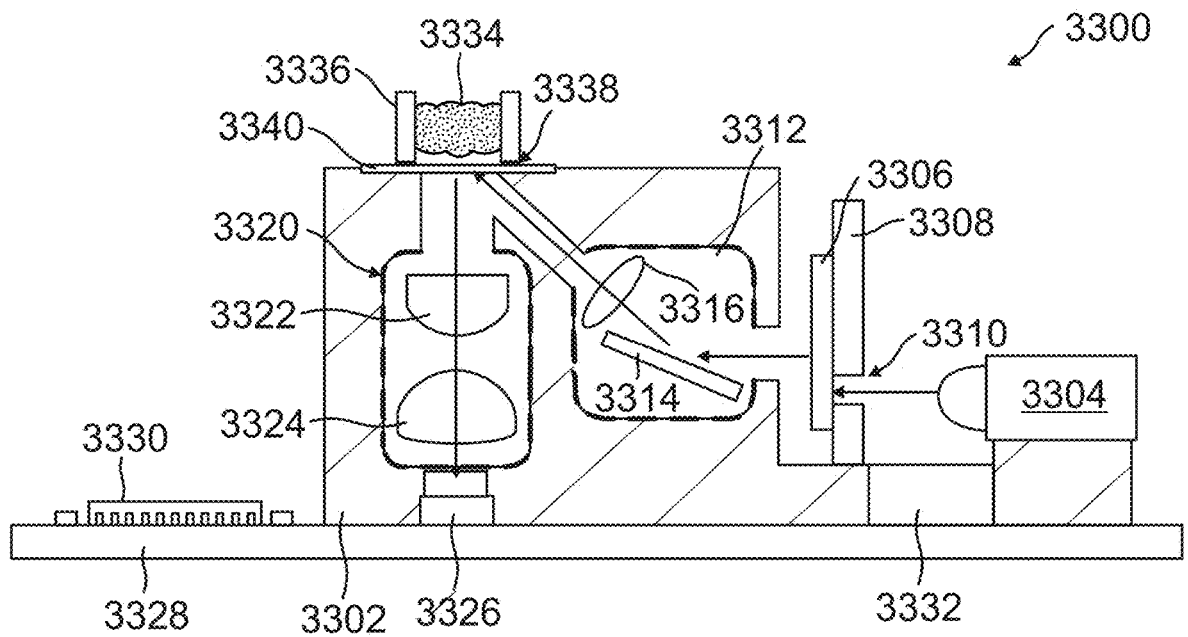
FIGS. 33A and 33B are diagrams illustrating example configurations of a spectral sensor of a spectral analyzer for testing of in-vitro samples according to some aspects.
Figure 33B:
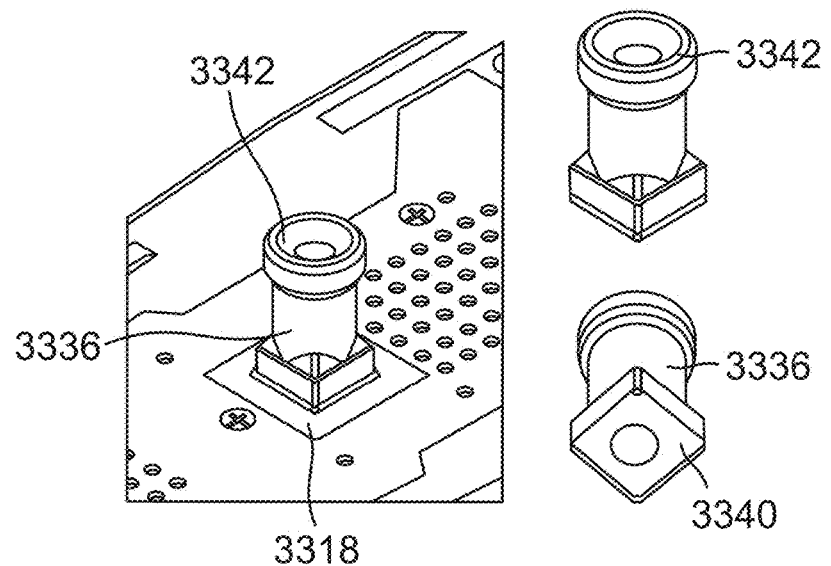

FIGS. 33A and 33B are diagrams illustrating example configurations of a spectral sensor 3300 of a spectral analyzer for testing of in-vitro samples according to some aspects. The spectral sensor 3300 includes a chassis 3302 that is configured to both align and connect together various components, including, for example, a light source 3304, a light modulator 3306, illumination optical element(s) 3312 (e.g., which may include a redirecting mirror 3314 and a focusing lens 3316), collection optical element(s) 3320 (e.g., which may include a two-lens system 3322 and 3324), and a detector 3326. An optical window 3318 (shown in FIG. 33B) may be positioned on a top surface of the spectral sensor 3300. In some examples, the light modulator 3306 may be implemented on a light modulation chip (e.g., a MEMS chip). The light modulation chip is shown attached to a substrate 3308 (e.g., a daughter board) The daughter board 3308 is assembled on the chassis 3302 and provides a connection between the light modulation chip 3306 and an electronic board substrate (e.g., mother board) 3328. In addition, the detector 3326 and a processor 3330 may further be attached to the mother board 3328. In addition, a thermal separator 3332 may be positioned between the light modulator/daughter board 3306/3308 and the light source 3304.

In the examples shown in FIGS. 33A and 33B, an in-vitro/phantom sample holder 3336 may be configured to contain a reference sample 3334. In some examples, multiple sample holders 3336 may be produced to contain different liquid samples, such that each sample is prepared and dispensed inside its own mini-holder 3336. Each holder 3336 may be in the form of a cylindrical container. The prepared samples 3334 can be stored inside the mini-holders 3336, which may each include a suitable cover 3342 for storing the samples 3334 at suitable storage temperatures.

The holder 3336 may be glued to an optical window 3340 using an epoxy 3338. The gluing epoxy 3338 prevents the liquid from leakage. In some examples, the optical window 3340 of the holder 3336 may be similar to the optical window 3318 of the spectral analyzer, such that optical window 3340 of the holder 3336 may replace the optical window 3318 of the spectral analyzer during in-vitro samples measurement, as shown in FIG. 33A. In other examples, the holder 3336 may be sealed using the optical window 3340 and the holder 3336 may be placed above the optical window 3318 of the spectral analyzer during in-vitro samples measurement, as shown in FIG. 33B. In either configuration shown in FIG. 33A or 33B, an input/output for replacing the in-vitro samples in automated manner can be also used.

Figure 34:
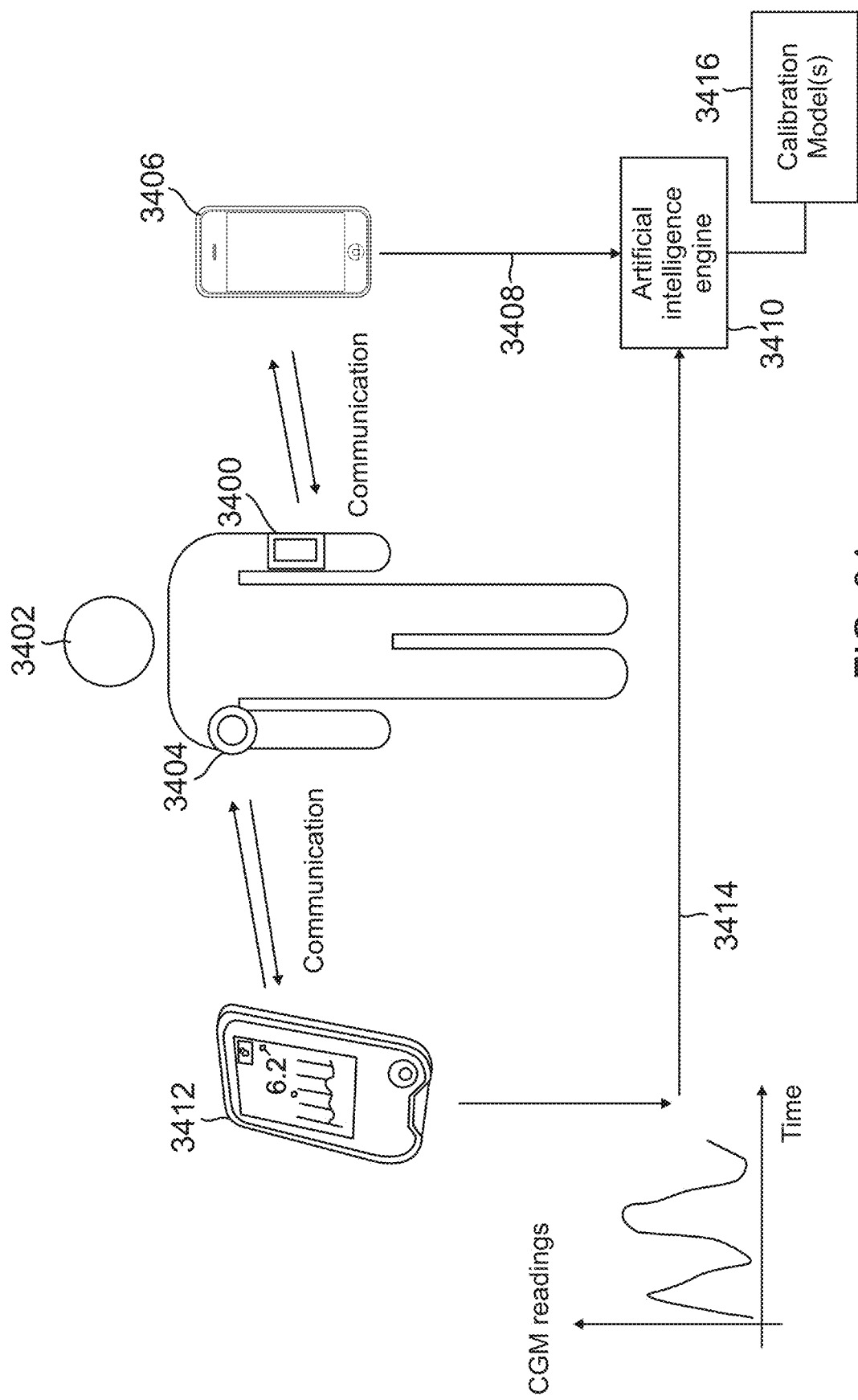
FIG. 34 is a diagram illustrating an example of calibration model building for a spectral analyzer according to some aspects.

FIG. 34 is a diagram illustrating an example of calibration model building for a spectral analyzer according to some aspects. The example shown in FIG. 34 is related to continuous monitoring applications, such as continuous glucose monitoring. However, the concepts illustrated in FIG. 34 may be applied to other applications. The calibration model building technique shown in FIG. 34 includes a spectral analyzer 3400 that may be coupled to a cloud-based AI engine 3410 via a communication device 3406 (e.g., a cellular phone or other device configured to provide spectral data obtained by the spectral analyzer 3400 to the AI engine 3410). The spectral analyzer 3400 may be, for example, a wearable device, as shown in FIG. 20A, that may be worn by a human subject 3402. For wearable applications and continuous measurements such as glucose measurement, stable locations with minimum movement such as the forearm may be suitable. The forearm also provides the highest signal level in this case based on the measurements. However, other applications may provide measurements from more accessible locations, such as the fingers. For these cases, the index finger knuckles may be chosen as they correspond to the location with the highest reflection and maximum stability. The palm of the hand may be used as well.

The AI engine 3410 may be configured to build a calibration model 3416 for continuous glucose monitoring using a reference technique, such as finger pricking on a frequent basis or using a minimally invasive sensor (e.g., sensor 3404), the latter being illustrated in FIG. 34. For example, the sensor 3404 may be a small disc (e.g., a continuous glucose monitoring (CGM) patch) with a needle that is placed on the upper arm of a human subject. The sensor 3404 may be wirelessly coupled to a reader 3412 to provide readings of the glucose in the interstitial fluid obtained by the sensor 3404. The reader 3412 may further be in wireless communication with the AI engine 3410 to provide the glucose readings (e.g., CGM readings) 3414 of the sensor 3404. The delay/offset between the glucose readings of the blood and the interstitial fluid can be accounted for in the AI engine 3410.

In addition, the spectral analyzer 3400 may further provide spectral data 3408 obtained at the same time as the glucose readings to the AI engine 3410 via the communication device 3406 to build the calibration model 3416 for the spectral analyzer 3400. In some examples, the interferometer peak-to-peak value may gradually decay at the beginning and eventually reach a stable point. This decay in amplitude may be the result of the increase of skin tissue hydration by the accumulation of sweat because of the skin-glass interface. Therefore, in some examples, the AI engine 3410 may be configured to wait for a predefined period of time until the measurement stabilizes before initiating the calibration model building process.

In some examples, the calibration model 3416 can be customized per person (e.g., may be built specific to each human subject 3402) by using the readings of the sensor 3404 as a reference to teach the machine learning/AI engine 3410. In some examples, the sensor 3404 can be used for a number of days to account for different conditions, such as activities and meals. In addition, motion artifacts resulting from movement of the human subject 3402 can be easily detected by the monitoring of the continuous spectrum power, as there is an abrupt change in the power at the instant of movement. Once the calibration model 3416 is built, the sensor 3404 may be removed and the spectral analyzer 3400 may be worn instead of the sensor 3404 to predict the glucose values. In continuous glucose monitoring applications, another information of high importance is whether the glucose is increasing or decreasing. The AI engine 3410 using the calibration model 3416 may further be used to provide a prediction of the direction of glucose change. To overcome an aging effect, the sensor 3404 can be worn from time to time to correct for the bias/errors or to update the calibration model 3416 with any biological changes that occurred in the person under test.

Moreover, in examples in which the calibration model 3416 is not unique to one person (e.g., the calibration model may be a universal/global calibration model to be applied to multiple human subjects 3402), there may exist amplitude variations between each measurement that results from the variation from the skin from one person to another. In some examples, these variations can be compensated for by one or more sensors (e.g., as shown in FIG. 3).

Figure 35:
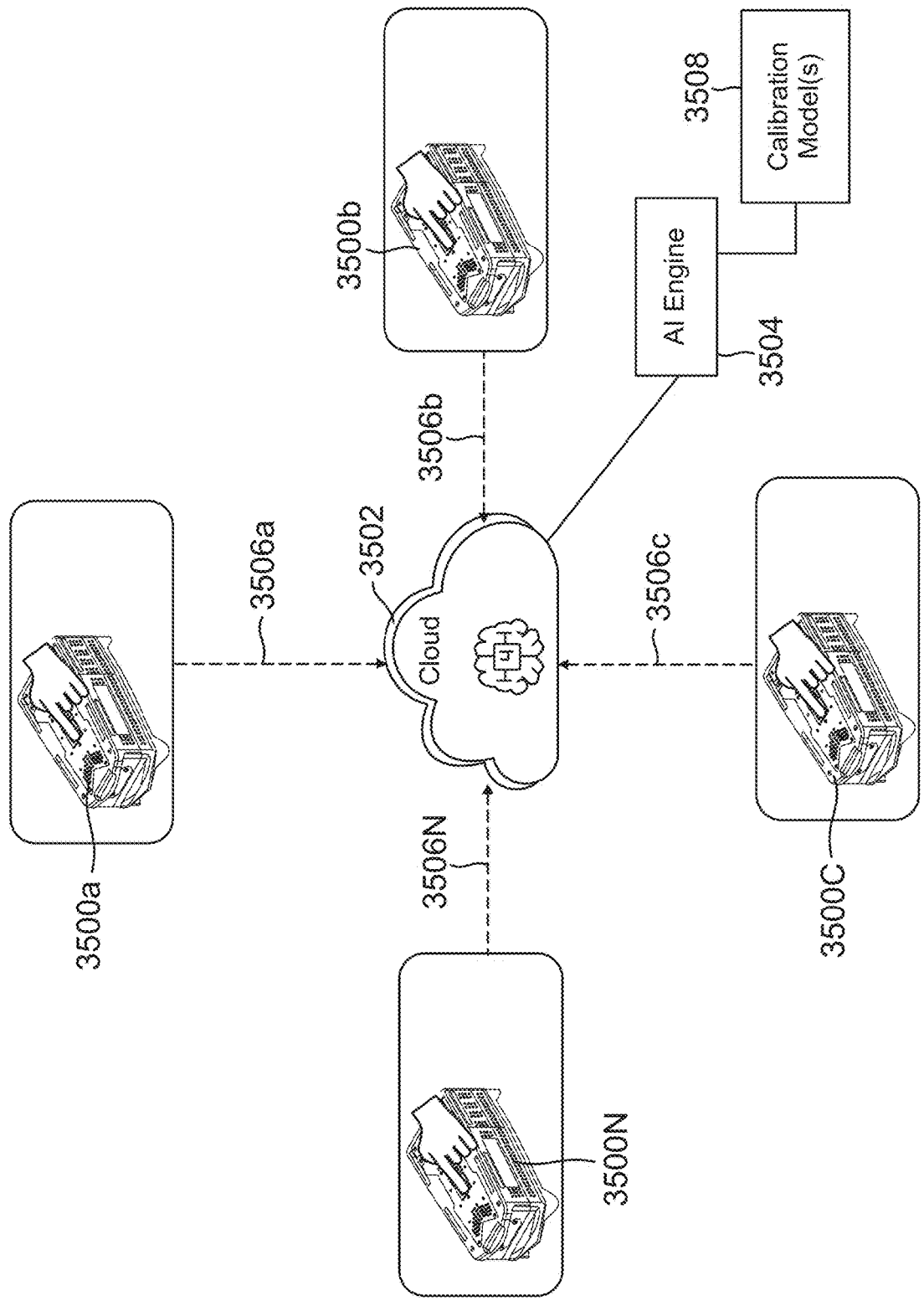
FIG. 35 is a diagram illustrating another example of calibration model building for a spectral analyzer according to some aspects.

FIG. 35 is a diagram illustrating another example of calibration model building for a spectral analyzer according to some aspects. In the example shown in FIG. 35, multiple spectral analyzers 3500a, 3500b, 3500c, ..., 3500N may be installed in various locations, and each of the spectral analyzers 3500a ... 3500N may be connected to the cloud 3502 for communication with a cloud-based AI engine 3504. For example, each of the spectral analyzers 3500a, 3500b, 3500c, ..., 3500N may be configured to provide respective spectral data 3506a, 3506, 3506c, ..., 3506N to the cloud-based AI engine 3504 to enable the AI engine 3504 to build a calibration model 3508.

In some examples, each of the spectral analyzers 3500a ... 3500N may be located within a respective analysis laboratory, which may further collect and provide reference values to the AI engine 3504 (e.g., similar to the example shown in FIG. 34). For example, while collecting blood samples from patients, the spectral analyzers 3500a ... 3500N may be used to simultaneously take a respective measurement of a respective patient's skin though finger, forearm, etc. Different blood analysis parameters may then be uploaded to the AI engine 3504 via the cloud, along with the measured spectral data 3506a ... 3506N and the patient's' information. The AI engine 3504 may then use the uploaded data to build multi-variate calibration model(s) 3508, with continuous improvement with the number of patients being measured.

In other examples, the spectral analyzers 3500a ... 3500N may be located within vehicles that can be connected to the cloud 3502 to provide measured spectral data of skin. In addition, each vehicle may further include a breath analyzer configured to provide reference breath analyzer alcohol concentrations and driver information to the AI engine 3504. The AI engine 3504 may then build calibration model(s) 3508 for the alcohol concentration in blood, and continuously update the calibration model(s) 3508 based on additional sensor and reference data being collected.

In some examples, a global calibration model 3508 can be built for different skin locations. In this example, the AI engine 3504 can automatically recognize the location from the spectrum measured and use the appropriate database. In some examples, the calibration model(s) 3508 can be downloaded through the cloud and updated in the spectral analyzer, which may include a separate dedicated AI engine. Statistical data can be also collected by the AI engine 3504.

In other examples, an artificial intelligence calibration model 3508 can be built for viral detection. For example, a sufficient number of negative and positive samples may be used to train the AI engine 3504. The referencing method can include invasive testing of nasopharyngeal swab with polymerase chain reaction PCR instruments, or cell culturing. A reference sample may be collected from each subject, along with the spectral analyzer measurement. The spectral data 3506a ... 3506N and supporting sensors measurements from each spectral analyzer 3500a ... 3500N, together with the result of the reference technique may be used to train the AI engine 3504. The AI engine 3504 may then build the calibration model 3508 based on a certain number of units of the spectral analyzer 3500a ... 3500N that covers different conditions of the device and manufacturing variations. Then, a global calibration model 3508 may be obtained, collecting measurements from different labs using the cloud 3502. In addition, the developed global calibration model 3508 can be adapted for any new units produced by techniques of model transfer.

Figure 36A:
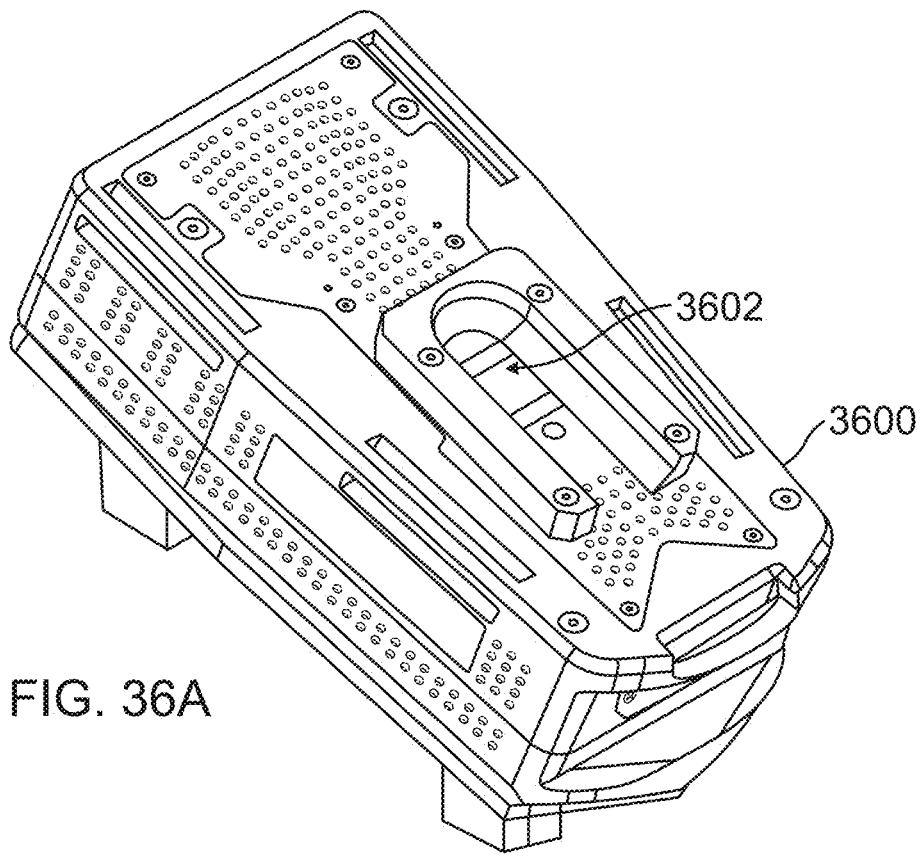
FIGS. 36A-36C are diagrams illustrating an example of a spectral analyzer 3600 for finger measurement according to some aspects.
Figure 36B:
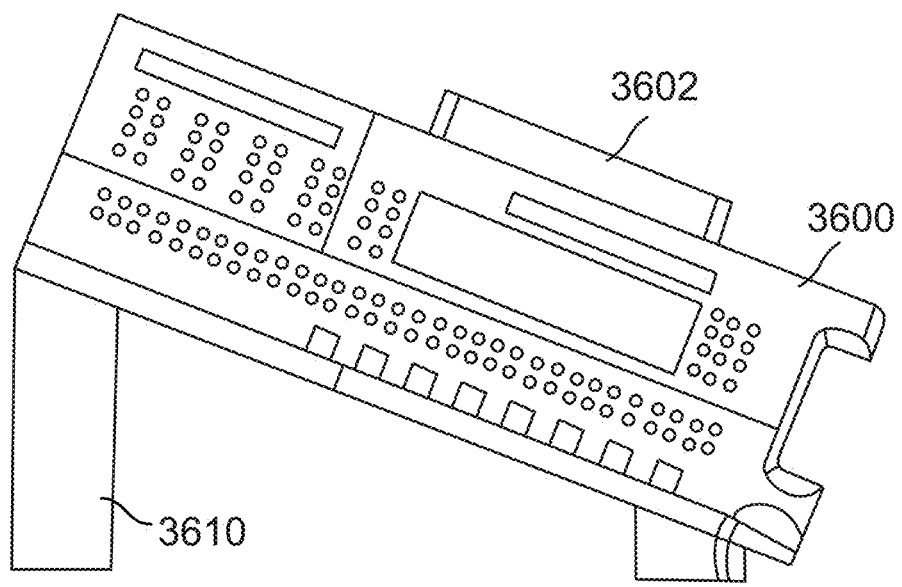
Figure 36C:
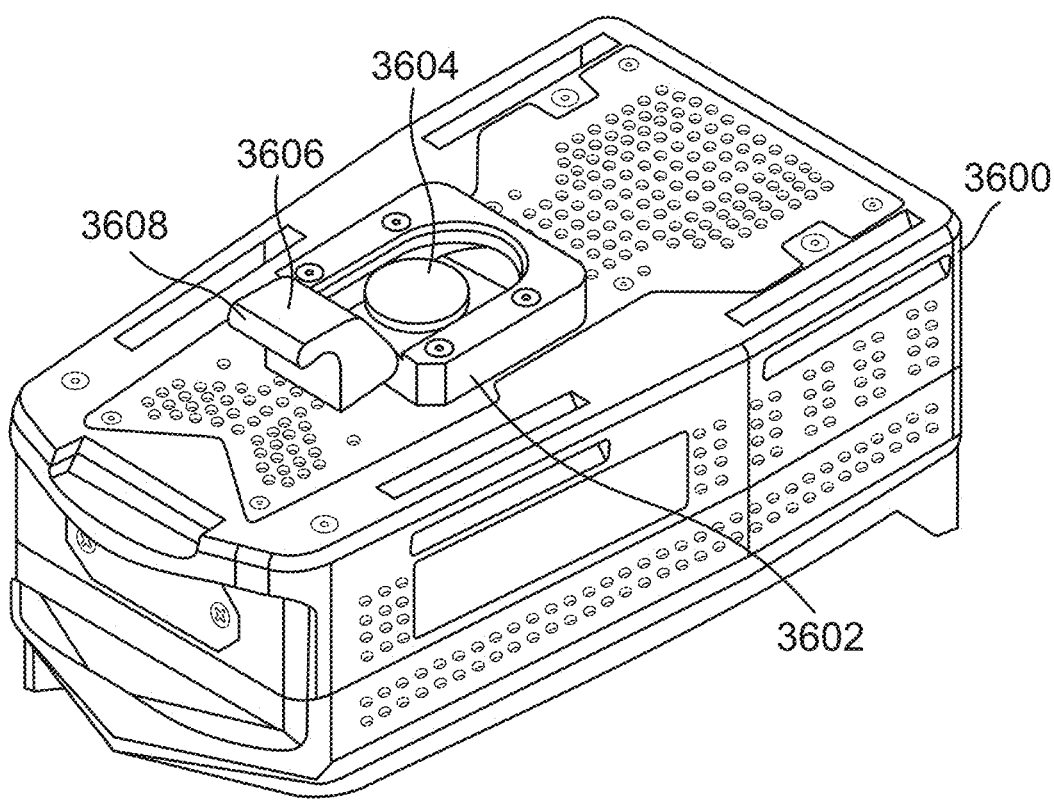

FIGS. 36A-36C are diagrams illustrating an example of a spectral analyzer 3600 for finger measurement according to some aspects. In the example shown in FIG. 36A, the spectral analyzer 3600 includes a finger guiding fixture 3602 attached thereto to guide a user's finger during measurement. In some examples, as shown in FIG. 36B, a tilted mechanical holder 3610 can be used to fix the spectral analyzer 3600 with an angle with respect to a desk/table/surface. In some examples, as shown in FIG. 36C, a removable background tile 3604 (e.g., a reference material with a magnetic cover attached to it) may be configured to fit into the finger guiding fixture 3602 for calibration of the spectral analyzer 3600. In some examples, a holder 3606 for the background/calibration tile 3604 may include a magnet on the backside thereof to enable alignment and insertion of the background tile 3604 into the finger guiding fixture 3602 above the optical window. The holder 3606 may further include a handle 3608 for easy insertion and removal of the background tile 3604.

FIGS. 37A-37C are diagrams illustrating example implementations of the spectral analyzer according to some aspects. In the example shown in FIG. 37A, the spectral analyzer 3700a may be fixed beside an access door 3706 to allow access by analyzing the biochemistry of a finger 3704 of a user (e.g., in addition to a fingerprint of the user). For example, the user can place their finger over an optical window 3702 of the spectral analyzer (e.g., using the finger guiding structure). The spectral analyzer 3700a may then obtain a spectrum of the finger 3704 and may further collect an image of the fingerprint of the user. An AI engine associated with the spectral analyzer 3700a may then use the spectrum (e.g., spectral data) and fingerprint to determine whether to open the door 3706.

In the example shown in FIG. 37B, the spectral analyzer (e.g., spectral analyzer 3700b, 3700c, and/or 3700d) can be integrated into a vehicle 3710 in different locations inside the vehicle. For example, the spectral analyzer 3700b can be integrated into an ignition press button 3714 of the vehicle 3710. For example, as shown in more detail in FIG. 37C, the ignition press button 3714 can include an optically transparent surface 3712 (e.g., a transparent window) to allow spectral analysis when the person pushes the button 3714, causing the transparent window 3712 to come into contact with an optical window 3720 of the spectral analyzer 3700b. As another example, the spectral analyzer 3700c may be integrated into a driving steering wheel of the vehicle 3710. As another example, the spectral analyzer 3700d may be integrated inside a front panel 3718 of the vehicle 3710.

The following provides an overview of examples of the present disclosure.

Example 1: A spectral analyzer, comprising an optical window configured to receive a sample; a spectral sensor, the spectral sensor comprising a chassis, the chassis having assembled thereto: a light source configured to produce input light; an article having an aperture therein configured to receive the input light and further configured to pass a first portion of the input light and block a second portion of the input light; a light modulator configured to receive the first portion of the input light from the article and further configured to produce modulated light based on the first portion of the input light; an illumination optical element configured to direct the modulated light to the optical window for interaction with the sample to produce output light; a detector configured to produce an output signal based on the output light; a collection optical element configured to direct the output light to the detector; and a processor configured to process the output signal to produce spectral data representative of a spectrum of the sample; and a thermal separator positioned between the light modulator and the light source.

Example 2: The spectral analyzer of example 1, further comprising: an artificial intelligence (AI) engine configured to receive the spectrum and to generate a result indicative of at least one parameter associated with the sample based on the spectrum.

Example 3: The spectral analyzer of example 2, wherein the AI engine is configured to select a calibration model from a plurality of calibration models based on the sample.

Example 4: The spectral analyzer of example 3, wherein the plurality of calibration models are cloud-based calibration models built based on data from a plurality of spectral analyzers and corresponding reference values.

Example 5: The spectral analyzer of example 3, further comprising: an in-vitro sample holder configured to contain a reference sample and further configured to replace the optical window or be placed above the optical window during in-vitro sample measurement to generate at least one calibration model of the plurality of calibration models.

Example 6: The spectral analyzer of any of examples 2 through 5, wherein the AI engine is a cloud-based AI engine.

Example 7: The spectral analyzer of any of examples 2 through 6, further comprising: at least one sensor configured to generate sensor data related to the sample and to provide the sensor data to the AI engine, the AI engine configured to produce the result further based on the sensor data.

Example 8: The spectral analyzer of any of examples 1 through 7, wherein the light modulator comprises a micro-electro-mechanical systems (MEMS) interference device.

Example 9: The spectral analyzer of any of examples 1 through 8, further comprising: a first substrate attached to the chassis on a first side thereof, the first substrate further comprising the processor on a top side thereof, the processor further configured to control the light modulator and the detector.

Example 10: The spectral analyzer of example 9, further comprising: a light modulation chip comprising the light modulator, wherein the article comprises a second substrate attached to the chassis on a second side of the chassis, the second substrate being connected to the first substrate, the light modulation chip being attached to a first side of the second substrate opposite a second side of the second substrate adjacent the light source.

Example 11: The spectral analyzer of example 10, further comprising: a third substrate attached to the chassis on the second side thereof, the third substrate being connected to the first substrate via a serial peripheral interface, the third substrate comprising communication circuitry configured to enable communication of the spectral data to an external device.

Example 12: The spectral analyzer of example 11, further comprising: a fourth substrate connected to the first substrate, the third substrate, and the light source, the fourth substrate comprising at least one power management unit (PMU) configured to deliver power to at least the first substrate, the third substrate, and the light source, the fourth substrate being coupled to a backside of the light source such that the fourth substrate is thermally isolated from the first substrate and the second substrate.

Example 13: The spectral analyzer of any of examples 10 through 12, wherein the second substrate is coupled to the chassis via a plurality of screws with springs, the plurality of screws with springs configured to enable the second substrate to tilt for optical alignment of the light modulation chip.

Example 14: The spectral analyzer of any of examples 10 through 13, further comprising: a source cover on the light source, the source cover comprising an additional aperture configured to produce the input light by blocking a portion of incident light generated by the light source, the aperture further configured to match a beam solid angle of the input light to an effective numerical aperture of the light modulator.

Example 15: The spectral analyzer of any of examples 10 through 14, further comprising: a light coupling molded optics component attached to the light modulation chip to couple the first portion of the input light propagating in an out-of-plane direction with respect to a plane of the light modulation chip to an in-plane direction with respect to the plane of the light modulation chip for propagation within the light modulator, the light coupling molded optics component further configured to couple the modulated light propagating in the in-plane direction from the light modulator to the out-of-plane direction for propagation towards the illumination optical element.

Example 16: The spectral analyzer of any of examples 10 through 15, wherein the thermal separator is configured to thermally insulate the first substrate and the second substrate from the light source.

Example 17: The spectral analyzer of any of examples 10 through 16, further comprising: an optics block attached to the second side of the chassis, the optics block comprising at least the collection optical element.

Example 18: The spectral analyzer of any of examples 10 through 17, wherein the detector is attached to the first side of the second substrate, the collection optical element comprising a curved reflector configured to receive the output light and to direct the output light towards the detector.

Example 19: The spectral analyzer of any of claims 9 through 18, further comprising: a heat sink coupled to the light source and attached to the chassis.

Example 20: The spectral analyzer of claim 19, wherein the heat sink forms a part of the chassis.

Example 21: The spectral analyzer of claim 19, wherein the heat sink forms a light source housing containing the light source, the light source housing comprising a threaded hole for optical alignment of the light source.

Example 22: The spectral analyzer of any of examples 19 through 21, further comprising: a fan attached to a light source housing containing the light source.

Example 23: The spectral analyzer of any of examples 9 through 22, further comprising: a fan attached to the chassis on the first side thereof, the first substrate being positioned between the fan and the chassis.

Example 24: The spectral analyzer of any of examples 9 through 23, further comprising: a Peltier element attached to a backside of the first substrate.

Example 25: The spectral analyzer of any of examples 9 through 17 and 19 through 24, wherein the first substrate comprises the detector on a top side thereof, the first substrate further comprising a hole configured to receive a screw for connection of the first substrate to the chassis, the hole comprising a size configured to provide clearance around the screw for optical alignment of the detector.

Example 26: The spectral analyzer of any of examples 1 through 9 and 11 through 25, wherein the article comprises a source cover configured on the light source.

Example 27: The spectral analyzer of example 26, wherein the source cover comprises a metallic cover further configured as a heat sink.

Example 28: The spectral analyzer of any of examples 1 through 27, wherein the collection optical element comprises at least two lenses, the at least two lenses comprising aspheric lenses, ball lenses, or Fresnel lenses.

Example 29: The spectral analyzer of any of examples 1 through 27, wherein the collection optical element comprises a concentrator element, the concentrator element comprising an additional aperture configured to pass the modulated light from the illumination optical element to the optical window.

Example 30: The spectral analyzer of any of examples 1 through 29, wherein the illumination optical element comprises a redirecting mirror and a focusing lens, the redirecting mirror configured to direct the modulated light towards the optical window through the focusing lens.

Example 31: The spectral analyzer of example 30, wherein the redirecting mirror is attached to the chassis via a hinge and is configured to be rotated for optical alignment of the redirecting mirror.

Example 32: The spectral analyzer of any of examples 1 through 31, wherein the optical window comprises a first optical window and a second optical window, and further comprising: a sample compartment formed between the first optical window and the second optical window and configured to receive the sample, the sample compartment being positioned between the illumination optical element and the collection optical element to operate the spectral analyzer in a transmission mode.

Example 33: The spectral analyzer of any of examples 1 through 32, wherein: the light source comprises a first light source configured to produce first input light and a second light source configured to produce second input light, the light modulator comprises a first light modulator configured to produce first modulated light based on the first input light and a second light modulator configured to produce second modulated light based on the second input light; and the illumination optical element comprises a first illumination optical element configured to direct the first modulated light to the optical window and a second illumination optical element configured to direct the second modulated light to the optical window.

Example 34: The spectral analyzer of any of examples 1 through 33, wherein the illumination optical element comprises a focusing lens, and wherein the light source and the light modulator are positioned to align respective optical axes of the light source, the light modulator, and the focusing lens, the respective optical axes being further aligned with a direction of incidence on the sample.

Example 35: The spectral analyzer of any of examples 1 through 34, wherein the collection optical element and the detector form a light detection module, the light detection module being configured such that an optical axis of the light detection module is displaced by a first distance from an intersection of the modulated light and the optical window.

Example 36: The spectral analyzer of example 35, wherein an imaging plane of the light detection module is displaced from the optical window by a second distance, the first distance and the second distance being configured to enable illumination of a layer within the sample separated from a surface layer of the sample adjacent the optical window.

Example 37: The spectral analyzer of any of examples 1 through 36, further comprising: a removable band-pass filter configured to be inserted between the light source and the light modulator.

Example 38: The spectral analyzer of example 37, further comprising: a first lens and a second lens configured to collimate the first portion of the input light, the removable band-pass filter being inserted between the first lens and the second lens.

Example 39: The spectral analyzer of example 37, further comprising: a tile comprising a reference material removably attached to the optical window during calibration of the spectral analyzer to obtain a reference spectrum.

Example 40: The spectral analyzer of any of examples 1 through 40, wherein the illumination optical element comprises a beam splitter, configured to split the modulated light into a first modulated light beam directed towards the optical window and a second modulated light beam, and further comprising: an additional detector configured to receive the second modulated light beam to obtain a reference spectrum to calibrate the spectral analyzer; and a reflector configured to direct the second modulated light beam toward the additional detector.

Example 41: The spectral analyzer of any of examples 1 through 40, wherein the illumination optical element comprises a redirecting mirror, and further comprising: a rotating motor configured to rotate the redirecting mirror between a first position at which the modulated light is directed towards the optical window to obtain the spectrum of the sample in a measurement mode and a second position at which the modulated light is directed towards the detector via a reflector to obtain a reference spectrum in a reference mode.

Example 42: The spectral analyzer of any of examples 1 through 40, further comprising: a tile comprising a reference material; and a linear motor configured to move the tile between a first position under the optical window to obtain a reference spectrum in a reference mode and a second position away from the optical window to obtain the spectrum of the sample in a measurement mode.

Example 43: The spectral analyzer of any of examples 1 through 42, wherein the spectral analyzer is a wearable device, and wherein the optical window further comprises at least one microfluidic channel configured to displace water from the optical window.

Example 44: The spectral analyzer of any of examples 1 through 42, wherein the spectral analyzer is integrated into a vehicle.

Example 45: The spectral analyzer of example 44, wherein the vehicle comprises an ignition press including a transparent window above the optical window.

Example 46: The spectral analyzer of any of examples 1 through 44, further comprising: a finger guiding fixture attached to a housing of the spectral analyzer and positioned above the optical window.

Example 47: The spectral analyzer of example 46, further comprising: a removable background tile configured to fit into the finger guiding fixture for calibration of the spectral analyzer.

Within the present disclosure, the word "exemplary" is used to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure.

One or more of the components, steps, features and/or functions illustrated in FIGS. 1-37C may be rearranged and/or combined into a single component, step, feature or function or embodied in several components, steps, or functions. Additional elements, components, steps, and/or functions may also be added without departing from novel features disclosed herein. The apparatus, devices, and/or components illustrated in FIGS. 1-37C may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A spectral analyzer, comprising:
    an optical window configured to receive a sample;
    a spectral sensor, the spectral sensor comprising a chassis, the chassis having assembled thereto:
        a light source configured to produce input light;
        an article having an aperture therein configured to receive the input light and further configured to pass a first portion of the input light and block a second portion of the input light;
        a light modulator configured to receive the first portion of the input light from the article and further configured to produce modulated light based on the first portion of the input light;
        an illumination optical element configured to direct the modulated light to the optical window for interaction with the sample to produce output light;
        a detector configured to produce an output signal based on the output light;
        a collection optical element configured to direct the output light to the detector; and
        a processor configured to process the output signal to produce spectral data representative of a spectrum of the sample; and
    a thermal separator positioned between the light modulator and the light source.

2. The spectral analyzer of claim 1, further comprising:
    an artificial intelligence (AI) engine configured to receive the spectrum and to generate a result indicative of at least one parameter associated with the sample based on the spectrum.

3. The spectral analyzer of claim 2, wherein the AI engine is configured to select a calibration model from a plurality of calibration models based on the sample.

4. The spectral analyzer of claim 3, wherein the plurality of calibration models are cloud-based calibration models built based on data from a plurality of spectral analyzers and corresponding reference values.

5. The spectral analyzer of 3, further comprising:
    an in-vitro sample holder configured to contain a reference sample and further configured to replace the optical window or be placed above the optical window during in-vitro sample measurement to generate at least one calibration model of the plurality of calibration models.

6. The spectral analyzer of claim 2, wherein the AI engine is a cloud-based AI engine.

7. The spectral analyzer of claim 2, further comprising:
    at least one sensor configured to generate sensor data related to the sample and to provide the sensor data to the AI engine, the AI engine configured to produce the result further based on the sensor data.

8. The spectral analyzer of claim 1, wherein the light modulator comprises a micro-electro-mechanical systems (MEMS) interference device.

9. The spectral analyzer of claim 1, further comprising:
    a first substrate attached to the chassis on a first side thereof, the first substrate further comprising the processor on a top side thereof, the processor further configured to control the light modulator and the detector.

10. The spectral analyzer of claim 9, further comprising:
    a light modulation chip comprising the light modulator, wherein the article comprises a second substrate attached to the chassis on a second side of the chassis, the second substrate being connected to the first substrate, the light modulation chip being attached to a first side of the second substrate opposite a second side of the second substrate adjacent the light source.

11. The spectral analyzer of claim 10, further comprising:
    a third substrate attached to the chassis on the second side thereof, the third substrate being connected to the first substrate via a serial peripheral interface, the third substrate comprising communication circuitry configured to enable communication of the spectral data to an external device.

12. The spectral analyzer of claim 11, further comprising:

a fourth substrate connected to the first substrate, the third substrate, and the light source, the fourth substrate comprising at least one power management unit (PMU) configured to deliver power to at least the first substrate, the third substrate, and the light source, the fourth substrate being coupled to a backside of the light source such that the fourth substrate is thermally isolated from the first substrate and the second substrate.

13. The spectral analyzer of claim 10, wherein the second substrate is coupled to the chassis via a plurality of screws with springs, the plurality of screws with springs configured to enable the second substrate to tilt for optical alignment of the light modulation chip.

14. The spectral analyzer of claim 10, further comprising:
a source cover on the light source, the source cover comprising an additional aperture configured to produce the input light by blocking a portion of incident light generated by the light source, the aperture further configured to match a beam solid angle of the input light to an effective numerical aperture of the light modulator.

15. The spectral analyzer of claim 10, further comprising:
a light coupling molded optics component attached to the light modulation chip to couple the first portion of the input light propagating in an out-of-plane direction with respect to a plane of the light modulation chip to an in-plane direction with respect to the plane of the light modulation chip for propagation within the light modulator, the light coupling molded optics component further configured to couple the modulated light propagating in the in-plane direction from the light modulator to the out-of-plane direction for propagation towards the illumination optical element.

16. The spectral analyzer of claim 10, wherein the thermal separator is configured to thermally insulate the first substrate and the second substrate from the light source.

17. The spectral analyzer of claim 10, further comprising:
an optics block attached to the second side of the chassis, the optics block comprising at least the collection optical element.

18. The spectral analyzer of claim 10, wherein the detector is attached to the first side of the second substrate, the collection optical element comprising a curved reflector configured to receive the output light and to direct the output light towards the detector.

19. The spectral analyzer of claim 9, further comprising:
a heat sink coupled to the light source and attached to the chassis.

20. The spectral analyzer of claim 19, wherein the heat sink forms a part of the chassis.

21. The spectral analyzer of claim 19, wherein the heat sink forms a light source housing containing the light source, the light source housing comprising a threaded hole for optical alignment of the light source.

22. The spectral analyzer of claim 19, further comprising:
a fan attached to a light source housing containing the light source.

23. The spectral analyzer of claim 9, further comprising:
a fan attached to the chassis on the first side thereof, the first substrate being positioned between the fan and the chassis.

24. The spectral analyzer of claim 9, further comprising:
a Peltier element attached to a backside of the first substrate.

25. The spectral analyzer of claim 9, wherein the first substrate comprises the detector on a top side thereof, the first substrate further comprising a hole configured to receive a screw for connection of the first substrate to the chassis, the hole comprising a size configured to provide clearance around the screw for optical alignment of the detector.

26. The spectral analyzer of claim 1, wherein the article comprises a source cover configured on the light source.

27. The spectral analyzer of claim 26, wherein the source cover comprises a metallic cover further configured as a heat sink.

28. The spectral analyzer of claim 1, wherein the collection optical element comprises at least two lenses, the at least two lenses comprising aspheric lenses, ball lenses, or Fresnel lenses.

29. The spectral analyzer of claim 1, wherein the collection optical element comprises a concentrator element, the concentrator element comprising an additional aperture configured to pass the modulated light from the illumination optical element to the optical window.

30. The spectral analyzer of claim 1, wherein the illumination optical element comprises a redirecting mirror and a focusing lens, the redirecting mirror configured to direct the modulated light towards the optical window through the focusing lens.

31. The spectral analyzer of claim 30, wherein the redirecting mirror is attached to the chassis via a hinge and is configured to be rotated for optical alignment of the redirecting mirror.

32. The spectral analyzer of claim 1, wherein the optical window comprises a first optical window and a second optical window, and further comprising:
a sample compartment formed between the first optical window and the second optical window and configured to receive the sample, the sample compartment being positioned between the illumination optical element and the collection optical element to operate the spectral analyzer in a transmission mode.

33. The spectral analyzer of claim 1, wherein:
the light source comprises a first light source configured to produce first input light and a second light source configured to produce second input light,
the light modulator comprises a first light modulator configured to produce first modulated light based on the first input light and a second light modulator configured to produce second modulated light based on the second input light; and
the illumination optical element comprises a first illumination optical element configured to direct the first modulated light to the optical window and a second illumination optical element configured to direct the second modulated light to the optical window.

34. The spectral analyzer of claim 1, wherein the illumination optical element comprises a focusing lens, and wherein the light source and the light modulator are positioned to align respective optical axes of the light source, the light modulator, and the focusing lens, the respective optical axes being further aligned with a direction of incidence on the sample.

35. The spectral analyzer of claim 1, wherein the collection optical element and the detector form a light detection module, the light detection module being configured such that an optical axis of the light detection module is displaced by a first distance from an intersection of the modulated light and the optical window.

36. The spectral analyzer of claim 35, wherein an imaging plane of the light detection module is displaced from the optical window by a second distance, the first distance and the second distance being configured to enable illumination of a layer within the sample separated from a surface layer of the sample adjacent the optical window.

37. The spectral analyzer of claim 1, further comprising: a removable band-pass filter configured to be inserted between the light source and the light modulator.

38. The spectral analyzer of claim 37, further comprising: a first lens and a second lens configured to collimate the first portion of the input light, the removable band-pass filter being inserted between the first lens and the second lens.

39. The spectral analyzer of claim 37, further comprising: a tile comprising a reference material removably attached to the optical window during calibration of the spectral analyzer to obtain a reference spectrum.

40. The spectral analyzer of claim 1, wherein the illumination optical element comprises a beam splitter, configured to split the modulated light into a first modulated light beam directed towards the optical window and a second modulated light beam, and further comprising:
 an additional detector configured to receive the second modulated light beam to obtain a reference spectrum to calibrate the spectral analyzer; and
 a reflector configured to direct the second modulated light beam toward the additional detector.

41. The spectral analyzer of claim 1, wherein the illumination optical element comprises a redirecting mirror, and further comprising:
 a rotating motor configured to rotate the redirecting mirror between a first position at which the modulated light is directed towards the optical window to obtain the spectrum of the sample in a measurement mode and a second position at which the modulated light is directed towards the detector via a reflector to obtain a reference spectrum in a reference mode.

42. The spectral analyzer of claim 1, further comprising:
 a tile comprising a reference material; and
 a linear motor configured to move the tile between a first position under the optical window to obtain a reference spectrum in a reference mode and a second position away from the optical window to obtain the spectrum of the sample in a measurement mode.

43. The spectral analyzer of claim 1, wherein the spectral analyzer is a wearable device, and wherein the optical window further comprises at least one microfluidic channel configured to displace water from the optical window.

44. The spectral analyzer of claim 1, wherein the spectral analyzer is integrated into a vehicle.

45. The spectral analyzer of claim 44, wherein the vehicle comprises an ignition press including a transparent window above the optical window.

46. The spectral analyzer of claim 1, further comprising:
 a finger guiding fixture attached to a housing of the spectral analyzer and positioned above the optical window.

47. The spectral analyzer of claim 46, further comprising:
 a removable background tile configured to fit into the finger guiding fixture for calibration of the spectral analyzer.

\* \* \* \* \*